US010640567B2

(12) United States Patent
Ellmark et al.

(10) Patent No.: US 10,640,567 B2
(45) Date of Patent: *May 5, 2020

(54) ANTI-CD40 ANTIBODIES AND METHODS OF TREATING CANCER HAVING CD40+ TUMOR CELLS

(71) Applicant: ALLIGATOR BIOSCIENCE AB, Lund (SE)

(72) Inventors: Peter Bo Joakim Ellmark, Lund (SE); Eva Maria Dahlen, Arlov (SE)

(73) Assignee: ALLIGATOR BIOSCIENCE AB, Lund (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,919

(22) Filed: May 8, 2017

(65) Prior Publication Data
US 2017/0240642 A1     Aug. 24, 2017

Related U.S. Application Data

(62) Division of application No. 14/342,141, filed as application No. PCT/GB2012/052179 on Sep. 5, 2012, now Pat. No. 9,676,862.

(30) Foreign Application Priority Data

Sep. 5, 2011 (GB) .................................. 1115280.8

(51) Int. Cl.

| A61K 39/395 | (2006.01) |
|---|---|
| C07K 16/28 | (2006.01) |
| A61K 49/00 | (2006.01) |
| C07K 16/46 | (2006.01) |
| A61K 9/00 | (2006.01) |
| A61K 9/02 | (2006.01) |
| A61K 9/08 | (2006.01) |
| A61K 9/20 | (2006.01) |
| A61K 9/48 | (2006.01) |
| A61K 51/10 | (2006.01) |
| A61K 39/00 | (2006.01) |

(52) U.S. Cl.
CPC ........ *C07K 16/2878* (2013.01); *A61K 9/0019* (2013.01); *A61K 9/0048* (2013.01); *A61K 9/02* (2013.01); *A61K 9/08* (2013.01); *A61K 9/20* (2013.01); *A61K 9/48* (2013.01); *A61K 39/3955* (2013.01); *A61K 49/00* (2013.01); *A61K 51/103* (2013.01); *A61K 51/1096* (2013.01); *C07K 16/468* (2013.01); *A61K 2039/505* (2013.01); *A61K 2039/70* (2013.01); *C07K 2317/21* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/565* (2013.01); *C07K 2317/622* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,312,693 B1 | 11/2001 | Aruffo et al. |
|---|---|---|
| 9,676,862 B2 * | 6/2017 | Ellmark ............... A61K 9/0019 |
| 2003/0211100 A1 * | 11/2003 | Bedian ............... C07K 16/2878 |
| | | 424/144.1 |
| 2004/0110226 A1 | 6/2004 | Lazar et al. |
| 2004/0132066 A1 | 7/2004 | Balint et al. |
| 2006/0166198 A1 | 7/2006 | Furebring et al. |
| 2007/0077242 A1 | 4/2007 | Kirin |
| 2008/0248533 A1 * | 10/2008 | Carlsson ............... C12N 15/10 |
| | | 435/91.2 |
| 2011/0027276 A1 | 2/2011 | Bernett et al. |
| 2012/0225014 A1 | 9/2012 | Bedian et al. |

FOREIGN PATENT DOCUMENTS

| EP | 1885399 B1 | 2/2008 |
|---|---|---|
| EP | 2011802 A3 | 4/2009 |
| WO | 2001083755 A2 | 11/2001 |
| WO | 2002048351 A2 | 6/2002 |
| WO | 2002/088186 A1 | 11/2002 |
| WO | 2003/040170 A3 | 5/2003 |
| WO | 2003097834 A2 | 11/2003 |

(Continued)

OTHER PUBLICATIONS

Vonderheide et al., Clin Cancer Res 19: 1035-1043 (2013) (Year: 2013).*
Advani et al., Phase I Study of the humanized anti-CD40 monoclonal antibody Dacetuzumab in refractory of recurrrent non-hodgkin's lymphoma, J Clinical Oncology, 2009, 4371-4377, 27.
Armitage et al., Molecular and biological characterization of a murine ligand for CD40, Nature, 1992, 80-82, 357.
Bajorath et al., Detailed comparison of two molecular models of the human CD40 ligand with an x-ray structure and critical assessment of model-based mutagenesis and residue mapping studies, J Biol Chem , 1998, 24603-9, 273.
Bajorath et al., Identification of residues on CD40 and its ligand which are critical for the receptor-ligand interaction, Biochemistry, 1995, 1833-44, 34.

(Continued)

*Primary Examiner* — Phillip Gambel
(74) *Attorney, Agent, or Firm* — Robert C. Netter, Jr.; Dann, Dorfman, Herrell & Skillman

(57) ABSTRACT

The present invention relates to antibodies (and fragments, variants, fusions and derivatives thereof) with multivalent binding specificity for CD40, which have a potency for dendritic cell activation which is higher than, or is equal to, the potency for B cell activation and wherein the antibody, antigen-binding fragment, or fusion, variant or derivative thereof has an affinity (KD) for CD40 of less than $1 \times 10^{-10}$ M, which have utility in the treatment of diseases such as cancer. The invention also relates to pharmaceutical compositions, uses, methods and kits comprising such antibodies.

Figure 1A:
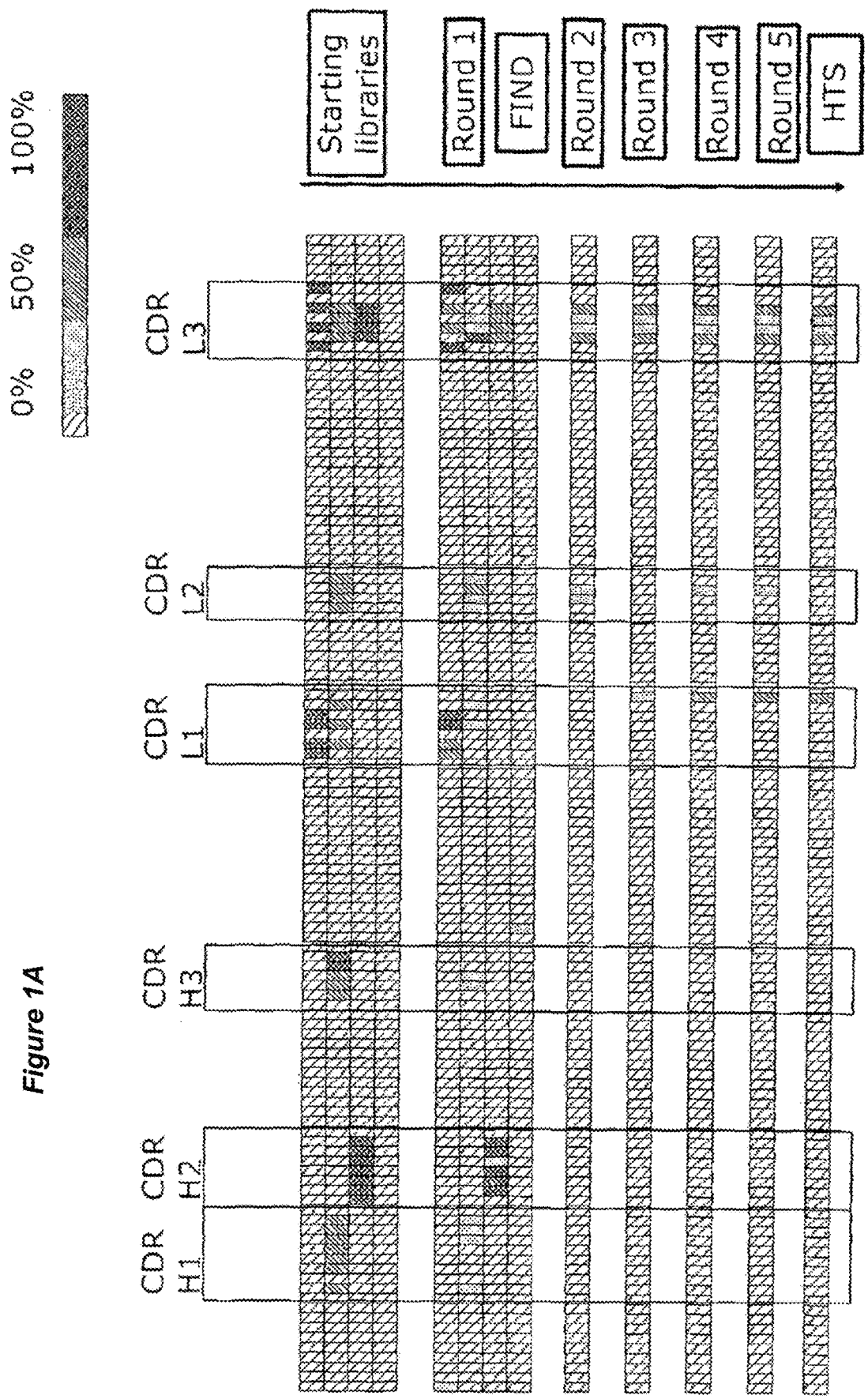

20 Claims, 15 Drawing Sheets
Specification includes a Sequence Listing.

(56) References Cited

FOREIGN PATENT DOCUMENTS

| | | |
|---|---|---|
| WO | 2006073443 A2 | 7/2006 |
| WO | 2009094391 A1 | 7/2009 |

OTHER PUBLICATIONS

Diehl et al., CD40 activation in vivo overcomes peptide-induced peripheral cytotoxic T- lymphocyte tolerance and augments anti-tumor vaccine efficacy, Nat. Med., 1999, 774-779, 5.

Ellmark et al., Identification of a Strongly Activating Human Anti-Cd40 Antibody that Suppresses HIV Type 1 Infection, AIDS Research and Human Rettroviruses, 2008, 367- 373, 24(3).

Ellmark et al., Modulation of the CD40-CD40L ligand interaction using human anti-CD40 single-chain antibody fragments obtained from the n-CoDeR® phage display library, Immunology, 2002, 456-463, 106.

Fellouse et al., High-throughput generation of synthetic antibodies from highly functional minimalist phage-displayed libraries, J Mo/ Biol, 2007, 924-940, 373.

Francisco et al., Agonistic properties and in vivo antitumor activity of the anti-CD40 antibody SGN-14, Cancer Research, 2000, 3225-3231, 60.

French et al., CD40 antibody evokes a cytotoxic T-cell response that eradicates lymphoma and bypasses T-cell help, Nat Med, 1999, 548-53, 5.

Quezada et al., CD40/CD154 interactions at the interface of tolerance and immunity, Annu. Rev. Immunol., 2004, 307-328, 22.

Siepmann et al., Rewiring CD40 is necessary for delivery of rescue signals to B cells in germinal centres and subsequent entry into the memory pool, Immunology, 2001, 263-72, 102(3).

Tong et al., Prospects for CD40-derived experimental therapy of human cancer, Cancer Gene Therapy, 2003, 1-13, 10(1).

Van Mierlo et al., CD40 stimulation leads to effective therapy of CD40(−) tumors through induction of strong systemic cytotoxic T lymphocyte immunity, Proc. Natl. Acad. Sci. U. S. A., 2002, 5561-5566, 99.

White et al., Interaction with FcCRIIB is critical for the agonistic activity of anti-CD40 monoclonal antibody, Journal of Immunology, 2011, 1754-1763, 187.

Allen et al., CD40 ligand gene defects responsible for X-linked hyper-IgM syndrome, Science, 1993, 990-993, 259.

Bajorath et al., Analysis of gp39/CD40 interactions using molecular models and site- directed mutagenesis, Biochemistry, 1995, 9884-92, 34.

Berinstein et al., Enhancing cancer vaccines with immunomodulators, Vaccine, 2007, B72-B88, 25(Suppl 2).

Ellmark et al., Pre-assembly of the extracellular domains of CD40 is not necessary for rescue of mouse B cells from anti-immunoglobulin M-induced apoptosis, Immunology, 2003, 452-7, 108.

Foy et al., In vivo CD40-gp39 interactions are essential for thymus-dependent humoral immunity. II. Prolonged suppression of the humoral immune response by an antibody to the ligand for CD40, J Exp Med., 1993, 1567-1575, 5.

Gatenby et al., Why do cancers have high aerobi glycolysis? Nature Review Cancer, 2004, 891-899, 4.

Gladue et al., The CD40 agonist antibody CP-870,893 enhances dendritic cell and B-cell activity and promotes anti-tumor efficacy in SCID-hu mice, Cancer Immunol Immunotherapy, 2011, 1009-17, 60(7).

Hussein et al., A phase I multi-dose study of dacetumuzumab (SGN-40, a humananoid anti-CD40 monoclonal antibody) in patients with multiple myeloma, 2010, Haematologica, 845-848, 95.

Kai et al., Switching constant domains enhances agonist activities of antibodies to a thrombopoietin receptor, Nature Biotechnology, 2008, 209-211, 26.

Kalbasi et al., CD40 expression by human melanocytic lesions and melanoma cell lines and direct CD40 targeting with the therapeutic anti-CD40 antibody CP-870,893, J Immunother, 2010, 810-816, 33.

Katakura et al., A practical kinetic model for efficient isolation of useful antibodies from phage display libraries, Journal of Molecular Catalysis B: Enzymatic, 2004, 191-200, 28(4-6).

Khalil et al., Anti-CD40 agonist antibodies: preclinical and clinical experience, Update Cancer Ther., 2007, 61-65, 2, (2).

Khawli et al., Cytokine, Chemokine, and Co-Stimulatory Fusion Proteins for the Immunotherapy of Solid Tumors, Handb. Exp. Pharmacol., 2008, 291-328, 181.

Law et al., Preclinical Antilymphoma Activity of a Humanized Anti-CD40 Monoclonal Antibody, SGN-40, Cancer Research, 2005, 8331-8338, 65.

Loskog et al., The Janus faces of CD40 in cancer, Semin. Immunol, 2009, 301-307, 21.

Melero et al., Immunostimulatory monoclonal antibodies for cancer therapy, Nat Rev Cancer, 2007, 95-106, 7.

Melief et al., Strategies for Immunotherapy of Cancer, Adv. Immunol., 2000, 235-282, 75.

Melief et al., Cancer Immunotherapy by Dendritic Cells, Immunity, 2008, 372-383, 29.

Mellor et al., Creating immune privilege: active local suppression that benefits friends, but protects foes, Nat Rev Immunol., 2008, 74-80, 8.

Mierlo et al., CD40 stimulation leads to effective therapy of CD40 tumors through induction of strong systemic cytotoxic T lymphocyte immunity, Proc. Natl. Acad. Sci. USA, 2002, 5561-5566, 99.

Neron et al., CD40-activated B cells from patients with systemic lupus erythematosus can be modulated by terapeutic immunoglobulins in vitro, Arch. Immunol. Ther. Exp., 2009, 447-458, 57.

Wilson et al., An Fcg Receptor-Dependent Mechanism Drives Antibody-Mediated Target-Receptor Signaling in Cancer Cells, Cancer Cell, 2011, 101-113, 19.

Ottaiano et al., CD40 activation as potential tool in malignant neoplasms, Tumori, 2002, 361-366, 88.

Pound et al., Minimal cross-linking and epitope requirements for CD40-dependent suppression of apoptosis contrast with those for promotion of the cell cycle and homotypic adhesions in human B cells, International Immunology, 1999, 11-20, 11(1).

Schonbeck et al., The CD40/CD154 receptor/ligand dyad, Cell. Life. Sci., 2001, 4-43, 58.

Sklar et al., Flow cytometric analysis of ligand-receptor interactions and molecular assemblies, Annual Review Biophysical Biomol Structure, 2002, 97-119, 31.

Soderlind et al., Recombining germline-derived CDR sequences for creating diverse single framework antibody librariesNat Biotechnol, 2000, 852-6, 18.

Sotomayor et al., Conversion of tumor-specific CD4+ T-cell tolerance to T-cell priming through in vivo ligation of CD40, Nature Medicine 1999, 780-787, 5.

Stagg et al., From cancer immunosurveillance to cancer immunotherapy, Immunological Reviews, 2007, 82-101, 220.

Staveley-O'Carroll et al., In Vivo Ligation of CD40 Enhances Priming Against the Endogenous Tumor Antigen and Promotes CD8+ T Cell Effector Function in SV40 T Antigen Transgenic Mice, J Immunol, 2003, 697-707, 171.

Tutt et al., T cell immunity to lymphoma following treatment with anti-CD40 monoclonal antibody, J Immunol, 2002, 2720-2728, 168(6).

Van Mierlo et al., Activation of Dendritic Cells That Cross-Present Tumor-Derived Antigen Licenses CD8 CTL to Cause Tumor Eradication, J Immunol, 2004, 6753-6759, 173.

Vonderheide et al., Clinical Activity and Immune Modulation in Cancer Patients Treated With CP-870,893, a Novel CD40 Agonist Monoclonal Antibody, J Clin Oncol., 2007, 876-83, 25(7).

Waldmann et al., Effective cancer therapy through immunomodulation, Annu Rev Med., 2006, 65-81, 57.

Malmborg Hager, A.C., "Affinity and Epitope Profiling of Mouse Anti-CD40 Monoclonal Antibodies," Scandinavian J. Immunol. (2003) 57:517-524.

Neron et al., Tuning of CD40—CD154 Interactions in Human B-Lymphocyte Activation: A Broad Array of In Vitro Models for a Complex In Vivo Situation, Archivum Immunologiae et Therapiae Experimentalis, 2011, 25-40, 59.

(56) References Cited

OTHER PUBLICATIONS

Huang et al., Sensitization of SiHa cell to gemcitabine by CD40 activation and its overexpression in cervical carcinoma, Medical Oncology, 2010, 781-788, 28.
Huout et al., Immunomodulating antibodies and drugs for the treatment of hematological malignancies, Cancer Metastasis Rev. 2011, 97-109, 30.
Rudikoff et al., Single amino acid substitution altering antigen-binding specificity, Proc. Natl. Acad. Sci., 1982, 79:1979-1983.
Colman, P.M., Effects of amino acid sequence changes on antibody-antigen interactions, Res. Immunology, 1994, 145:33-36.
Kussie, et al., A single engineered amino acid substitution changes antibody fine specificity, J. Immunol., 1994, 152:146-152.
Chen, et al., Enhancement and destruction of antibody function by somatic mutation: unequal occurrence is controlled by V gene combinatorial associations, EMBO J., 14:2784-2794.
Janeway, C.A., et al., Immunobiology 5: The Immune System in Health and Diseases, 2001, Garland Publishing, New York, pp. 559-560.
Humm, J.L., et al., "Editorial: F(ab')2 Fragments Versus Intact Antibody—An Isodose Comparison," J. Nucl. Med. (1990) 31(6)1045-1047.
Cheng, K.T., "Radioiodinated anti-TAG-72 CC49 Fab' antibody fragment," 2008, In: Molecular Imaging and Contrast Agent Database (MICAD), Bethesda (MD):National Center for Biotechnology Information (US); 2004-2013, pp. 1-6.
Shan, L., "124I-Labeled anti-prostate stem cell antigen affinity-matured A11 minibody" 2010, In: Molecular Imaging and Contrast Agent Database (MICAD). Bethesda (MD): National Center for Biotechnology Information (US); 2004-2013, pp. 1-5.

\* cited by examiner

SEQUENCE LISTING

```
<160> NUMBER OF SEQ ID NOS: 67

<210> SEQ ID NO 1
<211> LENGTH: 15
<212> TYPE: PRT
<213> ORGANISM: Homo sapiens
<220> FEATURE:
<221> NAME/KEY: VARIANT
<222> LOCATION: 5
<223> OTHER INFORMATION: Xaa is Ser or Thr
<220> FEATURE:
<221> NAME/KEY: VARIANT
<222> LOCATION: 13
<223> OTHER INFORMATION: Xaa is Lys or His or Asp or Gly or Asn

<400> SEQUENCE: 1

Cys Thr Gly Ser Xaa Ser Asn Ile Gly Ala Gly Tyr Xaa Val Tyr
1               5                   10                  15

<210> SEQ ID NO 2
<211> LENGTH: 7
<212> TYPE: PRT
<213> ORGANISM: Homo sapiens
<220> FEATURE:
<221> NAME/KEY: VARIANT
<222> LOCATION: 1
<223> OTHER INFORMATION: Xaa is Gly or Arg

<400> SEQUENCE: 2

Xaa Asn Ile Asn Arg Pro Ser
1               5

<210> SEQ ID NO 3
<211> LENGTH: 12
<212> TYPE: PRT
<213> ORGANISM: Homo sapiens
<220> FEATURE:
```

```
<221> NAME/KEY: VARIANT
<222> LOCATION: 6
<223> OTHER INFORMATION: Xaa is Asp or Ser or Glu or Gly or Lys
<220> FEATURE:
<221> NAME/KEY: VARIANT
<222> LOCATION: 7
<223> OTHER INFORMATION: Xaa is Ser or Thr or Gly
<220> FEATURE:
<221> NAME/KEY: VARIANT
<222> LOCATION: 8
<223> OTHER INFORMATION: Xaa is Ser or Thr or Leu or Ile
<220> FEATURE:
<221> NAME/KEY: VARIANT
<222> LOCATION: 9
<223> OTHER INFORMATION: Xaa is Ser or Thr or Leu
<220> FEATURE:
<221> NAME/KEY: VARIANT
<222> LOCATION: 12
<223> OTHER INFORMATION: Val or Leu

<400> SEQUENCE: 3

Cys Ala Ala Trp Asp Xaa Xaa Xaa Xaa Gly Leu Xaa
1               5                   10

<210> SEQ ID NO 4
<211> LENGTH: 15
<212> TYPE: PRT
<213> ORGANISM: Homo sapiens

<400> SEQUENCE: 4

Cys Thr Gly Ser Thr Ser Asn Ile Gly Ala Gly Tyr Lys Val Tyr
1               5                   10                  15

<210> SEQ ID NO 5
<211> LENGTH: 15
<212> TYPE: PRT
<213> ORGANISM: Homo sapiens

<400> SEQUENCE: 5

Cys Thr Gly Ser Ser Ser Asn Ile Gly Ala Gly Tyr His Val Tyr
1               5                   10                  15

<210> SEQ ID NO 6
<211> LENGTH: 15
<212> TYPE: PRT
<213> ORGANISM: Homo sapiens

<400> SEQUENCE: 6

Cys Thr Gly Ser Ser Ser Asn Ile Gly Ala Gly Tyr Lys Val Tyr
1               5                   10                  15

<210> SEQ ID NO 7
<211> LENGTH: 15
<212> TYPE: PRT
<213> ORGANISM: Homo sapiens

<400> SEQUENCE: 7

Cys Thr Gly Ser Ser Ser Asn Ile Gly Ala Gly Tyr Asp Val Tyr
1               5                   10                  15

<210> SEQ ID NO 8
<211> LENGTH: 15
<212> TYPE: PRT
<213> ORGANISM: Homo sapiens

<400> SEQUENCE: 8

Cys Thr Gly Ser Ser Ser Asn Ile Gly Ala Gly Tyr Gly Val Tyr
1               5                   10                  15
```

<210> SEQ ID NO 9
<211> LENGTH: 15
<212> TYPE: PRT
<213> ORGANISM: Homo sapiens

<400> SEQUENCE: 9

Cys Thr Gly Ser Ser Ser Asn Ile Gly Ala Gly Tyr Asn Val Tyr
1               5                   10                  15

<210> SEQ ID NO 10
<211> LENGTH: 7
<212> TYPE: PRT
<213> ORGANISM: Homo sapiens

<400> SEQUENCE: 10

Gly Asn Ile Asn Arg Pro Ser
1               5

<210> SEQ ID NO 11
<211> LENGTH: 7
<212> TYPE: PRT
<213> ORGANISM: Homo sapiens

<400> SEQUENCE: 11

Arg Asn Ile Asn Arg Pro Ser
1               5

<210> SEQ ID NO 12
<211> LENGTH: 12
<212> TYPE: PRT
<213> ORGANISM: Homo sapiens

<400> SEQUENCE: 12

Cys Ala Ala Trp Asp Asp Ser Leu Ser Gly Leu Val
1               5                   10

<210> SEQ ID NO 13
<211> LENGTH: 12
<212> TYPE: PRT
<213> ORGANISM: Homo sapiens

<400> SEQUENCE: 13

Cys Ala Ala Trp Asp Ser Ser Ser Gly Leu Val
1               5                   10

<210> SEQ ID NO 14
<211> LENGTH: 12
<212> TYPE: PRT
<213> ORGANISM: Homo sapiens

<400> SEQUENCE: 14

Cys Ala Ala Trp Asp Glu Ser Ile Thr Gly Leu Val
1               5                   10

<210> SEQ ID NO 15
<211> LENGTH: 12
<212> TYPE: PRT
<213> ORGANISM: Homo sapiens

<400> SEQUENCE: 15

Cys Ala Ala Trp Asp Gly Ser Leu Leu Gly Leu Val
1               5                   10

```
<210> SEQ ID NO 16
<211> LENGTH: 12
<212> TYPE: PRT
<213> ORGANISM: Homo sapiens

<400> SEQUENCE: 16

Cys Ala Ala Trp Asp Gly Thr Leu Thr Gly Leu Leu
1               5                   10

<210> SEQ ID NO 17
<211> LENGTH: 12
<212> TYPE: PRT
<213> ORGANISM: Homo sapiens

<400> SEQUENCE: 17

Cys Ala Ala Trp Asp Lys Ser Ile Ser Gly Leu Val
1               5                   10

<210> SEQ ID NO 18
<211> LENGTH: 12
<212> TYPE: PRT
<213> ORGANISM: Homo sapiens

<400> SEQUENCE: 18

Cys Ala Ala Trp Asp Gly Gly Leu Leu Gly Leu Val
1               5                   10

<210> SEQ ID NO 19
<211> LENGTH: 112
<212> TYPE: PRT
<213> ORGANISM: Artificial Sequence
<220> FEATURE:
<223> OTHER INFORMATION: Antibody Clone A4

<400> SEQUENCE: 19

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
            20                  25                  30

Tyr Lys Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Leu Val Phe Gly Gly Gly Thr Lys Leu Thr Val Leu Gly
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Antibody clone A5

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30
```

```
Tyr His Val Tyr Trp Tyr Gln Gln Leu Pro Gly Thr Ala Pro Lys Leu
            35                  40                  45

Leu Ile Tyr Gly Ser Ile Asn Arg Pro Ser Gly Val Pro Asp Arg Phe
 50                  55                  60

Ser Gly Ser Lys Ser Gly Thr Ser Gly Ser Leu Ala Ile Ser Gly Leu
 65                  70                  75                  80

Arg Ser Glu Asp Glu Ala Asp Tyr Tyr Cys Ala Ala Trp Asp Ser Ser
                 85                  90                  95

Ser Ser Gly Leu Val Phe Gly Gly Gly Thr Lys Leu Thr Val Leu Gly
                100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Antibody clone C4

<400> SEQUENCE: 21

Gln Ser Val Leu Thr Gln Pro Pro Ser Ala Ser Gly Thr Pro Gly Gln
 1               5                  10                  15

Arg Val Thr Ile Ser Cys Thr Gly Ser Thr Ser Asn Ile Gly Ala Gly
             20                  25                  30

Tyr Lys Val Tyr Trp Tyr Gln Gln Leu Pro Gly Thr Ala Pro Lys Leu
            35                  40                  45

Leu Ile Tyr Gly Asn Ile Asn Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Ser Gly Leu Val Phe Gly Gly Gly Thr Lys Leu Thr Val Leu Gly
                100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Antibody clone G4

<400> SEQUENCE: 22

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ala Gly
             20                  25                  30

Tyr Lys Val Tyr Trp Tyr Gln Gln Leu Pro Gly Thr Ala Pro Lys Leu
            35                  40                  45

Leu Ile Tyr Gly Asn Ile Asn Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Glu Ser
                 85                  90                  95

Ile Thr Gly Leu Val Phe Gly Gly Gly Thr Lys Leu Thr Val Leu Gly
                100                 105                 110

<210> SEQ ID NO 23
```

<211> LENGTH: 112
<212> TYPE: PRT
<213> ORGANISM: Artificial Sequence
<220> FEATURE:
<223> OTHER INFORMATION: Antibody clone F6

<400> SEQUENCE: 23

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Asp Val Tyr Trp Tyr Gln Gln Leu Pro Gly Thr Ala Pro Lys Leu
            35                  40                  45

Leu Ile Tyr Arg Asn Ile Asn Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Gly Ser
                85                  90                  95

Leu Leu Gly Leu Val Phe Gly Gly Gly Thr Lys Leu Thr Val Leu Gly
            100                 105                 110
```

<210> SEQ ID NO 24
<211> LENGTH: 112
<212> TYPE: PRT
<213> ORGANISM: Artificial Sequence
<220> FEATURE:
<223> OTHER INFORMATION: Antibody clone F9

<400> SEQUENCE: 24

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Gly Val Tyr Trp Tyr Gln Gln Leu Pro Gly Thr Ala Pro Lys Leu
            35                  40                  45

Leu Ile Tyr Gly Asn Ile Asn Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Gly Thr
                85                  90                  95

Leu Thr Gly Leu Leu Phe Gly Gly Gly Thr Lys Leu Thr Val Leu Gly
            100                 105                 110
```

<210> SEQ ID NO 25
<211> LENGTH: 112
<212> TYPE: PRT
<213> ORGANISM: Artificial Sequence
<220> FEATURE:
<223> OTHER INFORMATION: Antibody clone G12

<400> SEQUENCE: 25

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Asn Val Tyr Trp Tyr Gln Gln Leu Pro Gly Thr Ala Pro Lys Leu
            35                  40                  45
```

```
Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Lys Ser
                85                  90                  95

Ile Ser Gly Leu Val Phe Gly Gly Gly Thr Lys Leu Thr Val Leu Gly
            100                 105                 110
```

<210> SEQ ID NO 26
<211> LENGTH: 112
<212> TYPE: PRT
<213> ORGANISM: Artificial Sequence
<220> FEATURE:
<223> OTHER INFORMATION: Antibody clone H12

<400> SEQUENCE: 26

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asn Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Leu Val Phe Gly Gly Gly Thr Lys Leu Thr Val Leu Gly
            100                 105                 110
```

<210> SEQ ID NO 27
<211> LENGTH: 112
<212> TYPE: PRT
<213> ORGANISM: Artificial Sequence
<220> FEATURE:
<223> OTHER INFORMATION: Antibody clones B9 and H11

<400> SEQUENCE: 27

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asn Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Gly Gly
                85                  90                  95

Leu Leu Gly Leu Val Phe Gly Gly Gly Thr Lys Leu Thr Val Leu Gly
            100                 105                 110
```

<210> SEQ ID NO 28
<211> LENGTH: 10
<212> TYPE: PRT
<213> ORGANISM: Homo sapiens

<400> SEQUENCE: 28

Gly Phe Thr Phe Ser Thr Tyr Gly Met His
1               5                   10

<210> SEQ ID NO 29
<211> LENGTH: 26
<212> TYPE: PRT
<213> ORGANISM: Homo sapiens

<400> SEQUENCE: 29

Gly Lys Gly Leu Glu Trp Leu Ser Tyr Ile Ser Gly Gly Ser Ser Tyr
1               5                   10                  15

Ile Phe Tyr Ala Asp Ser Val Arg Gly Arg
            20                  25

<210> SEQ ID NO 30
<211> LENGTH: 13
<212> TYPE: PRT
<213> ORGANISM: Homo sapiens

<400> SEQUENCE: 30

Cys Ala Arg Ile Leu Arg Gly Gly Ser Gly Met Asp Leu
1               5                   10

<210> SEQ ID NO 31
<211> LENGTH: 119
<212> TYPE: PRT
<213> ORGANISM: Artificial Sequence
<220> FEATURE:
<223> OTHER INFORMATION: Antibody clone A4

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Antibody clone A5

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr

-continued

```
                20                  25                  30
Gly Met His Trp Val Arg Gln Ala Pro Gly Lys Gly Leu Glu Trp Leu
            35                  40                  45

Ser Tyr Ile Ser Gly Gly Ser Ser Tyr Ile Phe Tyr Ala Asp Ser Val
        50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 33
<211> LENGTH: 119
<212> TYPE: PRT
<213> ORGANISM: Artificial Sequence
<220> FEATURE:
<223> OTHER INFORMATION: Antibody clone C4

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
            35                  40                  45

Ser Tyr Ile Ser Gly Gly Ser Ser Tyr Ile Phe Tyr Ala Asp Thr Val
        50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 34
<211> LENGTH: 119
<212> TYPE: PRT
<213> ORGANISM: Artificial Sequence
<220> FEATURE:
<223> OTHER INFORMATION: Antibody clone G4

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
            35                  40                  45

Ser Tyr Ile Ser Gly Gly Ser Ser Tyr Ile Phe Tyr Ala Asp Ser Val
        50                  55                  60

Arg Gly Arg Phe Thr Ile Ser Arg Asp Asn Ser Glu Asn Ala Leu Tyr
65                  70                  75                  80
```

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 35
<211> LENGTH: 119
<212> TYPE: PRT
<213> ORGANISM: Artificial Sequence
<220> FEATURE:
<223> OTHER INFORMATION: Antibody clone F6

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 36
<211> LENGTH: 119
<212> TYPE: PRT
<213> ORGANISM: Artificial Sequence
<220> FEATURE:
<223> OTHER INFORMATION: Antibody clone F9

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 37

```
<211> LENGTH: 119
<212> TYPE: PRT
<213> ORGANISM: Artificial Sequence
<220> FEATURE:
<223> OTHER INFORMATION: Antibody clone G12

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 38
<211> LENGTH: 119
<212> TYPE: PRT
<213> ORGANISM: Artificial Sequence
<220> FEATURE:
<223> OTHER INFORMATION: Antibody clone H12

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 39
<211> LENGTH: 119
<212> TYPE: PRT
<213> ORGANISM: Artificial Sequence
<220> FEATURE:
<223> OTHER INFORMATION: Antibody clones B9 and H11

<400> SEQUENCE: 39

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 40
<211> LENGTH: 336
<212> TYPE: DNA
<213> ORGANISM: Artificial Sequence
<220> FEATURE:
<223> OTHER INFORMATION: Antibody Clone A4

<400> SEQUENCE: 40
cagtctgtgc tgactcagcc accctcagcg tctgggaccc ccgggcagag ggtcaccatc    60
tcttgcactg ggagcagctc caacatcggg gcaggttata atgtatactg gtatcagcag   120
ctcccaggaa cggcccccaa actcctcatc tatggtaaca tcaatcggcc ctcaggggtc   180
cctgaccgat tctctggctc caagtctggc acctcagcct ccctggccat cagtgggctc   240
cggtccgagg atgaggctga ttattactgt gcagcatggg atgacagcct gagtggtctg   300
gttttcggcg gaggaaccaa gctgacggtc ctaggt                             336

<210> SEQ ID NO 41
<211> LENGTH: 336
<212> TYPE: DNA
<213> ORGANISM: Artificial Sequence
<220> FEATURE:
<223> OTHER INFORMATION: Antibody clone A5

<400> SEQUENCE: 41
cagtctgtgc tgactcagcc accctcagcg tctgggaccc ccgggcagag ggtcaccatc    60
tcttgcactg ggagcagctc caacatcggg gcaggttata atgtatactg gtatcagcag   120
ctcccaggaa cggcccccaa actcctcatc tatggtaaca tcaatcggcc ctcaggggtc   180
cctgaccgat tctctggctc caagtctggc acctcagcct ccctggccat cagtgggctc   240
cggtccgagg atgaggctga ttattactgt gcagcatggg atgacagcct gagtggtctg   300
gttttcggcg gaggaaccaa gctgacggtc ctaggt                             336

<210> SEQ ID NO 42
<211> LENGTH: 336
<212> TYPE: DNA
<213> ORGANISM: Artificial Sequence
<220> FEATURE:
<223> OTHER INFORMATION: Antibody clone G4

<400> SEQUENCE: 42
cagtctgtgc tgactcagcc accctcagcg tctgggaccc ccgggcagag ggtcaccatc    60
tcttgcactg ggagcagctc caacatcggg gcaggttata atgtatactg gtatcagcag   120

```
ctcccaggaa cggcccccaa actcctcatc tatggtaaca tcaatcggcc ctcaggggtc    180
cctgaccgat tctctggctc caagtctggc acctcagcct ccctggccat cagtgggctc    240
cggtccgagg atgaggctga ttattactgt gcagcatggg atgacagcct gagtggtctg    300
gttttcggcg aggaaccaa gctgacggtc ctaggt                               336

<210> SEQ ID NO 43
<211> LENGTH: 336
<212> TYPE: DNA
<213> ORGANISM: Artificial Sequence
<220> FEATURE:
<223> OTHER INFORMATION: Antibody clone F6

<400> SEQUENCE: 43
cagtctgtgc tgactcagcc accctcagcg tctgggaccc ccgggcagag ggtcaccatc    60
tcttgcactg ggagcagctc caacatcggg gcaggttatg atgtatactg gtatcagcag   120
ctcccaggaa cggcccccaa actcctcatc tatcgtaaca tcaatcggcc ctcaggggtc   180
cctgaccgat tctctggctc caagtctggc acctcagcct ccctggccat cagtgggctc   240
cggtccgagg atgaggctga ttattactgt gcagcatggg atgcagcct gctgggtctg    300 gttttcggcg aggaaccaa gctgacggtc ctgggt                              336

<210> SEQ ID NO 44
<211> LENGTH: 336
<212> TYPE: DNA
<213> ORGANISM: Artificial Sequence
<220> FEATURE:
<223> OTHER INFORMATION: Antibody clone F9

<400> SEQUENCE: 44
cagtctgtgc tgactcagcc accctcagcg tctgggaccc ccgggcagag ggtcaccatc    60
tcttgcactg ggagcagctc caacatcggg gcaggttatg gtgtatactg gtatcagcag   120
ctcccaggaa cggcccccaa actcctcatc tatggtaaca tcaatcggcc ctcaggggtc   180
cctgaccgat tctctggctc caagtctggc acctcagctt ccctggccat cagtgggctc   240
cggtccgagg atgaggctga ttattactgt gcagcatggg atgcaccct gaccggtctg    300 ctgttcggcg aggaaccaa gctgacggtc ctaggt                              336

<210> SEQ ID NO 45
<211> LENGTH: 336
<212> TYPE: DNA
<213> ORGANISM: Artificial Sequence
<220> FEATURE:
<223> OTHER INFORMATION: Antibody clone G12

<400> SEQUENCE: 45
cagtctgtgc tgactcagcc accctcagcg tctgggaccc ccgggcagag ggtcaccatc    60
tcttgcactg ggagcagctc caacatcggg gcgggttaca atgtatactg gtatcagcag   120
ctcccaggaa cggcccccaa actcctcatc tatggtaaca tcaatcggcc ctcaggggtc   180
cctgaccgat tctctggctc caagtctggc acctcagcct ccctggccat cagtgggctc   240
cggtccgagg atgaggctga ttattactgt gcagcatggg ataagagcat ttctggtctg    300
gttttcggcg aggaaccaa gctgacggtc ctaggt                              336

<210> SEQ ID NO 46
<211> LENGTH: 744
<212> TYPE: DNA
<213> ORGANISM: Artificial Sequence
```

<220> FEATURE:
<223> OTHER INFORMATION: Antibody clone H12

<400> SEQUENCE: 46

| | |
|---|---|
| cagtctgtgc tgactcagcc accctcagcg tctgggaccc ccgggcagag ggtcaccatc | 60 |
| tcttgcactg ggagcagctc caacatcggg gcaggttata atgtatactg gtatcagcag | 120 |
| ctcccaggaa cggcccccaa actcctcatc tatggtaaca tcaatcggcc ctcaggggtc | 180 |
| cctgaccgat tctctggctc caagtctggc acctcagcct ccctggccat cagtgggctc | 240 |
| cggtccgagg atgaggctga ttattactgt gcagcatggg atgacagcct gagtggtctg | 300 |
| gttttcggcg gaggaaccaa gctgacggtc ctaggtgagt agaacgtacg ctagcaagct | 360 |
| tggatccacg atcctgagca aggacctctg ccctccctgt tcagacccct gcttgcctca | 420 |
| gcaggtcatt acaaccactt cacctctgac cgcaggggca gggactaga tagaatgacc | 480 |
| tactgagcct cgtctgtctg tctgtctgtc tctctgtttg tctgtctgtc tctctgtttg | 540 |
| tctctctgtc tgtctgacag gcgcaggctg ggtctctaag ccttgttctg ttctggcctc | 600 |
| ctcagtctgg gttcttgtcg gaacagcttt gcccttgggt tacctgggtt ccatctcctg | 660 |
| gggaattggg aacaaggggt ctgagggagg cacctcctgg gagactttag aaggacccag | 720 |
| tgccctcggg gctgatgctc ggga | 744 |

<210> SEQ ID NO 47
<211> LENGTH: 336
<212> TYPE: DNA
<213> ORGANISM: Artificial Sequence
<220> FEATURE:
<223> OTHER INFORMATION: Antibody clones B9 and H11

<400> SEQUENCE: 47

| | |
|---|---|
| cagtctgtgc tgactcagcc accctcagcg tctgggaccc ccgggcagag ggtcaccatc | 60 |
| tcttgcactg ggagcagctc caacatcggg gcaggttata atgtatactg gtatcagcag | 120 |
| ctcccaggaa cagcccccaa actcctcatc tatggtaaca tcaatcggcc ctcaggggtc | 180 |
| cctgaccgat tctctggctc caagtctggc acctcagcct ccctggccat cagtgggctc | 240 |
| cggtccgagg atgaggctga ttattactgt gcagcatggg atggcggcct gctgggtctg | 300 |
| gttttcggcg gaggaaccaa gctgacggtc ctaggt | 336 |

<210> SEQ ID NO 48
<211> LENGTH: 336
<212> TYPE: DNA
<213> ORGANISM: Artificial Sequence
<220> FEATURE:
<223> OTHER INFORMATION: Antibody clone C4

<400> SEQUENCE: 48

| | |
|---|---|
| cagtctgtgc tgactcagcc accctcagcg tctgggaccc ccgggcagag ggtcaccatc | 60 |
| tcttgcactg ggagcacctc caacatcggg gcaggttaca aagtatattg gtatcagcag | 120 |
| ctcccaggaa cggcccccaa actcctcatc tatggtaaca tcaatcggcc ctcaggggtc | 180 |
| cctgaccgat tctctggctc caagtctggc acctcagcct ccctggccat cagtgggctc | 240 |
| cggtccgagg atgaggctga ttattactgt gcagcatggg atgacagcct gagtggtctg | 300 |
| gttttcggcg gaggaaccaa gctgacggtc ctaggt | 336 |

<210> SEQ ID NO 49
<211> LENGTH: 357
<212> TYPE: DNA

```
<213> ORGANISM: Artificial Sequence
<220> FEATURE:
<223> OTHER INFORMATION: Antibody clone A4

<400> SEQUENCE: 49
gaggtgcagc tgttggagtc tggggggaggc ttggtacagc ctgggggggtc cctgagactc      60 tcctgtgcag cctctggatt caccttcagt acttatggca tgcactgggt ccgccaggct     120
ccagggaagg ggctggagtg gctttcatat attagtggtg gtagtagtta cattttctac     180
gcagactcag tgaggggccg attcaccatc tccagagaca actccgagaa cgcgctgtat     240
ctgcaaatga acagcctgag agccgaggac acggccgtgt attactgtgc gagaatatta     300
agaggcggga gcggtatgga cctctggggc caaggtacac tggtcaccgt gagctca        357

<210> SEQ ID NO 50
<211> LENGTH: 357
<212> TYPE: DNA
<213> ORGANISM: Artificial Sequence
<220> FEATURE:
<223> OTHER INFORMATION: Antibody clone A5

<400> SEQUENCE: 50
gaggtgcagc tgttggagtc tggggggaggc ttggtacagc ctgggggggtc cctgagactc      60 tcctgtgcag cctctggatt caccttcagt acttatggca tgcactgggt ccgccaggct     120
ccagggaagg ggctggagtg gctttcatat attagtggtg gtagtagtta cattttctac     180
gcagactcag tgaggggccg attcaccatc tccagagaca actccgagaa cgcgctgtat     240
ctgcaaatga acagcctgag agccgaggac acggccgtgt attactgtgc gagaatatta     300
agaggcggga gcggtatgga cctctggggc caaggtacac tggtcaccgt gagctca        357

<210> SEQ ID NO 51
<211> LENGTH: 357
<212> TYPE: DNA
<213> ORGANISM: Artificial Sequence
<220> FEATURE:
<223> OTHER INFORMATION: Antibody clone C4

<400> SEQUENCE: 51
gaggtgcagc tgttggagtc tggggggaggc ttggtacagc ctgggggggtc cctgagactc      60 tcctgtgcag cctctggatt caccttcagt acttatggca tgcactgggt ccgccaggct     120
ccagggaagg ggctggagtg gctttcatat attagtggtg gtagtagtta cattttctac     180
gcagacacag tgaggggccg attcactatc tccagagaca actccgagaa cgcactgtat     240
ctgcaaatga acagcctgag agccgaggac acggccgtgt attactgtgc gagaatatta     300
agagggggga gcggtatgga cctctggggc caaggtacac tggtcaccgt gagctca        357

<210> SEQ ID NO 52
<211> LENGTH: 357
<212> TYPE: DNA
<213> ORGANISM: Artificial Sequence
<220> FEATURE:
<223> OTHER INFORMATION: Antibody clone G4

<400> SEQUENCE: 52
gaggtgcagc tgttggagtc tggggggaggc ttggtacagc ctgggggggtc cctgagactc      60 tcctgtgcag cctctggatt caccttcagt acttatggca tgcactgggt ccgccaggct     120
ccagggaagg ggctggagtg gctttcatat attagtggtg gtagtagtta cattttctac     180
gcagactcag tgaggggccg attcaccatc tccagagaca actccgagaa cgcgctgtat     240
```
ctgcaaatga acagcctgag agccgaggac acggccgtgt attactgtgc gagaatatta    300
agaggcggga gcggtatgga cctctggggc caaggtacac tggtcaccgt gagctca      357

<210> SEQ ID NO 53
<211> LENGTH: 357
<212> TYPE: DNA
<213> ORGANISM: Artificial Sequence
<220> FEATURE:
<223> OTHER INFORMATION: Antibody clone F6

<400> SEQUENCE: 53
gaggtgcagc tgttggagtc tgggggaggc ttggtacagc ctgggggtc cctgagactc     60 tcctgtgcag cctctggatt caccttcagt acttatggca tgcactgggt tcgccaggct   120
ccagggaagg ggctggagtg ctttcatat attagtggtg gtagtagtta cattttctac    180
gcagactcag tgaggggccg attcaccatc tccagagaca actccgagaa cgcgctgtat   240
ctgcaaatga acagcctgag agccgaggac acggccgtgt attactgtgc gagaatatta   300
agaggcggga gcggtatgga cctctggggc caaggtacac tggtcaccgt gagctca      357

<210> SEQ ID NO 54
<211> LENGTH: 357
<212> TYPE: DNA
<213> ORGANISM: Artificial Sequence
<220> FEATURE:
<223> OTHER INFORMATION: Antibody clone F9

<400> SEQUENCE: 54
gaggtgcagc tgttggagtc tgggggaggc ttggtacagc ctgggggtc cctgagactc     60 tcctgtgcag cctctggatt caccttcagt acttatggca tgcactgggt ccgccaggct   120
ccagggaagg ggctggagtg ctttcatat attagtggtg gtagtagtta cattttctac    180
gcagactcag tgaggggccg attcaccatc tccagagaca actccgagaa cgcgctgtat   240
ctgcaaatga acagcctgag agccgaggac acggccgtgt attactgtgc gagaatatta   300
agaggcggga gcggtatgga cctctggggc caaggtacac tggtcaccgt gagctca      357

<210> SEQ ID NO 55
<211> LENGTH: 357
<212> TYPE: DNA
<213> ORGANISM: Artificial Sequence
<220> FEATURE:
<223> OTHER INFORMATION: Antibody clone G12

<400> SEQUENCE: 55
gaggtgcagc tgttggagtc tgggggaggc ttggtacagc ctgggggtc cctgagactc     60 tcctgtgcag cctctggatt caccttcagt acttatggca tgcactgggt ccgccaggct   120
ccagggaagg ggctggagtg ctttcatat attagtggtg gtagtagtta cattttctac    180
gcagactcag tgaggggccg attcaccatc tccagagaca actccgagaa cgcgctgtat   240
ctgcaaatga acagcctgag agccgaggac acggccgtgt attactgtgc gagaatatta   300
agaggcggga gcggtatgga cctctggggc caaggtacac tggtcaccgt gagctca      357

<210> SEQ ID NO 56
<211> LENGTH: 774
<212> TYPE: DNA
<213> ORGANISM: Artificial Sequence
<220> FEATURE:
<223> OTHER INFORMATION: Antibody clone H12

<400> SEQUENCE: 56

```
gaggtgcagc tgttggagtc tgggggaggc ttggtacagc ctgggggtc cctgagactc      60
tcctgtgcag cctctggatt caccttcagt acttatggca tgcactgggt ccgccaggct    120
ccagggaagg ggctggagtg gctttcatat attagtggtg gtagtagtta cattttctac    180
gcagactcag tgaggggccg attcaccatc tccagagaca actccgagaa cgcgctgtat    240
ctgcaaatga acagcctgag agccgaggac acggccgtgt attactgtgc gagaatatta    300
agaggcggga gcggtatgga cctctggggc caaggtacac tggtcaccgt gagctcaggt    360
gagtcgtacg ctagcaagct ttctggggca ggccaggcct gaccttggct ttggggcagg    420
gagggggcta aggtgaggca ggtggcgcca gccaggtgca cacccaatgc ccatgagccc    480
agacactgga cgctgaacct cgcggacagt taagaaccca ggggcctctg cgccctgggc    540
ccagctctgt cccacaccgc ggtcacatgg caccacctct cttgcagcct ccaccaaggg    600
cccatcggtc ttcccctgg caccctcctc caagagcacc tctgggggca gcggccct      660
gggctgcctg gtcaaggact acttccccga accggtgacg gtgtcgtgga actcaggcgc    720
cctgaccagc ggcgtgcaca ccttcccggc tgtcctacag tcctcacgac tcta          774
```

<210> SEQ ID NO 57
<211> LENGTH: 420
<212> TYPE: DNA
<213> ORGANISM: Artificial Sequence
<220> FEATURE:
<223> OTHER INFORMATION: Antibody clones B9 and H11

<400> SEQUENCE: 57

```
gaggtgcagc tgttggagtc tgggggaggc ttggtacagc ctgggggtc cctgagactc      60
tcctgtgcag cctctggatt caccttcagt acttatggca tgcactgggt ccgccaggct    120
ccagggaagg ggctggagtg gctttcatat attagtggtg gtagtagtta cattttctac    180
gcagactcag tgaggggccg attcaccatc tccagagaca actccgagaa cgcgctgtat    240
ctgcaaatga acagcctgag agccgaggac acggccgtgt attactgtgc gagaatatta    300
agaggcggga gcggtatgga cctctggggc caaggtacac tggtcaccgt gagctcaggt    360
gagtcgtacg ctagcaagct ttctggggca ggccaggcct gaccttggct ttggggcagg    420
```

<210> SEQ ID NO 58
<211> LENGTH: 112
<212> TYPE: PRT
<213> ORGANISM: Artificial Sequence
<220> FEATURE:
<223> OTHER INFORMATION: Antibody B44

<400> SEQUENCE: 58

```
Gln Ser Val Leu Thr Gln Pro Pro Ser Ala Ser Gly Thr Pro Gly Gln
 1               5                  10                  15
Arg Val Thr Ile Ser Cys Thr Gly Ser Ser Ser Asn Ile Gly Ala Gly
                20                  25                  30
Tyr Asp Val Tyr Trp Tyr Gln Gln Leu Pro Gly Thr Ala Pro Lys Leu
            35                  40                  45
Leu Ile Tyr Gly Asn Ile Asn Arg Pro Ser Gly Val Pro Asp Arg Phe
        50                  55                  60
Ser Gly Ser Lys Ser Gly Thr Ser Ala Ser Leu Ala Ile Ser Gly Leu
 65                 70                  75                  80
Arg Ser Glu Asp Glu Ala Asp Tyr Tyr Cys Ala Ala Trp Asp Asp Ser
                85                  90                  95
```

Leu Ser Gly Leu Val Phe Gly Gly Gly Thr Lys Leu Thr Val Leu Gly
            100                 105                 110

<210> SEQ ID NO 59
<211> LENGTH: 336
<212> TYPE: DNA
<213> ORGANISM: Artificial Sequence
<220> FEATURE:
<223> OTHER INFORMATION: Antibody B44

<400> SEQUENCE: 59
cagtctgtgc tgactcagcc accctcagcg tctgggaccc ccgggcagag ggtcaccatc    60
tcttgcactg ggagcagctc caacatcggg gcaggttata atgtatactg gtatcagcag   120
ctcccaggaa cggcccccaa actcctcatc tatggtaaca tcaatcggcc ctcaggggtc   180
cctgaccgat tctctggctc caagtctggc acctcagcct ccctggccat cagtgggctc   240
cggtccgagg atgaggctga ttattactgt gcagcatggg atgacagcct gagtggtctg   300
gttttcggcg gaggaaccaa gctgacggtc ctaggt                             336

<210> SEQ ID NO 60
<211> LENGTH: 119
<212> TYPE: PRT
<213> ORGANISM: Artificial Sequence
<220> FEATURE:
<223> OTHER INFORMATION: Antibody B44

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 61
<211> LENGTH: 357
<212> TYPE: DNA
<213> ORGANISM: Artificial Sequence
<220> FEATURE:
<223> OTHER INFORMATION: Antibody B44

<400> SEQUENCE: 61
gaggtgcagc tgttggagtc tgggggaggc ttggtacagc ctggggggtc cctgagactc    60
tcctgtgcag cctctggatt caccttcagt acttatggca tgcactgggt ccgccaggct   120
ccagggaagg ggctggagtg gctttcatat attagtggtg gtagtagtta catttttctac   180 gcagactcag tgaggggccg attcaccatc tccagagaca actccgagaa cgcgctgtat   240
ctgcaaatga acagcctgag agccgaggac acggccgtgt attactgtgc gagaatatta   300
agaggcggga gcggtatgga cctctggggc caaggtacac tggtcaccgt gagctca    357

<210> SEQ ID NO 62
<211> LENGTH: 330
<212> TYPE: PRT
<213> ORGANISM: Homo sapiens

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 63
<211> LENGTH: 105
<212> TYPE: PRT
<213> ORGANISM: Homo sapiens

<400> SEQUENCE: 63

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 64
<211> LENGTH: 119
<212> TYPE: PRT
<213> ORGANISM: Artificial Sequence
<220> FEATURE:
<223> OTHER INFORMATION: Exemplary framework mutations

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 65
<211> LENGTH: 357
<212> TYPE: DNA
<213> ORGANISM: Artificial Sequence
<220> FEATURE:
<223> OTHER INFORMATION: Exemplary framework mutations

<400> SEQUENCE: 65
gaggtgcagc tgttggagtc tgggggaggc ttggtacagc ctgggggggtc cctgagactc        60 tcctgtgcag cctctggatt caccttcagt acttatggca tgcactgggt ccgccaggct       120
ccagggaagg ggctggagtg gctttcatat attagtggtg gtagtagtta catttttctac      180 gcagactcag tgaggggccg attcaccatc tccagagaca actccgagaa cacgctgtat       240
ctgcaaatga acagcctgag agccgaggac acggccgtgt attactgtgc gagaatatta       300
agaggcggga gcggtatgga cctctggggc caaggtacac tggtcaccgt gagctca          357

```
<210> SEQ ID NO 66
<211> LENGTH: 119
<212> TYPE: PRT
<213> ORGANISM: Artificial Sequence
<220> FEATURE:
<223> OTHER INFORMATION: Exemplary framework mutations

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 67
<211> LENGTH: 357
<212> TYPE: DNA
<213> ORGANISM: Artificial Sequence
<220> FEATURE:
<223> OTHER INFORMATION: Exemplary framework mutations

<400> SEQUENCE: 67
gaggtgcagc tgttggagtc tgggggaggc ttggtacagc ctgggggtc  cctgagactc      60 tcctgtgcag cctctggatt caccttcagt acttatggca tgcactgggt ccgccaggct     120
ccagggaagg ggctggagtg gctttcatat attagtggtg gtagtagtta catttttctac    180 gcagactcag tgaggggccg attcaccatc tccagagaca actccaagaa cacgctgtat     240
ctgcaaatga acagcctgag agccgaggac acggccgtgt attactgtgc gagaatatta    300
agaggcggga gcggtatgga cctctggggc caaggtacac tggtcaccgt gagctca        357
```

ANTI-CD40 ANTIBODIES AND METHODS OF TREATING CANCER HAVING CD40+ TUMOR CELLS

This application is a divisional application of U.S. patent application Ser. No. 14/342,141, filed Jun. 13, 2014, which is a § 371 application of PCT/GB2012/052179, filed Sep. 5, 2012, which in turn claims priority to GB Application 1115280.8, filed Sep. 5, 2011. The entire disclosure of each of the foregoing applications is incorporated by reference herein.

Incorporated herein by reference in its entirety is the Sequence Listing being concurrently submitted via EFS-Web as an ASCII text file named SequenceListing.txt, created May 5, 2017, and having a size of 45,975 bytes.

FIELD OF THE INVENTION

The present invention relates to antibody-based polypeptides with binding specificity for CD40 exhibiting improved affinity and/or agonist potency, which have utility in the treatment of diseases such as cancer. The invention also relates to pharmaceutical compositions, uses, methods and kits comprising such antibodies.

Introduction

Cancer accounts for over 30% of deaths in developed countries. Whilst great progress has been achieved in the treatment of certain tumours (Hodgkin's disease, some lymphomas/leukaemias, localized cutaneous cancer), conventional therapies such as surgery, chemotherapy, and radiotherapy are often ineffective in curing disseminated solid tumours.

Immunotherapy (synonymous with biological therapy) of cancer holds great promise for treatment of several different types of cancer, including disseminated metastatic tumours (Stagg et al., 2007, *Immunol Rev.* 220:82-101; Melief, 2008, *Immunity*, 29:372-383, Melero et al., 2007, *Nat Rev Cancer*, 7:95-106; Waldmann, 2006, *Annu. Rev Med.* 57:65-81; Khawli et al., 2008, *Handb. Exp. Pharmacol.* 181:291-328; Berinstein, 2007, *Vaccine*, 25 Suppl 2: B72-B88; Mellor & Munn, 2008, *Nat Rev Immunol.* 8:74-80). It aims at recruiting the patient's own immune system to fight the cancer and generate a long term eradication of the tumour cells.

Several different approaches to cancer immunotherapy have been developed, including the following:
(1) Monoclonal antibody (Mab) therapy can be used to: i) target cancer cells for destruction, either using the antibodies naked or conjugated to a toxin (e.g. Rituximab); and/or ii) block growth factor receptors (e.g. Herceptin); and/or or iii) stimulate the immune system.
(2) Cancer vaccines, which includes tumour cell vaccines (autologous or allogeneic), antigenic vaccines and dendritic cells (DCs) vaccine, DNA vaccines, and vector-based vaccines (e.g. adenovirus-based gene transfer).
(3) Non-specific immunotherapies and adjuvants, which act by stimulating the immune system more generally and thereby activate tumour-specific immune cells that have been suppressed by the tumour environment. This may be done either by stimulating or activating immune effector cells giving an immune reaction to the tumour (e.g. effector T cells, or $T_{eff}$ cells) or by inhibiting or inactivating cells with an inhibitory phenotype (e.g. regulatory T cells, or $T_{reg}$ cells). An approach like this will include active molecules like cytokines, bacterial adjuvants as well as drugs (including mAbs) that target immuno-regulatory receptors (e.g. CTLA-4 and CD40). Additional approaches include adoptive T cell transfer and $T_{reg}$ depletion therapies, which fall somewhere between the two latter groups.

CD40 is a cell-surface expressed glycoprotein that belongs to the tumour necrosis factor receptor (TNFR) superfamily and plays a central role in the immune system. It is expressed on a variety of immune cells, such as B cells, dendritic cells, monocytes, and macrophages. Professional antigen-presenting cells (APCs), are activated when signalling via CD40 occurs (reviewed by Schonbeck and Libby, 2001, *Cell Mol Life Sci*, 58(1):4-43).

The natural ligand of CD40, designated CD154 or CD40L, is mainly expressed on mature T lymphocytes (Armitage et al., 1992, *Nature*, 357: 80-82; Schonbeck et al., 2001, *Cell Mol Life Sci.*, 58,40-43; van Kooten et al., 2000, *J. Leuk. Biol.*, 67: 2-17; Quezada et al., 2004, *Annu. Rev. Immunol.*, 22:3077-328). CD40L-mediated signalling triggers several biological events, including immune cell activation, proliferation, and production of cytokines and chemokines (Schonbeck et al., 2001, *Cell Mol Life Sci.*, 58:40-43; van Kooten et al., 2000, *J. Leuk., Biol.*, 67: 2-17).

CD40 signalling is critical for T cell-dependent and B cell-dependent immune responses, and patients with non-functional CD40 or CD40L are markedly immune suppressed (Foy et al., 1993, *J Exp Med* 5:1567-1575; Siepmann et al., 2001, *Immunology* 3:263-272; Allen et al., 1993, *Science*, 259:990-993). Stimulation of antigen presenting cells, such as human B cells and dendritic cells with recombinant CD40L or anti-CD40 antibodies induces up-regulation of surface markers, such as CD23, CD80, CD86, Fas and MHC II, and secretion of soluble cytokines, e.g. IL-12, TNF-γ and TNF-α (van Kooten et al., 2000, J Leucoc Biol, 67:2-17; Schonbeck et al., 2001, supra). In a tumour setting, CD40 stimulated dendritic cells can activate tumour specific effector T cells, which have the potential to eradicate tumour cells ((van Kooten et al., 2000, J Leucoc Biol, 67:2-17; Sotomayor et al., 1999, *Nature Medicine*, 5:780-787).

CD40 expression occurs in many normal cells and in tumour cells. For example, all B-lymphomas and 30% to 70% of solid tumours have CD40 expression. Melanomas and carcinomas belong to the tumours having CD40 expression. It is well established that activation of CD40 is effective in triggering anti-tumour responses (Tong et al., 2003, *Cancer Gene Therapy*, 10(1):1-13; Ottalano et al., 2002, *Tumori*, 88 (5):361-6). The effect of CD40 activation, contributing to tumour growth impairment, involves at least mechanisms of, immune activation producing a tumour-specific T cell response, a direct apoptotic effect on CD40-positive tumours and stimulating a humoral response leading to ADCC. Anti-tumour effect by CD40-activation have also been reported on CD40-negative tumours (Tutt et al., 2002, *J Immunol.*, 168 (6):2720-8; van Mierlo et al., 2002, *Proc Natl Acad Sci, USA*, 99(8):5561-6). Here, the observed tumour eradication was strongly connected to the emergence of CTLs, tumour-specific cytotoxic T lymphocytes.

Cancer vaccine adjuvants, involving CD40 stimulation, have been proposed. Pre-clinical proof-of-concept has been demonstrated for agonistic CD40 antibodies for several cancer forms (Kalbashi et al., 2010, *J Immunotherapy*, 33:810-816; Loskog et al., 2009, *Semin Immunology*, 21:301-307; French et al., 1999, *Nature Medicine*, 548-553; Sotomayor et al., 1999, *Nature Medicine*, 5:780-787; Staveley et al., 2003, *Nature Medicine*, 171:697-707). Clinical trials have also been conducted for agonistic CD40 antibodies, including SGN-40 (a humanized antibody having partial and weak agonistic properties) and CP-870,893 (a fully human and selective CD40 agonistic monoclonal antibody)

(Khalil and Vonderheide, 2007, *Update on Cancer Therapeutics*, 2:61-65; Hussein et al., 2010, *Haematologica*, 95:845-848).

However, the systemic administration of CD40-antibodies has been associated with adverse side effects, such as shock syndrome, and cytokine release syndrome (van Mierlo et al., 2002, *Proc. Natl. Acad. Sci. USA*, 99:5561-5566; van Mierlo et al., 2004, *J Immunol* 173:6753-6759).

In light of the above, there remains a need for improved anti-tumour therapies, particularly anti-CD40 agonist antibodies suitable for clinical use.

SUMMARY OF THE INVENTION

In a first aspect, the invention provides an antibody or an antigen-binding fragment thereof with multivalent binding specificity for CD40, or a variant, fusion or derivative of said antibody or antigen-binding fragment, or a fusion of a said variant or derivative thereof, which retains the multivalent binding specificity for CD40, wherein the potency of the antibody, antigen-binding fragment, or fusion, variant or derivative thereof, for dendritic cell activation is higher than, or is equal to, its potency for B cell activation and wherein the antibody, antigen-binding fragment, or fusion, variant or derivative thereof has an affinity (KD) for CD40 of less than $1\times10^{-10}$ M (i.e. 0.1 nM).

Alternatively, or in addition, the first aspect of the invention provides an antibody or an antigen-binding fragment thereof with multivalent binding specificity for CD40, or a variant, fusion or derivative of said antibody or antigen-binding fragment, or a fusion of a said variant or derivative thereof, which retains the multivalent binding specificity for CD40, wherein the antibody, antigen-binding fragment, or fusion, variant or derivative thereof is capable of exerting dual cytotoxic effects on CD40+ tumour cells (preferably in vivo). By "dual cytotoxic effects" we include a direct apoptotic effect on the tumour cells and an indirect immune cell-mediated cytotoxic (e.g. ADCC) effect on the tumour cells.

By "potency", with respect to dendritic cell activation and B cell activation, we mean the EC50 for such cell activation by the antibody, antigen-binding fragment, or fusion, variant or derivative thereof. It will be appreciated by persons skilled in the art that potency for dendritic cell activation and B cell activation may be measured by different methods, including but lot limited to those methods described in the Examples below.

In one embodiment, dendritic cell activation is defined by reference to an EC50 for the stimulation of expression of CD80 measured by FACS analysis (such as in Example 4) and B cell activation is defined by reference to an EC50 for the proliferation B cells (such as in Example 6).

It is known that the anti-CD40 antibody developed by Pfizer, CP-870,893, has an approximately 20-fold higher potency for B cell activation than for activation of dendritic cells (Gladue et al., 2011, *Cancer Immunol Immunotherapy* (7), 1009-1017). It has also been demonstrated that one of the major pharmacodynamic effects of treatment with CP-870,893 is a rapid decrease in the percentage of B cells among the peripheral blood lymphocytes (Vonderheide et al., 2007, *Journal of Clinical Oncology* 25, 7, 876-883). The effect on B cells may result in dose-limiting toxicity at a treatment dose which is insufficient to activate Dendritic cells. The present inventors believe that the activation of dendritic cells is of greater clinical relevance than B-cell activation. CD40 agonist therapy of cancer is firmly linked to T-cell activation (French et al., 1999, *Nature Medicine*, 548-553; van Kooten et al., 2000, J Leucoc Biol, 67:2-17; Sotomayor et al., 1999, *Nature Medicine*, 5:780-787), and this T-cell activation depends on activation of professional antigen presenting cells, in particular dendritic cells (Melief et al., 2000, 75: 235-282).

The present inventors have developed agonistic anti-CD40 antibody clones which have an improved ability to activate dendritic cells.

In one embodiment, the antibodies, antigen-binding fragments, variants, fusions and derivatives thereof, of the invention have a potency for dendritic cell activation which is higher than, or equal to, their potency for B cell activation. Or, put another way, the antibodies, antigen-binding fragments, variants, fusions and derivatives thereof, of the invention have a potency for B cell activation which is lower than, or is equal to, their dendritic cell activation which is higher than, or is equal to, its potency for dendritic cell activation.

By "binding specificity" we include the ability of the antibody, antigen-binding fragment, variant, fusion or derivative thereof, of the invention to bind at least 10-fold more strongly to CD40 than to any other polypeptide; preferably at least 50-fold more strongly and more preferably at least 100-fold more strongly. Preferably, the antibody, antigen-binding fragment, variant, fusion or derivative thereof, of the invention binds selectively to CD40 under physiological conditions (for example, in vivo; and for example, when CD40 is present on the cell surface).

By "multivalent" we include that the antibody, antigen-binding fragment, variant, fusion or derivative thereof, of the invention comprises two or more antigen binding sites with binding specificity for CD40. For example, the antibody may comprise two or three or four or five or six or more such antigen binding sites. In one embodiment, the antibody is an intact, bivalent IgG antibody.

CD40 is a cell-surface expressed glycoprotein that belongs to the tumour necrosis factor receptor (TNFR) superfamily and plays a central role in the immune system. It is expressed on a variety of immune cells, such as B cells, Dendritic cells, monocytes, and macrophages, and professional APCs, are activated when signalling via CD40 occurs (reviewed by Tasci et al., 2001, Cell. Mol. Life Sci., (58), 4-43). CD40 expression occurs in many normal cells and tumour cells, such as B-lymphomas, solid tumours, melanomas and carcinomas. It is well-established that activation of CD40 is effective in triggering anti-tumour responses, and CD40 activation contributes to tumour growth impairment by at least the mechanisms of immune activation, a direct apoptotic effect on CD40-positive tumours and stimulation of a humoral response leading to ADCC and CDC.

The occurrence of ADCC and CDC depends on the host immune system interacting with the Fc-part of the antibody, which is determined by the heavy chain constant domain. Of the naturally occurring constant domains, gamma1 is the isotype that most effectively evokes ADCC and CDC (Janeway's Immunobiology, 2008, 7th edition, Garland Science). Accordingly, the preferred Fc for the antibodies of the invention is a gamma 1 Fc, making the anti-CD40 antibody an IgG1 isotype. It would also be possibly to further enhance these effects using a number of known methods, such as Fc-engineering (point mutations) and glycan modifications (reviewed by Carter, Nature Reviews Immunology, 2006 (6), 343-357).

The mechanism by which the antibodies activate CD40 on dendritic cells and B cells is dependent on both the epitope on CD40 to which it binds and on receptor multimerization.

The dimerization of the CD40 receptor by the exemplary bivalent antibody (IgG1) of the invention is advantageous for its agonistic effect.

By "CD40" we include any natural or synthetic protein with structural and/or functional identity to the human CD40 protein as defined herein and/or natural variants thereof.

Preferably, the CD40 is human CD40, such as UniProt Accession No. P25942 and GenBank Accession No. AAH12419.

However, it will be appreciated by skilled persons that the CD40 be from any mammal such as a domesticated mammal (preferably of agricultural or commercial significance including a horse, pig, cow, sheep, dog and cat). By "mammalian protein" we include any protein found in, derived from, and/or isolated from, one or more cells of a mammal; for example, the term "human protein" includes a protein found in, derived from, and/or isolated from one or more cells of a human.

As discussed above, the antibodies, antigen-binding fragments, variants, fusions and derivatives thereof, of the invention are capable of activating B cells and dendritic cells.

Professional APCs, such as dendritic cells, are activated when signalling via CD40 occurs, which triggers several biological events, including immune cell activation, proliferation, and production of cytokines and chemokines. Methods for determining Dendritic cell activation associated with CD40 are known in the art (discussed, for example, in Schonbeck et al., 2001, *Cell Mol Life Sci.*, 58:40-43; van Kooten et al., 2000, *J. Leuk., Biol.*, 67: 2-17) and are described in the accompanying Examples.

Stimulation of human B cells with recombinant CD40L or anti-CD40 antibodies induces up-regulation of surface markers, such as CD23, CD30, CD80, CD86, Fas and MHC II, secretion of soluble cytokines, e.g. IL-6, TNF-γ and TNF-α, and homeotypic aggregation. Methods for determining CD40-related B cell activation are known in the art (discussed, for example, in Schonbeck et al., 2001, supra) and are described in the accompanying Examples.

The antibodies, antigen-binding fragments, variants, fusions and derivatives thereof, of the invention have been optimised in order to provide improved potency for the activation of dendritic cells. In one embodiment, the potency for the activation of dendritic cells is selectively increased relative to the potency for the activation of B cells.

Methods and assays for determining the potency of an antibody for the activation of dendritic cells and B cells are well known in the art.

For example, the activation of dendritic cells may be assessed by measuring the upregulation of cell surface markers such as CD86 and CD80 (see Example 3) and/or by measuring anti-CD40 antibody-induced secretion of IFNγ from T cells (see Example 4 below).

Likewise, the activation of B cells may be assessed by measuring the upregulation of cell surface markers (such as CD86; see Gladue et al., 2011, supra.) and/or by measuring anti-CD40 antibody-induced B cell proliferation (see Example 6 below).

The antibodies, antigen-binding fragments, variants, fusions and derivatives thereof, of the invention activate dendritic cells at least as potently as they activate B cells (for example, as determined by measurement of the upregulation of CD80 and/or CD86 thereon). Thus, the antibodies, antigen-binding fragments, variants, fusions and derivatives thereof, of the invention may have two-fold greater potency for the activation of dendritic versus B cells, for example, at least three-fold, four-fold, five-fold, six-fold, seven-fold, eight-fold, nine-fold, ten-fold or more greater potency for the activation of dendritic cells.

By "antibody" we include substantially intact antibody molecules, as well as chimaeric antibodies, humanised antibodies, human antibodies (wherein at least one amino acid is mutated relative to the naturally occurring human antibodies), single chain antibodies, bi-specific antibodies, antibody heavy chains, antibody light chains, homo-dimers and heterodimers of antibody heavy and/or light chains, and antigen binding fragments and derivatives of the same. The term also includes antibody-like molecules which may be produced using phage-display techniques or other random selection techniques for molecules. The term also includes all classes of antibodies, including: IgG, IgA, IgM, IgD and IgE.

As discussed further below, also included in the invention are antibody fragments such as Fab, F(ab')$_2$, Fv and other fragments thereof that retain the antigen-binding site. Similarly the term "antibody" includes genetically-engineered derivatives of antibodies such as single chain Fv molecules (scFv) and single domain antibodies (dAbs). Such fragments and derivatives can be made multivalent for CD40 by multimerisation, e.g. scFv-scFV or dAb-dAb dimers.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

The invention encompass variants, fusions and derivatives of the antibodies and antigen-binding fragments of the invention, as well as fusions of a said variants or derivatives, provided such variants, fusions and derivatives have binding specificity for CD40 and a potency for Dendritic cell activation which is higher than, or is equal to, potency for B cell activation.

As antibodies and antigen-binding fragments thereof comprise one or more polypeptide component, suitable variants, fusions and derivatives of the antibody and antigen-binding fragment thereof as defined herein may be made using the methods of protein engineering and site-directed mutagenesis well known in the art using the recombinant polynucleotides (see example, see *Molecular Cloning: a Laboratory Manual*, 3rd edition, Sambrook & Russell, 2001, Cold Spring Harbor Laboratory Press, which is incorporated herein by reference).

Thus, variants, fusions and derivatives of the antibody or antigen-binding fragment thereof as defined herein, may be made based on the polypeptide component of the antibody or antigen-binding fragment thereof.

By "fusion" we include said polypeptide fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc-tag epitope. Fusions to any variant or derivative of said polypeptide are also included in the scope of the invention.

The fusion may comprise or consist of a further portion which confers a desirable feature on the said polypeptide; for example, the portion may be useful in detecting or isolating the polypeptide, or promoting cellular uptake of the polypeptide. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc-tag, as known to those skilled in the art or may be a lipophilic molecule or polypeptide domain that is capable of promoting cellular uptake of the polypeptide, as known to those skilled in the art.

By "variants" of said polypeptide we include insertions, deletions and substitutions, either conservative or non-conservative. In particular we include variants of the polypeptide where such changes do not substantially alter the activity of the said polypeptide. Variants may include, for example, allelic variants which will typically, vary from the given sequence by only one or two or three, and typically no more than 10 or 20 amino acid residues. Typically, the variants have conservative substitutions.

The polypeptide variant may have an amino acid sequence which has at least 75% identity with one or more of the amino acid sequences given above, for example at least 80%, at least 90%, at least 95%, at least 96%, at least 97%, at least 98%, or at least 99% identity with one or more of the amino acid sequences specified herein.

For example, variants of the polypeptides defined herein include polypeptides comprising a sequence with at least 60% identity to an amino acid sequence selected from the group comprising: SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; and SEQ ID NO:28; SEQ ID NO:32; SEQ ID NO:33; SEQ ID NO:34; SEQ ID NO:35; SEQ ID NO:36; SEQ ID NO:37; SEQ ID NO:38; and SEQ ID NO:39; and is preferably at least 70% or 80% or 85% or 90% identity to said sequence, and more preferably at least 95%, 96%, 97%, 98% or 99% identity to said sequence.

Percent identity can be determined by, for example, the LALIGN program (Huang and Miller, Adv. Appl. Math. (1991) 12:337-357) at the Expasy facility site www.ch.embnet.org/software/LALIGN_form.html) using as parameters the global alignment option, scoring matrix BLOSUM62, opening gap penalty −14, extending gap penalty −4. Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (as described in Thompson et al., 1994, Nucl. Acid Res. 22:4673-4680, which is incorporated herein by reference). The parameters used may be as follows:

Fast pair-wise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

The antibody, antigen-binding fragment, variant, fusion or derivative of the invention may comprise or consist of one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) J. Immunol. 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, Proc. Natl. Acad. Sci. USA 75:2636 and Thursell et al., 1983, Biochem. Biophys. Res. Comm. 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary polypeptides of the invention comprise or consist of terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminus cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods are discussed and disclosed in U.S. Pat. No. 6,008,058, which is incorporated herein by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in Protease Inhibitors, Barrett and Selveson, eds., Elsevier (1986), which is incorporated herein by reference, has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

Thus, in one embodiment the said polypeptide is cyclic. However, in an alternative embodiment, the said polypeptide is linear.

Preferably, the antibody, antigen-binding fragment, variant, fusion or derivative thereof has a higher potency for dendritic cell activation than the known anti-CD40 antibody "B44" (the amino acid sequences of which are shown in Example 10 below).

The B44 agonistic antibody originates from the n-CoDeR® library, which is a human antibody fragment display library, and property of BioInvent International AB (Söderlind et al., 2000, *Nature Biotechnol.*, 18:852-6; WO 98/32845). The B44 antibody has a moderate to low affinity constant (KD) of 1.7 nM, and moderate potency as determined in vitro (Ellmark et al., 2002, *Immunology*, 106:456-463; Ellmark et al., 2008, *AIDS Research and Human Retroviruses*, 243, 367-372). The affinity and potency of the B44 agonistic antibody renders it unsuitable as a clinically and therapeutically relevant anti-CD40 agonist antibody.

More preferably, the antibody, antigen-binding fragment, variant, fusion or derivative thereof has a potency for dendritic cell activation (measured as an EC50, as described in Example 4) of at least 0.5 µg/ml (i.e. the EC50 is lower or equal to 0.5 µg/ml). For example, the antibody, antigen-binding fragment, variant, fusion or derivative thereof may have an EC50 for stimulation of CD80 (as measured in Example 4) of less than 0.5 µg/ml, e.g. less than 0.4 µg/ml, 0.3 µg/ml, 0.2 µg/ml, 0.1 µg/ml, or less than 0.05 µg/ml.

In one embodiment on the invention, the antibody, antigen-binding fragment, variant, fusion or derivative thereof has improved binding specificity for CD40 relative to that of the B44 antibody.

Concerning antibody binding specificities, the kinetic parameter that is most commonly referred to is the overall affinity, usually expressed as the dissociation constant (KD). This static parameter reflects the relative occupancy of a cell receptor at equilibrium and is relevant for systemic administration. However, during local administration the antibody may leak out of the local tumour area and the reaction time is thus limited. Therefore, a high on-rate (high ka) may be very important for the clinical effect during local administration, since it determines the time it takes for the antibody to reach equilibrium (Katakura et al., Journal of Molecular Catalysis, (28), 191-200, 2004). In addition, a slow off-rate may (low kd) affect the duration of the treatment, and may serve to constrain the antibody to the tumour area, thereby minimizing systemic exposure and toxicity.

Methods for measuring the overall affinity (KD) and on-rate (ka) and off-rate (kd) of an interaction (such as an interaction between an antibody and a ligand) are well known in the art. Exemplary in vitro methods are described in the accompanying Examples. It is also conceivable to use flow cytometry based methods (Sklar et al., *Annu Rev Biophys Biomol Struct*, (31), 97-119, 2002).

The antibody of the invention, or antigen-binding fragment, variant, fusion or derivative thereof, has an affinity (KD) for CD40 of lower than $1.0 \times 10^{-10}$ M, for example a KD lower than $9.0 \times 10^{-11}$ M, $8.0 \times 10^{-11}$ M, $7.0 \times 10^{-11}$ M, $6.0 \times 10^{-11}$ M, $5.0 \times 10^{-11}$ M, $4.0 \times 10^{-11}$ M, $3.0 \times 10^{-11}$ M, $2.0 \times 10^{-11}$ M or lower than $1.0 \times 10^{-11}$ M.

In another preferred embodiment, the antibody, antigen-binding fragment, variant, fusion or derivative thereof has an on-rate for CD40 higher than that of the B44 antibody, for example an on-rate (ka) of greater than $2.7 \times 10^6$ Ms, and preferably an on-rate (ka) of greater than $3.0 \times 10^6$ Ms; or $4.0 \times 10^6$ Ms; or $5.0 \times 10^6$ Ms; or $6.0 \times 10^6$ Ms; or $7.0 \times 10^6$ Ms; or $8.0 \times 10^6$ Ms; or $9.0 \times 10^6$ Ms; or $1.0 \times 10^7$ Ms.

In another preferred embodiment, the antibody, antigen-binding fragment, variant, fusion or derivative thereof has a lower off-rate for CD40 lower than that of the B44 antibody, for example an off-rate (kd) of lower than $4.5 \times 10^{-3}$ s, and preferably an off-rate of lower than $3.0 \times 10^{-3}$ s; or $2.0 \times 10^{-3}$ s; or $1.0 \times 10^{-3}$ s; or $9.0 \times 10^{-4}$ s; or $8.0 \times 10^{-4}$ s; or $7.0 \times 10^{-4}$ s; or $6.0 \times 10^{-4}$ s; or $5.0 \times 10^{-4}$ s; or $3.0 \times 10^{-4}$ s; or $2.0 \times 10^{-4}$ s; or $1.0 \times 10^{-4}$ s; or $9.0 \times 10^{-5}$ S; or $8.0 \times 10^{-5}$ s; or $7.0 \times 10^{-5}$ s; or $6.0 \times 10^{-5}$ s; or $5.0 \times 10^{-5}$ s; or $4.0 \times 10^{-5}$ s; or $3.0 \times 10^{-5}$ s; or $2.0 \times 10^{-5}$ s; or $1.0 \times 10^{-6}$ s.

In one preferred embodiment, the antibody, antigen-binding fragment, variant, fusion or derivative thereof has an affinity (KD) for CD40 in the range $1.0 \times 10^{-10}$ M to $1 \times 10^{-11}$ M and an on-rate (ka) for CD40 in the range 2.7 $10^6$ to $1 \times 10^7$ Ms.

Typically, the invention provides an antibody or antigen-binding fragment, or a variant, fusion or derivative thereof, with affinity for CD40 localised on the surface of a cell.

By "localised on the surface of a cell" we include the meaning that CD40 is associated with the cell such that one or more region of CD40 is present on outer face of the cell surface. For example, CD40 may be inserted into the cell plasma membrane (i.e. orientated as a transmembrane protein) with one or more region presented on the extracellular surface. Alternatively, CD40 may be outside the cell with covalent and/or ionic interactions localising it to a specific region or regions of the cell surface.

Thus, by "surface of a cancer cell" we include the meaning that CD40 is localised in such a manner in relation to one or more cell derived from, or characteristic of, a cancerous cell or tumour.

In one embodiment, the antibody or antigen-binding fragment, or a variant, fusion or derivative thereof, comprises or consist of an intact antibody.

Alternatively, the antibody or antigen-binding fragment, or a variant, fusion or derivative thereof, comprises or consists of an antigen-binding fragment selected from the group consisting of: an Fv fragment (such as a single chain Fv fragment, or a disulphide-bonded Fv fragment), and a Fab-like fragment (such as a Fab fragment; a Fab' fragment or a F(ab)₂ fragment).

For example, the antigen-binding fragment, or variant, fusion or derivative thereof, may comprise an scFv.

By "ScFv molecules" we include molecules wherein the $V_H$ and $V_L$ partner domains are linked via a flexible oligopeptide.

The potential advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from *E. coli*, thus allowing the facile production of large amounts of the said fragments.

Preferably, the antibody, antigen-binding fragment, variant, fusion or derivative thereof, of the invention is a recombinant molecule.

Although the antibody may be a polyclonal antibody, it is preferred if it is a monoclonal antibody, or that the antigen-binding fragment, variant, fusion or derivative thereof, is derived from a monoclonal antibody.

Suitable monoclonal antibodies may be prepared by known techniques, for example those disclosed in "*Monoclonal Antibodies; A manual of techniques*", H Zola (CRC Press, 1988) and in "*Monoclonal Hybridoma Antibodies: Techniques and Application*", SGR Hurrell (CRC Press, 1982). Polyclonal antibodies may be produced which are poly-specific or mono-specific. It is preferred that they are mono-specific.

Preferably, the antibody, antigen-binding fragment, variant, fusion or derivative thereof, is human or humanised.

The antibodies may be human antibodies in the sense that they have the amino acid sequence of human antibodies with specificity for the CD40 protein defined herein, however it will be appreciated that they may be prepared using methods known in the art that do not require immunisation of humans. For example, the antibody polypeptides may be produced in vitro in a human or non-human cell line. Alternatively, transgenic mice are available which contain, in essence, human immunoglobulin genes (see Vaughan et al (1998) *Nature Biotechnol.* 16, 535-539).

Suitably prepared non-human antibodies can be "humanised" in known ways, for example by inserting the CDR regions of mouse antibodies into the framework of human antibodies.

Chimeric antibodies are discussed by Neuberger et al (1998, 8$^{th}$ *International Biotechnology Symposium* Part 2, 792-799).

It will be appreciated by persons skilled in the art that the binding specificity of an antibody or antigen-binding fragment thereof is conferred by the presence of complementarity determining regions (CDRs) within the variable regions of the constituent heavy and light chains. As discussed below, in a particularly preferred embodiment of the antibodies and antigen-binding fragments, variants, fusions and derivatives thereof defined herein, binding specificity for CD40 is conferred by the presence of one or more of the CDR amino acid sequences defined herein.

The term "amino acid" as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides as defined herein comprise or consist of L-amino acids.

In a preferred embodiment, the antibody, fragment, variant, fusion or derivative comprises a variable light chain ($V_L$) in which CDR1 comprises or consists of the amino acid sequence:

[SEQ ID NO: 1]
CTGSX₁SNIGAGYX₂VY wherein:
X₁ is S or T; and
X₂ is K or H or D or G or N.

In a preferred embodiment, the antibody, fragment, variant, fusion or derivative comprises a variable light chain ($V_L$) in which CDR2 comprises or consists of the amino acid sequence:

[SEQ ID NO: 2]
X₃NINRPS wherein:
X₃ is G or R.

In a preferred embodiment, the antibody, fragment, variant, fusion or derivative comprises a variable light chain ($V_L$) in which CDR3 comprises or consists of the amino acid sequence:

CAAWDX$_4$X$_5$X$_6$X$_7$GLX$_8$ [SEQ ID NO: 3]

wherein:
X$_4$ is D or S or E or G or K; and
X$_5$ is S or T or G; and
X$_6$ is L or S or T or L or I; and
X$_7$ is S or T or L; and
X$_8$ is V or L.

More preferably, the antibody, fragment, variant, fusion or derivative comprises a variable light chain ($V_L$) in which CDR1 comprises or consists of an amino acid sequence selected from the group consisting of:

CTGSTSNIGAGYKVY; [SEQ ID NO: 4]
and

CTGSSSNIGAGYHVY; [SEQ ID NO: 5]
and

CTGSSSNIGAGYKVY; [SEQ ID NO: 6]
and

CTGSSSNIGAGYDVY; [SEQ ID NO: 7]
and

CTGSSSNIGAGYGVY; [SEQ ID NO: 8]
and

CTGSSSNIGAGYNVY. [SEQ ID NO: 9]

More preferably, the antibody, fragment, variant, fusion or derivative comprises a variable light chain ($V_L$) in which CDR2 comprises or consists of an amino acid sequence selected from the group consisting of:

GNINRPS; [SEQ ID NO: 10]
and

RNINRPS. [SEQ ID NO: 11]

More preferably, the antibody, fragment, variant, fusion or derivative comprises a variable light chain ($V_L$) in which CDR3 comprises or consists of an amino acid sequence selected from the group consisting of:

CAAWDDSLSGLV; [SEQ ID NO: 12]
and

CAAWDSSSSGLV; [SEQ ID NO: 13]
and

CAAWDESITGLV; [SEQ ID NO: 14]
and

CAAWDGSLLGLV; [SEQ ID NO: 15]
and

CAAWDGTLTGLL; [SEQ ID NO: 16]
and

CAAWDKSISGLV; [SEQ ID NO: 17]
and

CAAWDGGLLGLV. [SEQ ID NO: 18]

In particularly preferred embodiments of the invention, the antibody or antigen-binding fragment, or a variant, fusion or derivative thereof, comprises a variable light chain ($V_L$) comprising the following CDRs:
(i) SEQ ID NO:1 and SEQ ID NO:2 and SEQ ID NO:3; or
(ii) SEQ ID NO:4 and SEQ ID NO:10 and SEQ ID NO:12; or
(iii) SEQ ID NO:5 and SEQ ID NO:10 and SEQ ID NO:13; or
(iv) SEQ ID NO:4 and SEQ ID NO:10 and SEQ ID NO:12; or
(v) SEQ ID NO:6 and SEQ ID NO:10 and SEQ ID NO:14; or
(vi) SEQ ID NO:7 and SEQ ID NO:11 and SEQ ID NO:15; or
(vii) SEQ ID NO:8 and SEQ ID NO:10 and SEQ ID NO:16; or
(viii) SEQ ID NO:9 and SEQ ID NO:10 and SEQ ID NO:17; or
(ix) SEQ ID NO:9 and SEQ ID NO:10 and SEQ ID NO:12; or
(x) SEQ ID NO:9 and SEQ ID NO:10 and SEQ ID NO:18.

In a still further preferred embodiment, the antibody, fragment, variant, fusion or derivative comprises a variable light chain ($V_L$) comprising an amino acid sequence selected from the group consisting of:
SEQ ID NO:19; SEQ ID NO:20; SEQ ID NO:21; SEQ ID NO:22; SEQ ID NO:23; SEQ ID NO:24; SEQ ID NO:25; SEQ ID NO:26; and SEQ ID NO:27.

In one embodiment, the antibody, fragment, variant, fusion or derivative comprises a constant light chain (CO comprising the amino acid sequence of SEQ ID NO:63.

It is also preferred that the antibody, fragment, variant, fusion or derivative comprises a variable heavy chain ($V_H$) in which CDR1 comprises or consists of the amino acid sequence of:

GFTFSTYGMH [SEQ ID NO: 28]

Also preferable is that the antibody, fragment, variant, fusion or derivative comprises a variable heavy chain ($V_H$) in which CDR2 comprises or consists of the amino acid sequence of:

GKGLEWLSYISGGSSYIFYADSVRGR [SEQ ID NO: 29]

Also preferred is that the antibody, fragment, variant, fusion or derivative comprises a variable heavy chain ($V_H$) in which CDR3 comprises or consists of the amino acid sequence of:

CARILRGGSGMDL. [SEQ ID NO: 30]

In a particularly preferred embodiment of the invention, the antibody, fragment, variant, fusion or derivative comprises a variable heavy chain ($V_H$) comprising the CDRs of SEQ ID NO:28 and SEQ ID NO:29 and SEQ ID NO:30.

In a further preferred embodiment, the antibody, fragment, variant, fusion or derivative comprises a variable heavy chain ($V_H$) comprising an amino acid sequence selected from the group consisting of:
SEQ ID NO:31; SEQ ID NO:32; SEQ ID NO:33; SEQ ID NO:34; SEQ ID NO:35; SEQ ID NO:36; SEQ ID NO:37; SEQ ID NO:38; and SEQ ID NO:39.

In one embodiment, the antibody, fragment, variant, fusion or derivative comprises a constant heavy chain ($C_H$) comprising the amino acid sequence of SEQ ID NO:62.

It is particularly preferred that the antibody, fragment, variant, fusion or derivative comprises the following CDRs:
(i) SEQ ID NO:1 and SEQ ID NO:2 and SEQ ID NO:3 and SEQ ID NO:28 and SEQ ID NO:29 and SEQ ID NO:30; or
(ii) SEQ ID NO:4 and SEQ ID NO:10 and SEQ ID NO:12 and SEQ ID NO:28 and SEQ ID NO:29 and SEQ ID NO:30; or
(iii) SEQ ID NO:5 and SEQ ID NO:10 and SEQ ID NO:13 and SEQ ID NO:28 and SEQ ID NO:29 and SEQ ID NO:30; or
(iv) SEQ ID NO:4 and SEQ ID NO:10 and SEQ ID NO:12 and SEQ ID NO:28 and SEQ ID NO:29 and SEQ ID NO:30; or
(v) SEQ ID NO:6 and SEQ ID NO:10 and SEQ ID NO:14 and SEQ ID NO:28 and SEQ ID NO:29 and SEQ ID NO:30; or
(vi) SEQ ID NO:7 and SEQ ID NO:11 and SEQ ID NO:15 and SEQ ID NO:28 and SEQ ID NO:29 and SEQ ID NO:30; or
(vii) SEQ ID NO:8 and SEQ ID NO:10 and SEQ ID NO:16 and SEQ ID NO:28 and SEQ ID NO:29 and SEQ ID NO:30; or
(viii) SEQ ID NO:9 and SEQ ID NO:10 and SEQ ID NO:17 and SEQ ID NO:28 and SEQ ID NO:29 and SEQ ID NO:30; or
(ix) SEQ ID NO:9 and SEQ ID NO:10 and SEQ ID NO:12 and SEQ ID NO:28 and SEQ ID NO:29 and SEQ ID NO:30; or
(x) SEQ ID NO:9 and SEQ ID NO:10 and SEQ ID NO:18 and SEQ ID NO:28 and SEQ ID NO:29 and SEQ ID NO:30.

In one embodiment, the antibody or antigen-binding fragment, or a variant, fusion or derivative thereof, of the invention binds to an epitope within the first domain (D1) of CD40 (preferably, human CD40).

For example, the antibody or antigen-binding fragment, or a variant, fusion or derivative thereof, of the invention may compete for binding to CD40 with one or more of the exemplary antibodies of the invention (see Table A; as described in the Examples below):

TABLE A

Exemplary antibodies of the invention (variable regions)

| Exemplary antibody | Amino acid sequence | |
| --- | --- | --- |
| | $V_L$ | $V_H$ |
| A4 | SEQ ID NO: 19 | SEQ ID NO: 31 |
| A5 | SEQ ID NO: 20 | SEQ ID NO: 32 |
| C4 | SEQ ID NO: 21 | SEQ ID NO: 33 |
| G4 | SEQ ID NO: 22 | SEQ ID NO: 34 |

TABLE A-continued

Exemplary antibodies of the invention (variable regions)

| Exemplary antibody | Amino acid sequence | |
| --- | --- | --- |
| | $V_L$ | $V_H$ |
| F6 | SEQ ID NO: 23 | SEQ ID NO: 35 |
| F9 | SEQ ID NO: 24 | SEQ ID NO: 36 |
| G12 | SEQ ID NO: 25 | SEQ ID NO: 37 |
| H12 | SEQ ID NO: 26 | SEQ ID NO: 38 |
| B9 and H11 | SEQ ID NO: 27 | SEQ ID NO: 39 |

Thus, the antibody or antigen-binding fragment, or a variant, fusion or derivative thereof, of the invention may bind to the same CD40 epitope as one or more of the exemplary antibodies of the invention.

In one preferred embodiment, the antibody or antigen-binding fragment, or a variant, fusion or derivative thereof, of the invention comprises the $V_L$ and $V_H$ pairs of one of the exemplary antibodies of the invention (as shown in Table A)

Thus, in a particularly preferred embodiment, the antibody, antigen-binding fragment, variant, fusion or derivative thereof, comprises a variable light chain ($V_L$) and a variable heavy chain ($V_H$) comprising the following amino acid sequences:
(i) SEQ ID NO:19 and SEQ ID NO:31; or
(ii) SEQ ID NO:20 and SEQ ID NO:32; or
(iii) SEQ ID NO:21 and SEQ ID NO:33; or
(iv) SEQ ID NO:22 and SEQ ID NO:34; or
(v) SEQ ID NO:23 and SEQ ID NO:35; or
(vi) SEQ ID NO:24 and SEQ ID NO:36; or
(vii) SEQ ID NO:25 and SEQ ID NO:37; or
(viii) SEQ ID NO:26 and SEQ ID NO:38; or
(ix) SEQ ID NO:27 and SEQ ID NO:39.

Preferably, the antibody, antigen-binding fragment, variant, fusion or derivative thereof, comprises an antibody Fc-region. It will be appreciated by skilled person that the Fc portion may be from an IgG antibody, or from a different class of antibody (such as IgM, IgA, IgD or IgE). For example, the Fc region may be from an IgG1, IgG2, IgG3 or IgG4 antibody. Advantageously, however, the Fc region is from an IgG1 antibody.

The Fc region may be naturally-occurring (e.g. part of an endogenously produced antibody) or may be artificial (e.g. comprising one or more point mutations relative to a naturally-occurring Fc region). Fc-regions with point mutations improving their ability to bind FcR may be advantageous, e.g. by altering serum half life or improve binding to Fcγ receptors (FcγR) involved in ADCC and CDC. In particular, mutations that enhance binding to FcγRIIB, e.g. 5267E (Stroh) et al., 2009, Curr Opin Biotechnol, 20:685-691) may be advantageous for the invention giving the link between FcγRIIB binding and functional activity of CD40 antibodies (Li et al., 2011, Science, 333: 1030-1034).

In one embodiment, the Fc-region comprises or consists of the amino acid sequence of SEQ ID NO: 62.

It is preferred that the antibody, antigen-binding fragment, variant, fusion or derivative thereof, of the invention is an IgG molecule, or is an antigen-binding fragment, a variant, a fusion or a derivative, of an IgG molecule. The amino acid sequence of a particularly preferred IgG sequence is described in the accompanying Examples.

In one embodiment, the antibody or antigen-binding fragment, or a variant, fusion or derivative thereof, of the invention further comprises a cytotoxic moiety, which may be directly and/or indirectly cytotoxic.

By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it.

Conveniently, the cytotoxic moiety is cytotoxic when intracellular and, preferably, is not cytotoxic when extracellular.

Preferably, the invention provides an antibody or antigen-binding fragment, or a variant, fusion or derivative thereof, wherein the cytotoxic moiety is a directly cytotoxic chemotherapeutic agent. Optionally, the cytotoxic moiety is a directly cytotoxic polypeptide. Cytotoxic chemotherapeutic agents are well known in the art.

Cytotoxic chemotherapeutic agents, such as anticancer agents, include: alkylating agents including nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including *vinca* alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; and hormone agonists/antagonists such as flutamide and tamoxifen.

Various of these agents have previously been attached to antibodies and other target site-delivery agents, and so antibodies of the invention comprising these agents may readily be made by the person skilled in the art. For example, carbodiimide conjugation (Bauminger & Wlchek (1980) *Methods Enzymol.* 70, 151-159; incorporated herein by reference) may be used to conjugate a variety of agents, including doxorubicin, to antibodies or peptides.

Carbodiimides comprise a group of compounds that have the general formula $R_1$—N═C═N—$R_2$, where $R_1$ and $R_2$ can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups.

The water-soluble carbodiimide, 1-ethyl-3-(3-dimethylaminopropyl) carbodiimide (EDC) is particularly useful for conjugating a functional moiety to a binding moiety and may be used to conjugate doxorubicin to tumour homing peptides. The conjugation of doxorubicin and a binding moiety requires the presence of an amino group, which is provided by doxorubicin, and a carboxyl group, which is provided by the antibody.

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger & Wilchek, supra, 1980).

Other methods for conjugating a cytotoxic moiety to antibodies can also be used. For example, sodium periodate oxidation followed by reductive alkylation of appropriate reactants can be used, as can glutaraldehyde cross-linking. However, it is recognised that, regardless of which method of producing a conjugate of the invention is selected, a determination must be made that the antibody maintains its targeting ability and that the functional moiety maintains its relevant function.

In one embodiment of the invention, the cytotoxic moiety is a cytotoxic peptide or polypeptide moiety by which we include any moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. The use of ricin as a cytotoxic agent is described in Burrows & Thorpe (1993) *Proc. Natl. Acad. Sci. USA* 90, 8996-9000, incorporated herein by reference, and the use of tissue factor, which leads to localised blood clotting and infarction of a tumour, has been described by Ran et al (1998) *Cancer Res.* 58, 4646-4653 and Huang et al (1997) *Science* 275, 547-550. Tsai et al (1995) *Dis. Colon Rectum* 38, 1067-1074 describes the abrin A chain conjugated to a monoclonal antibody and is incorporated herein by reference. Other ribosome inactivating proteins are described as cytotoxic agents in WO 96/06641. *Pseudomonas* exotoxin may also be used as the cytotoxic polypeptide moiety (see, for example, Aiello et al (1995) *Proc. Natl. Acad. Sci. USA* 92, 10457-10461; incorporated herein by reference).

Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the agents of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody, antigen-binding fragment, variant, fusion or derivative thereof in known ways. For example, EDTA or another chelating agent may be attached to the binding moiety and used to attach $^{111}$In or $^{90}$Y. Tyrosine residues may be directly labelled with $^{125}$I or $^{131}$I.

The cytotoxic moiety may be a suitable indirectly-cytotoxic polypeptide. In a particularly preferred embodiment, the indirectly cytotoxic polypeptide is a polypeptide which has enzymatic activity and can convert a non-toxic and/or relatively non-toxic prodrug into a cytotoxic drug. With antibodies, this type of system is often referred to as ADEPT (Antibody-Directed Enzyme Prodrug Therapy). The system requires that the antibody locates the enzymatic portion to the desired site in the body of the patient and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (see Senter, P. D. et al (1988) "Anti-tumour effects of antibody-alkaline phosphatase conjugates in combination with etoposide phosphate" Proc. Natl. Acad. Sci. USA 85, 4842-4846; Bagshawe (1987) Br. J. Cancer 56, 531-2; and Bagshawe, K. D. et al (1988) "A cytotoxic agent can be generated selectively at cancer sites" Br. J. Cancer. 58, 700-703.)

In a preferred embodiment, the cytotoxic moiety is capable of converting a non-cytotoxic prodrug into a cytotoxic drug.

The enzyme and prodrug of the system using a targeted enzyme as described herein may be any of those previously proposed. The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include: a phenol mustard prodrug activated by an E. coli β-glucuronidase (Wang et al, 1992 and Roffler et al, 1991); a doxorubicin prodrug activated by a human β-glucuronidase (Bosslet et al, 1994); further doxorubicin prodrugs activated by coffee bean α-galactosidase (Azoulay et al, 1995); daunorubicin prodrugs, activated by coffee bean α-D-galactosidase (Gesson et al, 1994); a 5-fluorouridine prodrug activated by an E. coli β-D-galactosidase (Abraham et al, 1994); and methotrexate prodrugs (e.g. methotrexate-alanine) activated by carboxypeptidase A (Kuefner et al, 1990, Vitols et al, 1992 and Vitols et al, 1995). These and others are included in Table B, below.

TABLE B

| Enzyme | Prodrug |
| --- | --- |
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate<br>Mitomycin phosphate |
| Beta-glucuronidase | p-Hydroxyaniline mustard-glucuronide<br>Epirubicin-glucuronide |
| Penicillin-V-amidase | Adriamycin-N phenoxyacetyl |
| Penicillin-G-amidase | N-(4'-hydroxyphenyl acetyl) palytoxin<br>Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-glucopyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

Table A is adapted from Bagshawe (1995) Drug Dev. Res. 34, 220-230, from which full references for these various systems may be obtained; the taxol derivative is described in Rodrigues, M. L. et al (1995) Chemistry & Biology 2, 223).

Suitable enzymes for forming part of an enzymatic portion include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as e.g. thrombolysin (for thrombin prodrugs); hydrolases, such as phosphatases (e.g. alkaline phosphatase) or sulphatases (e.g. aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

Preferably, the prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the agent of the invention but it is necessary only for it to be active when (a) it is in combination with the rest of the agent of the invention and (b) the agent of the invention is attached to, adjacent to or internalised in target cells.

When each moiety is a polypeptide, the two portions may be linked together by any of the conventional ways of cross-linking polypeptides, such as those generally described in O'Sullivan et al (1979) Anal. Biochem. 100, 100-108. For example, the antibody, antigen-binding fragment, variant, fusion or derivative thereof, may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, the antibody, antigen-binding fragment, variant, fusion or derivative thereof, may be produced as a fusion compound by recombinant DNA techniques whereby a length of DNA comprises respective regions encoding the two moieties of the agent of the invention either adjacent one another or separated by a region encoding a linker peptide which does not destroy the desired properties of the agent. Conceivably, the two portions of the agent may overlap wholly or partly.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst.* 88, 1193-11203; Shewach & Lawrence (1996) *Invest. New Drugs* 14, 257-263; Horsman (1995) *Acta Oncol.* 34, 571-587; Shenoy & Singh (1992) *Clin. Invest* 10, 533-551; Mitchell et al (1989) *Int. J. Radiat. Biol.* 56, 827-836; Iliakis & Kurtzman (1989) *Int. J. Radiat. Oncol. Biol. Phys.* 16, 1235-1241; Brown (1989) *Int. J. Radiat. Oncol. Biol. Phys.* 16, 987-993; Brown (1985) *Cancer* 55, 2222-2228).

Also, delivery of genes into cells can radiosensitise them, for example delivery of the p53 gene or cyclin D (Lang et al (1998) *J. Neurosurg.* 89, 125-132; Coco Martin et al (1999) *Cancer Res.* 59, 1134-1140).

The further moiety may be one which becomes cytotoxic, or releases a cytotoxic moiety, upon irradiation. For example, the boron-10 isotope, when appropriately irradiated, releases a particles which are cytotoxic (for example, see U.S. Pat. No. 4,348,376 to Goldenberg; Primus et al (1996) *Bioconjug. Chem.* 7, 532-535).

Similarly, the cytotoxic moiety may be one which is useful in photodynamic therapy such as photofrin (see, for example, Dougherty et al (1998) *J. Natl. Cancer Inst.* 90, 889-905).

The further moiety may comprise a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis. Alternatively, the cytotoxic moiety is a nucleic acid molecule encoding a directly and/or indirectly cytotoxic polypeptide.

Examples of suitable oligonucleotides include those directed at bcl-2 (Ziegler et al (1997) *J. Natl. Cancer Inst.* 89, 1027-1036), and DNA polymerase α and topoisomerase IIα (Lee et al (1996) *Anticancer Res.* 16, 1805-1811.

Peptide nucleic acids may be useful in place of conventional nucleic acids (see Knudsen & Nielsen (1997) *Anticancer Drugs* 8, 113-118).

In a further embodiment, the antibody, antigen-binding fragment, variant, fusion or derivative thereof may be comprised in a delivery vehicle for delivering nucleic acid to the target. The delivery vehicle may be any suitable delivery vehicle. It may, for example, be a liposome containing nucleic acid, or it may be a virus or virus-like particle which is able to deliver nucleic acid. In these cases, the molecule to be delivered is typically present on the surface of the delivery vehicle. For example, a suitable antibody fragment may be present in the outer surface of a liposome and the nucleic acid to be delivered may be present in the interior of the liposome. As another example, a viral vector, such as a retroviral or adenoviral vector, is engineered so that the binding moiety is attached to or located in the surface of the viral particle thus enabling the viral particle to be targeted to the desired site. Targeted delivery systems are also known such as the modified adenovirus system described in WO 94/10323 wherein, typically, the DNA is carried within the adenovirus, or adenovirus-like, particle. Michael et al (1995) *Gene Therapy* 2, 660-668, describes modification of adenovirus to add a cell-selective moiety into a fibre protein. Targeted retroviruses are also available for use in the invention; for example, sequences conferring specific binding affinities may be engineered into pre-existing viral env genes (see Miller & Vile (1995) *Faseb J.* 9, 190-199 for a review of this and other targeted vectors for gene therapy).

Immunoliposomes (antibody-directed liposomes) may be used. For the preparation of immuno-liposomes, MPB-PE (N-[4-(p-maleimidophenyl)-butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the DNA or other genetic construct for delivery to the target cells, for example, by forming the said liposomes in a solution of the DNA or other genetic construct, followed by sequential extrusion through polycarbonate membrane filters with 0.6 μm and 0.2 μm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour.

The nucleic acid delivered to the target site may be any suitable DNA which leads, directly or indirectly, to cytotoxicity. For example, the nucleic acid may encode a ribozyme which is cytotoxic to the cell, or it may encode an enzyme which is able to convert a substantially non-toxic prodrug into a cytotoxic drug (this latter system is sometime called GDEPT: Gene Directed Enzyme Prodrug Therapy).

Ribozymes which may be encoded in the nucleic acid to be delivered to the target are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149, 796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference. Suitable targets for ribozymes include transcription factors such as c-fos and c-myc, and bcl-2. Durai et al (1997) *Anticancer Res.* 17, 3307-3312 describes a hammerhead ribozyme against bcl-2.

EP 0 415 731 describes the GDEPT system. Similar considerations concerning the choice of enzyme and prodrug apply to the GDEPT system as to the ADEPT system described above.

The nucleic acid delivered to the target site may encode a directly cytotoxic polypeptide.

Alternatively, the further moiety may comprise a polypeptide or a polynucleotide encoding a polypeptide which is not either directly or indirectly cytotoxic but is of therapeutic benefit. Examples of such polypeptides include anti-proliferative or anti-inflammatory cytokines, and anti-proliferative, immunomodulatory or factors influencing blood clotting which may be of benefit in medicine, for example in the treatment of cancer.

The further moiety may usefully be an inhibitor of angiogenesis such as the peptides angiostatin or endostatin. The further moiety may also usefully be an enzyme which converts a precursor polypeptide to angiostatin or endostatin. Human matrix metallo-proteases such as macrophage elastase, gelatinase and stromolysin convert plasminogen to angiostatin (Cornelius et al (1998) *J. Immunol.* 161, 6845-6852). Plasminogen is a precursor of angiostatin.

In one embodiment, the antibody, antigen-binding fragment, variant, fusion or derivative thereof comprises a cytotoxic moiety comprising a radioactive atom, for example a radioactive atom selected from the group consisting of: phosphorous-32; iodine-125; iodine-131; indium-111; rhenium-186; rhenium-188; yttrium-90.

In a preferred embodiment, the invention provides an antibody, antigen-binding fragment, variant, fusion or derivative thereof, further comprising a readily detectable moiety.

By a "readily detectable moiety" we include the meaning that the moiety is one which, when located at the target site following administration of the agent of the invention into a patient, may be detected, typically non-invasively from outside the body and the site of the target located. Thus, the agents of this embodiment of the invention are useful in imaging and diagnosis.

Typically, the readily detectable moiety is or comprises a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again $^{131}$I, $^{111}$In, $^{19}$F, $^{13}$C, $^{15}$N, $^{17}$O, gadolinium, manganese or iron. Clearly, the agent of the invention must have sufficient of the appropriate atomic isotopes in order for the molecule to be readily detectable.

The radio- or other labels may be incorporated in known ways. For example, the antibody, antigen-binding fragment, variant, fusion or derivative thereof, may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in polypeptides. Yttrium-90 can be attached via a lysine residue. The IODOGEN method (Fraker et al (1978) *Biochem. Biophys. Res. Comm.* 80, 49-57) can be used to incorporate $^{123}$I. Reference ("Monoclonal Antibodies in Immunoscintigraphy", J-F Chatal, CRC Press, 1989) describes other methods in detail.

Preferably, the readily detectable moiety comprises a radioactive atom, such as, for example technetium-99m or iodine-123.

Alternatively, the readily detectable moiety may be selected from the group comprising: iodine-123; iodine-131; indium-111; fluorine-19; carbon-13; nitrogen-15; oxygen-17; gadolinium; manganese; iron.

In a further preferred embodiment of the invention the further moiety is able to bind selectively to a directly or indirectly cytotoxic moiety or to a readily detectable moiety.

Thus, in this embodiment, the further moiety may be any moiety which binds to a further compound or component which is cytotoxic or readily detectable.

The further moiety may, therefore be an antibody which selectively binds to the further compound or component, or it may be some other binding moiety such as streptavidin or biotin or the like. The following examples illustrate the types of molecules that are included in the invention; other such molecules are readily apparent from the teachings herein.

A bi-specific antibody wherein one binding site comprises the antibody, antigen-binding fragment, variant, fusion or derivative thereof, of the invention, and the second binding site comprises a moiety which binds to, for example, an enzyme which is able to convert a substantially non-toxic prodrug to a cytotoxic drug.

It will be appreciated that the antibodies, antigen-binding fragments, variants, fusions, and derivatives thereof, of the invention are useful research reagents and therapeutic agents. Suitably, the antibodies, antigen-binding fragments, variants, fusions, and derivatives thereof, of the invention are detectably labelled, for example they may be labelled in such a way that they may be directly or indirectly detected.

Conveniently, the antibodies are labelled with a radioactive moiety or a coloured moiety or a fluorescent moiety, or they may be linked to an enzyme. Typically, the enzyme is one which can convert a non-coloured (or non-fluorescent) substrate to a coloured (or fluorescent) product. The antibody may be labelled by biotin (or streptavidin) and then detected indirectly using streptavidin (or biotin) which has been labelled with a radioactive moiety or a coloured moiety or a fluorescent moiety, or the like or they may be linked to any enzyme of the type described above.

Preferably, the readily detectable moiety comprises a radioactive atom, for example technetium-99m or iodine-123, or a radioactive atom selected from the group consisting of: iodine-123; iodine-131; indium-111; fluorine-19; carbon-13; nitrogen-15; oxygen-17; gadolinium; manganese; iron.

In a second aspect, the invention provides a nucleic acid molecule encoding an antibody or antigen-binding fragment, or variant, fusion or derivative thereof, according to the invention, or a component polypeptide chain thereof. By "nucleic acid molecule" we include DNA, cDNA and mRNA molecules, which may be single- or double-stranded.

Preferably, the nucleic acid molecule comprises one or more nucleotide sequence selected from the group consisting of: SEQ ID NO:40; SEQ ID NO:41; SEQ ID NO:42; or SEQ ID NO:43; or SEQ ID NO:44; or SEQ ID NO:45; or SEQ ID NO:46; or SEQ ID NO:47; or SEQ ID NO:48; or SEQ ID NO:49; or SEQ ID NO:50; or SEQ ID NO:51; or SEQ ID NO:52; or SEQ ID NO:53; or SEQ ID NO:54; or SEQ ID NO:55; or SEQ ID NO:56; or SEQ ID NO:57.

Even more preferably, the invention provides a nucleic acid molecule comprising the following nucleotide sequences:

(i) SEQ ID NO:40 and SEQ ID NO:49; or
(ii) SEQ ID NO:41 and SEQ ID NO:50; or
(iii) SEQ ID NO:42 and SEQ ID NO:52; or
(iv) SEQ ID NO:43 and SEQ ID NO:53; or
(v) SEQ ID NO:44 and SEQ ID NO:54; or
(vi) SEQ ID NO:45 and SEQ ID NO:55; or
(vii) SEQ ID NO:46 and SEQ ID NO:56; or
(viii) SEQ ID NO:47 and SEQ ID NO:57; or
(ix) SEQ ID NO:48 and SEQ ID NO:51.

In a third aspect, the invention provides a vector comprising a nucleic acid molecule according to the second aspect of the invention.

Preferably, the vector is an expression vector. By "expression vector" we mean one which is capable, in an appropriate host, of expressing a polypeptide encoded by the nucleic acid molecule.

Such vectors may be useful in expressing the encoded antibody, antigen-binding fragment, variant, fusion or derivative thereof, of the invention in a host cell for production of useful quantities.

A variety of methods have been developed to operably link nucleic acid molecules, especially DNA, to vectors, for example, via complementary cohesive termini. For instance, complementary homopolymer tracts can be added to the DNA segment to be inserted into the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, e.g. generated by endonuclease restriction digestion, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a larger molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease site are commercially available from a number of sources including International Biotechnologies Inc., New Haven, Conn., USA.

A desirable way to modify the DNA encoding a polypeptide is to use PCR. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The specific primers may contain restriction endonuclease recognition sites which can be used for cloning into expression vectors using methods known in the art.

The DNA (or in the case of retroviral vectors, RNA) is then expressed in a suitable host to produce a polypeptide comprising the agent of the invention. Thus, the DNA encoding the polypeptide may be used in accordance with known techniques, appropriately modified in view of the teachings contained herein, to construct an expression vector, which is then used to transform an appropriate host cell for the expression and production of the polypeptide. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA (or in the case or retroviral vectors, RNA) encoding a polypeptide may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the expression vector of the invention are then cultured for a sufficient time and under appropriate conditions known to those skilled in the art in view of the teachings disclosed herein to permit the expression of the polypeptide, which can then be recovered.

Many expression systems are known, including bacteria (for example, *Escherichia coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps).

Other vectors and expression systems are well known in the art for use with a variety of host cells.

In a fourth aspect, the invention provides a recombinant host cell comprising a nucleic acid molecule according to the second aspect of the invention or a vector according to the third aspect of the invention.

Preferably, the host cell is a bacterial cell or is a mammalian cell, such as a human cell.

The host cell can be either prokaryotic or eukaryotic. Bacterial cells are preferred prokaryotic host cells and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No. ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CRL 1658 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cells, bacterial cells, insect cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5 PEB using 6250V per cm at 25 µFD.

Methods for transformation of yeast by electroporation are disclosed in Becker & Guarente (1990) *Methods Enzymol.* 194, 182.

Successfully transformed cells, i.e. cells that contain a DNA construct of the present invention, can be identified by well-known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity.

Samples of cells suspected of being transformed are harvested and assayed for the protein using suitable antibodies.

The host cell may be a host cell within a non-human animal body. Thus, transgenic non-human animals which express an agent according to the invention (or a binding moiety thereof) by virtue of the presence of the transgene are included. Preferably, the transgenic non-human animal is a rodent such as a mouse. Transgenic non-human animals can be made using methods well known in the art.

In a fifth aspect, the invention provides a pharmaceutical composition comprising an effective amount of an antibody or antigen-binding fragment, or variant, fusion or derivative thereof, of the invention, and a pharmaceutically-acceptable buffer, excipient, diluent or carrier.

A 'therapeutically effective amount', or 'effective amount', or 'therapeutically effective', as used herein, refers to that amount which provides a therapeutic effect for a given condition and administration regimen. This is a predetermined quantity of active antibody calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent.

A therapeutically effective amount can be determined by the ordinary skilled medical or veterinary worker based on patient characteristics, such as age, weight, sex, condition, complications, other diseases, etc., as is well known in the art.

Thus, the antibody or antigen-binding fragment, variant, fusion or derivative thereof can be formulated at various concentrations, depending on the efficacy/toxicity of the polypeptide being used. Preferably, the formulation comprises the active polypeptide at a concentration of between 0.1 µM and 1 mM, for example between 1 µM and 500 µM, between 500 µM and 1 mM, or between 300 µM and 700 µM.

By "pharmaceutically-acceptable" is included that the formulation is sterile and pyrogen free. Suitable pharmaceutical carriers are well known in the art of pharmacy. The carrier(s) must be "acceptable" in the sense of being compatible with the antibody of the invention and not deleterious to the recipients thereof. Typically, the carriers will be water or saline which will be sterile and pyrogen free; however, other acceptable carriers may be used.

Suitable pharmaceutically acceptable buffers, diluents, carriers and excipients are well-known in the art (see Remington's Pharmaceutical Sciences, 18th edition, A. R. Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to include an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to include an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to include any compound added to the formulation to increase the biological effect of the agent of the invention. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The active antibody-based agents of the invention may be formulated into any type of pharmaceutical composition known in the art to be suitable for the delivery thereof.

In one embodiment, the pharmaceutical compositions of the invention may be in the form of a liposome, in which the agent is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the agents may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active agent. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

Advantageously, the pharmaceutical composition is suitable for administration at or near the site of a tumour, e.g. intra-tumourally or peri-tumourally.

It is preferred that the pharmaceutical composition is suitable for parenteral administration. Methods for formulating an antibody into a pharmaceutical composition will be well-known to those skilled in the arts of medicine and pharmacy. Preferred compositions are described in the accompanying Examples.

The agents (i.e. antibody, antigen-binding fragment, variant, fusion or derivative thereof), medicaments and pharmaceutical compositions of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Preferably, delivery is performed intra-muscularly (i.m.) and/or subcutaneously (s.c.) and/or intravenously (i.v.).

The agents, medicaments and pharmaceutical compositions of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the agents, medicaments and pharmaceutical compositions of the invention. A device which delivers a pulsed electric field to cells increases the permeability of the cell membranes to the drug, resulting in a significant enhancement of intracellular drug delivery.

The agents, medicaments and pharmaceutical compositions of the invention can also be delivered by electro-incorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the agents, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The agents, medicaments and pharmaceutical compositions of the invention can also be delivered orally. The process employs a natural process for oral uptake of vitamin $B_{12}$ and/or vitamin D in the body to co-deliver proteins and peptides. By riding the vitamin $B_{12}$ and/or vitamin D uptake system, the agents, medicaments and pharmaceutical compositions of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The agents, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol. 8, 84-87.

Preferably, the medicaments and/or pharmaceutical compositions of the present invention is a unit dosage containing a daily dose or unit, daily sub-dose or an appropriate fraction thereof, of the active ingredient.

The agents, medicaments and pharmaceutical compositions of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the agents, medicaments and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The agents, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents, medicaments and pharmaceutical compositions of the invention may be combined with various sweetening or flavouring agents, colouring matter or dyes, with emulsifying and/or suspending agents and with diluents such as water, ethanol, propylene glycol and glycerin, and combinations thereof.

The agents, medicaments and pharmaceutical compositions of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The medicaments and pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The agents, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate.

Capsules and cartridges (made, for example, from gelatin) for use in an inhaler or insufflator may be formulated to contain a powder mix of an agent of the invention and a suitable powder base such as lactose or starch.

Alternatively, the agents, medicaments and pharmaceutical compositions of the invention can be administered in the form of a suppository or pessary, or they may be applied topically in the form of a lotion, solution, cream, gel, ointment or dusting powder. The agents, medicaments and pharmaceutical compositions of the invention may also be transdermally administered, for example, by the use of a skin patch. They may also be administered by the ocular route, particularly for treating diseases of the eye.

For ophthalmic use, the agents, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agents, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, local administration of the agents, medicaments and pharmaceutical compositions of the invention at or near the site of a tumour is the preferred route, in particular intra-tumoural or peri-tumoural administration.

For veterinary use, the agents, medicaments and pharmaceutical compositions of the invention are administered as a suitably acceptable formulation in accordance with normal veterinary practice and the veterinary surgeon will determine the dosing regimen and route of administration which will be most appropriate for a particular animal.

In a sixth aspect, the invention provides a kit comprising a pharmaceutical composition according to the fifth aspect of the invention.

In a seventh aspect, the invention provides an antibody or antigen-binding fragment, or a variant, fusion or derivative thereof, according to the first aspect of the invention, or a nucleic acid molecule according to the second aspect of the invention, or a vector according to the third aspect of the invention, or a host cell according to the fourth aspect of the invention, or a pharmaceutical composition according to the fifth aspect of the invention, for use in medicine.

In an eighth aspect, the invention provides an antibody or antigen-binding fragment, or a variant, fusion or derivative thereof, according to the first aspect of the invention, or a nucleic acid molecule according to the second aspect of the invention, or a vector according to the third aspect of the invention, or a host cell according to the fourth aspect of the invention, or a pharmaceutical composition according to the fifth aspect of the invention, for use in the treatment of cancer.

In a ninth aspect, the invention provides an antibody or antigen-binding fragment, or a variant, fusion or derivative thereof, according to the first aspect of the invention, or a nucleic acid molecule according to the second aspect of the invention, or a vector according to the third aspect of the invention, or a host cell according to the fourth aspect of the invention, or a pharmaceutical composition according to the fifth aspect of the invention, in the manufacture of a medicament for the treatment of cancer.

Preferably, in the seventh and/or eighth and/or ninth aspects of the invention, the treatment of cancer comprises the step of administering an effective amount the antibody or antigen-binding fragment, or a variant, fusion or derivative thereof or nucleic acid molecule or vector or host cell or pharmaceutical composition to an individual in need thereof.

In a tenth aspect, the invention provides, a method for treating an individual with cancer, the method comprising the step of administering to an individual in need thereof an effective amount of: an antibody or antigen-binding fragment, or a variant, fusion or derivative thereof, according to the first aspect of the invention, or a nucleic acid molecule according to the second aspect of the invention, or a vector according to the third aspect of the invention, or a host cell according to the fourth aspect of the invention, or a pharmaceutical composition according to the fifth aspect of the invention.

It is preferred that, in the seventh and/or eighth and/or ninth and/or tenth aspects of the invention, the step of administering to an individual in need thereof comprises local administration, for example, local administration to a tumour in a patient (for example, intra-tumourally or peri-tumourally).

It is known that such local injection into a tumour of an anti-CD40 antibody may generate a systemic anti-tumour effect at a much lower dose (van Mierlo et al., 2002, *Proc Natl Acad Sci* USA, 99:5561-5566; Kalbasi et al., 2010, *J Immunotherapy*, 33:810-816). Moreover, it was reported that mice treated intra-tumourally in one flank were able to clear tumours in the opposite flank, and that the anti-tumour effect depends on activation of Dendritic cells, and subsequent activation of a response by cytotoxic T lymphocytes. In addition, the treatment produced a protective immunity to tumour re-challenge.

After patient-specific optimisation of the dose of the antibody or antigen-binding fragment, or a variant, fusion or derivative thereof, as described above, the patient is then administered the maximum therapeutic dose for the duration of the treatment. However, it will be appreciated that the dose may be lowered over time once the treatment starts to have the required therapeutic effect.

Typically, the therapeutic dose of the antibody or antigen-binding fragment, or a variant, fusion or derivative thereof, in a human patient will be in the range of 100 µg to 700 mg per administration (based on a body weight of 70 kg).

For example, the maximum therapeutic dose may be in the range of 0.1 to 10 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

In one embodiment, the maximum therapeutic dose of the antibody or antigen-binding fragment, or a variant, fusion or derivative thereof, is a low dose. For example, the dose to be administered locally in the present invention may be less than 25% of the typical systemic dose of the same agent needed to produce a therapeutic effect. In one embodiment, the dose is less than or equal to 1 mg per administration, for example less than or equal to 500 µg, 400 µg, 300 µg, 200 µg, 100 µg, 50 µg, 30 µg, 20 µg, 10 µg, 5 µg or 1 µg per administration. It will be appreciated that such doses may be administered repeatedly to the patient over time, for example twice daily, once daily, once every other day, twice weekly, once weekly, twice monthly, once monthly, etc.).

In one embodiment, the antibody-based agent(s) is/are for use at a dose of 10 µg to 100 µg per administration.

For example, the antibody-based agent(s) may be used at a dose of 20 µg to 40 µg per administration, for example 30 µg per administration.

In one embodiment, the antibody-based agent(s) is/are capable of providing a systemic anti-tumour effect. Such a systemic anti-tumour effect may be achieved even if the therapy is made locally/intratumourally. When administering an immunotherapeutic antibody locally, e.g. by intratumoural injections, only cells in the tumour area are targeted for CD40 therapy. Therefore, only the concentration of the CD40 agonist in the tissue-area where it is intended to exert its effects influence the level of CD40 activation. When administering locally, the optimal dose may be determined by the volume of the tissue area that is relevant to treat and not the body weight of the patient. When treating intratumourally this volume may instead be defined by the tumour volume. The relevant total dose may thus be lower than for systemic treatment, and may be defined based on diagnosis of the tumour by PET scan or other imaging methods, rather than by the weight of the patient.

It will be appreciated that the antibody-based agents of the invention are suitable for use in the treatment of any type of cancer for which CD40 activation may provide a therapeutic benefit.

For example, the cancer may be selected from the group consisting of: prostate cancer; breast cancer; colorectal cancer; pancreatic cancer; ovarian cancer; lung cancer; cervical cancer; rhabdomyosarcoma; neuroblastoma; multiple myeloma; leukemia, acute lymphoblastic leukemia, melanoma, bladder and glioblastoma.

In one embodiment, the cancer is associated with CD40$^+$ tumour cells. However, the antibody-based agents of the invention may also be used in the treatment of cancers associated with CD40$^-$ tumour cells.

It will be further appreciated that the antibody-based agents of the invention may be used as a sole treatment for cancer in a patient or as part of a combination treatment (which further treatment may be a pharmaceutical agent, radiotherapy and/or surgery).

Thus, the patient may also receive one or more further treatments for cancer, for example pharmaceutical agents (such as chemotherapeutic agents), radiotherapy and/or surgery.

In one embodiment, the one or more further treatments are selected from the group consisting of conventional chemotherapeutic agents (such as alkylating agents, anti-metabolites, plant alkaloids and terpenoids, topoisomerase inhibitors and antineoplastics), radiotherapeutic agents, antibody-based therapeutic agents (such as gemtuzumab, alemtuzumab, rituximab, trastuzumab, nimotuzumab, cetuximab, bevacizumab), and steroids.

In an eleventh aspect, the invention provides a method for producing an antibody or antigen-binding fragment, or a variant, fusion or derivative thereof, according to the invention, the method comprising culturing a host cell according to the fourth aspect of the invention under conditions which permit expression of the encoded antibody or antigen-binding fragment thereof.

Methods for cultivating host cells and isolating recombinant proteins are well known in the art. It will be appreciated that, depending on the host cell, the proteins produced may differ. For example, certain host cells, such as yeast or bacterial cells, either do not have, or have different, post-translational modification systems which may result in the production of forms of agents of the invention (or binding moieties thereof) which may be post-translationally modified in a different way.

It is preferred that the antibodies, antigen-binding fragments, variants, fusions or derivatives thereof, of the invention (or binding moieties thereof) are produced in a eukaryotic system, such as a mammalian cell.

According to a less preferred embodiment, the antibodies, antigen-binding fragments, variants, fusions or derivatives thereof, of the invention can be produced in vitro using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated that where the agent comprises distinct moieties, for example binding and/or cytotoxic domains, those moieties may be encoded by one or more separate nucleic acid molecules.

Preferably, the production method of this aspect of the invention comprises a further step of isolating the antibodies, antigen-binding fragments, variants, fusions or derivatives thereof, of the invention produced from the host cell or from the in vitro translation mix. Preferably, the isolation employs an antibody which selectively binds the expressed polypeptide of the invention.

Methods for producing antibodies are well known in the art. For example, antibodies may be raised in an animal by immunising with an appropriate peptide. Alternatively, with today's technology, it is possible to make antibodies without the need to use animals; such techniques include, for example, antibody phage display technology as is well known in the art.

In one embodiment, the antibody, antigen-binding fragment, variant, fusion or derivative thereof, of the invention is the product, directly or indirectly, of in vitro protein optimisation (e.g. using the FIND® technology of Alligator Bioscience AB, as described in WO 02/48351 and WO 03/097834).

The listing or discussion in this specification of an apparently prior-published document should not necessarily be taken as an acknowledgement that the document is part of the state of the art or is common general knowledge.

Preferred, non-limiting examples which embody certain aspects of the invention will now be described, with reference to the following figures:

FIG. 1—FIG. 1A: "Heat map" of the libraries and the output from selections—to primary high throughput screening (HTS). Each box represents an amino acid position. The heat maps are restricted to positions where mutations has been introduced and/or found by sequence analysis. The linker between $V_H$ and $V_L$ is not displayed. The mutational frequency in each position is indicated by darker shade. FIG.

1B: Number of positions with more than 5 mutations calculated based on sequences from the selection procedure.

Figure 2:
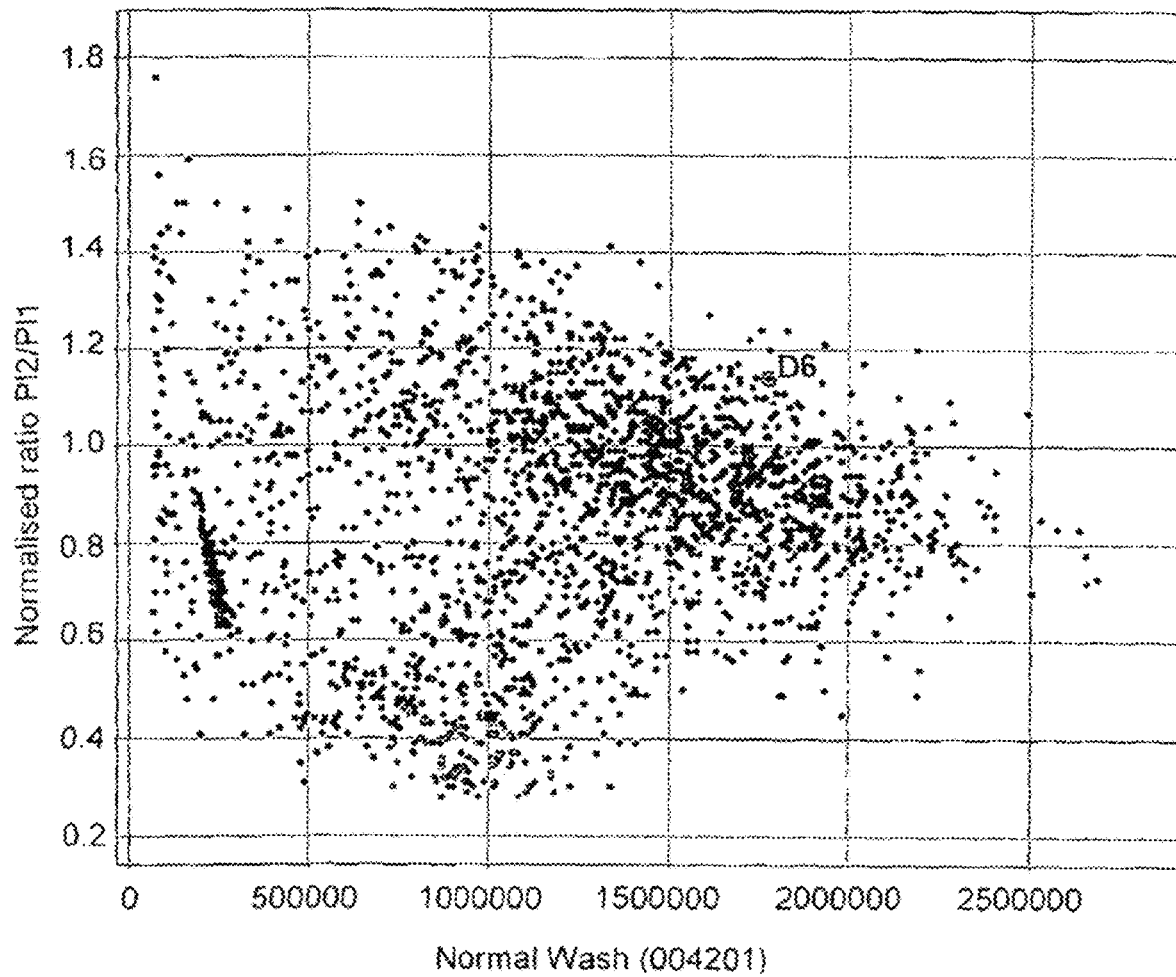

FIG. 2—Visualisation of the HTS results. The ratio from the two ELISA measurements (normal wash and harsh wash) is displayed on the y-axis; on the x-axis, the binding signal from the primary ELISA (normal wash) is displayed. Each sphere in the graph represents the data from one clone. B44 (grey) and clones from selection round number 5 (black) are shown.

Figure 3:
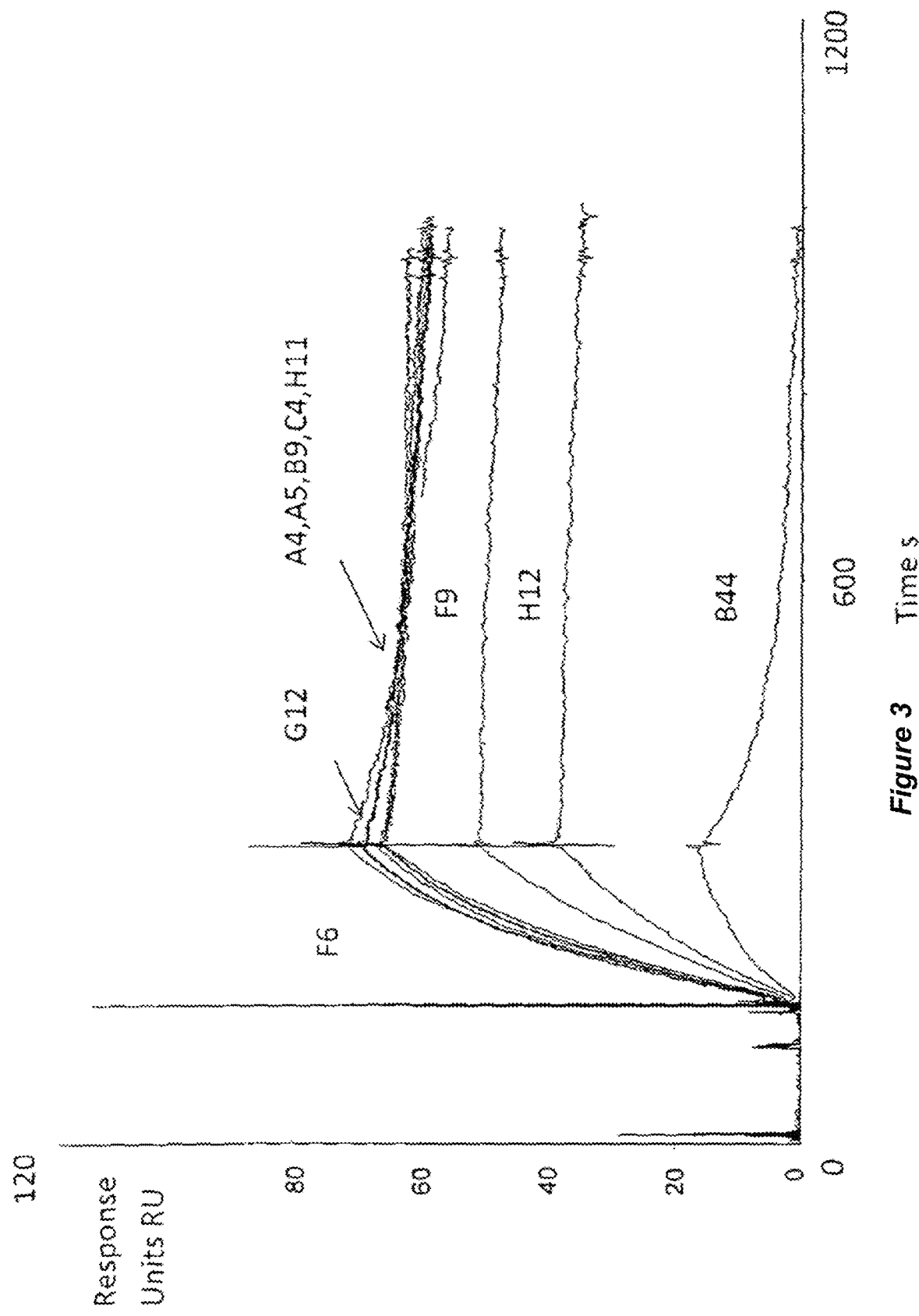

FIG. 3—Schematic diagram of the domains of CD40.

Figure 4:
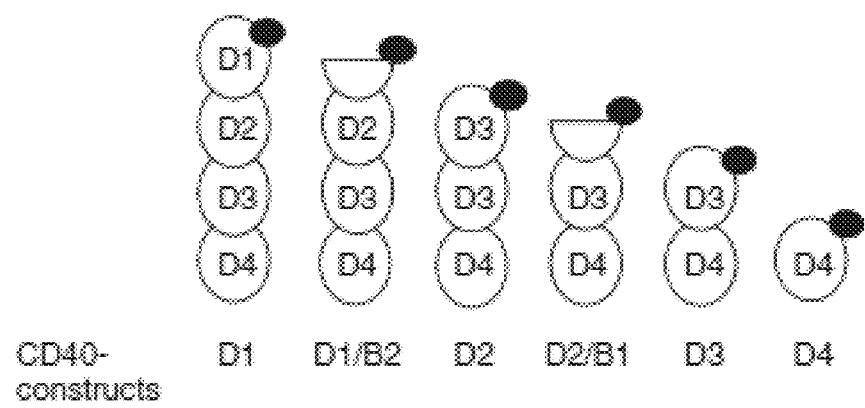

FIG. 4—Surface plasmon resonance analysis of the CD40 antibody clones binding to target at 37° C. and physiological pH.

Figure 5A:
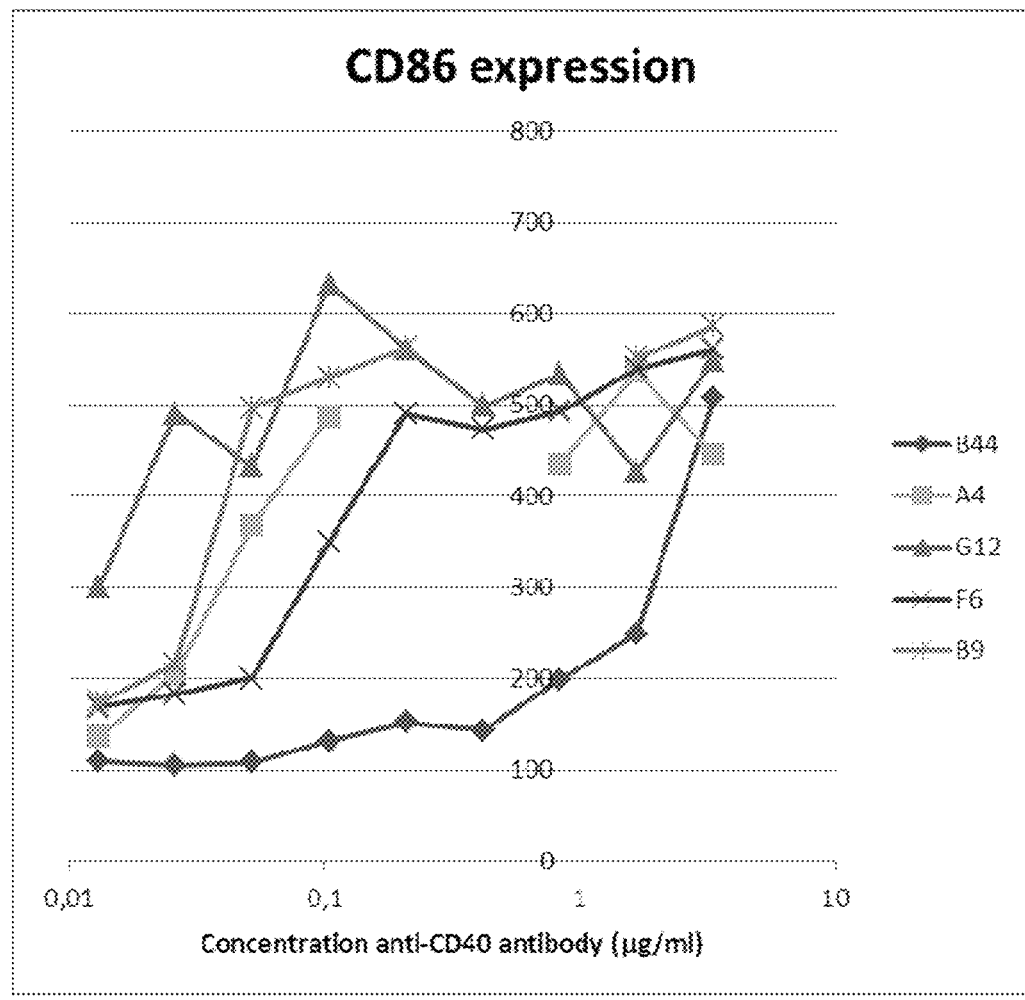
Figure 5B:
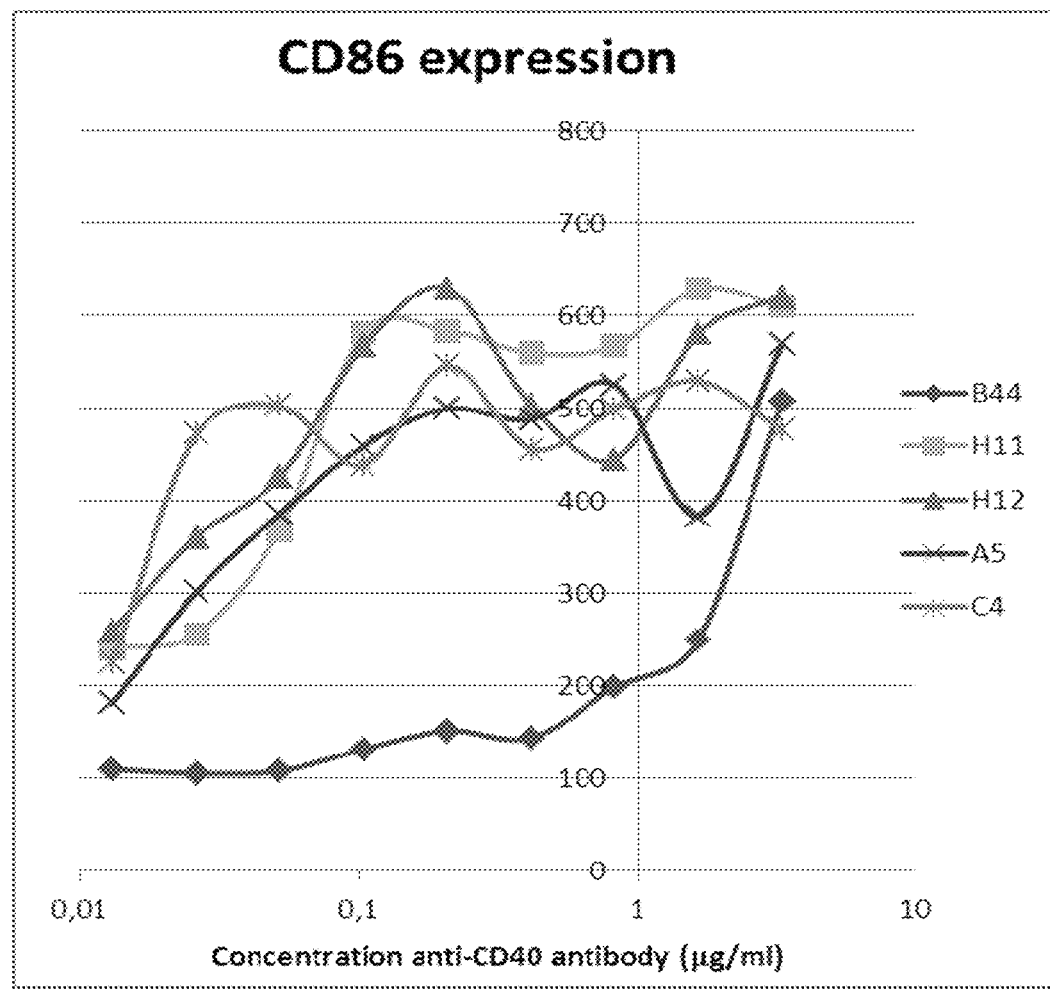

FIGS. 5A and 5B—Up-regulation of surface marker, CD86, by the CD40 antibody clones relative to the B44 antibody.

Figure 6:
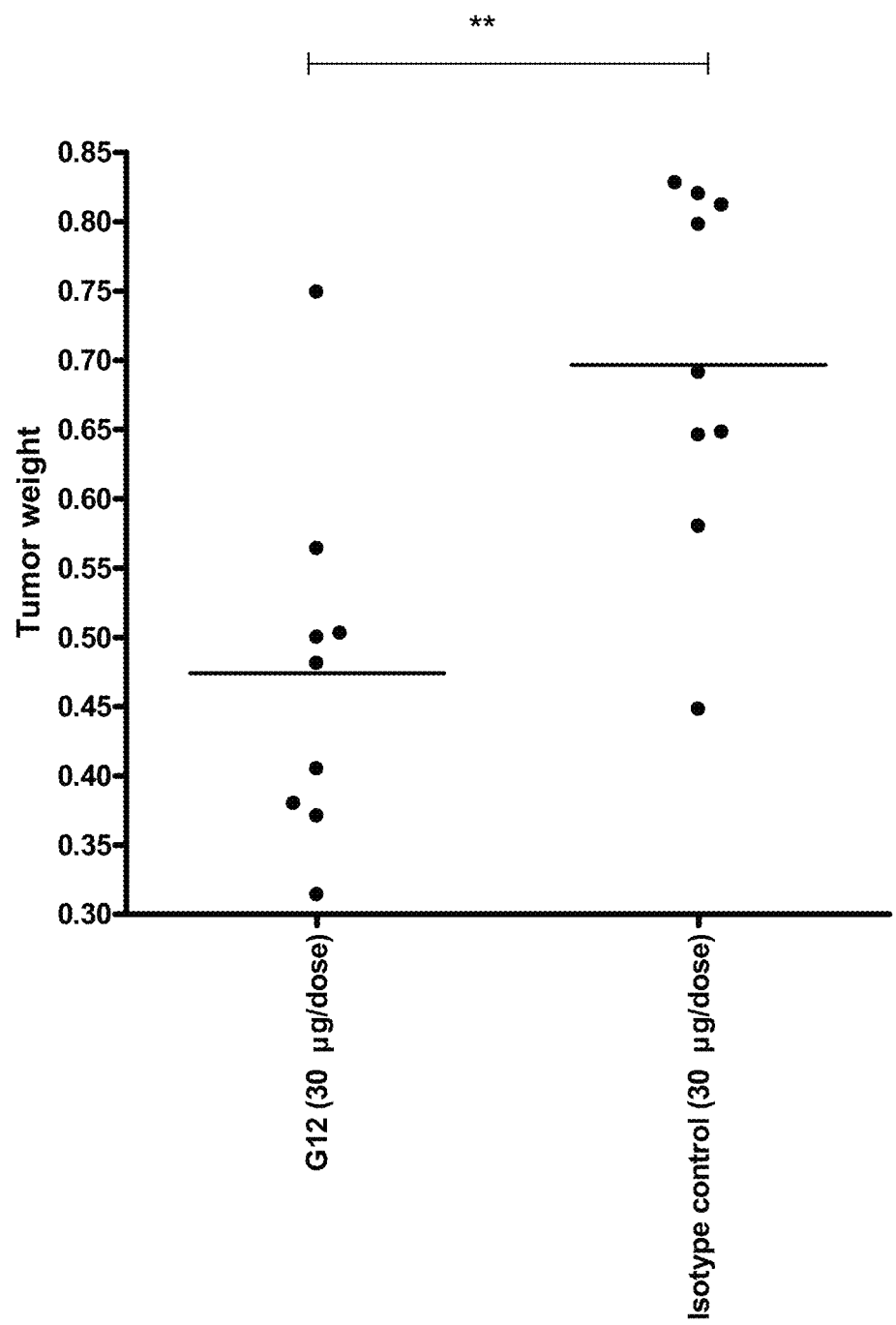

FIG. 6—The weight of the tumours measured at the end point day (day 28) is displayed. Treatment with 30 ug G12 or isotype control is displayed (**p<0.01 for both treatment groups compared to control using Mann-Whitney test, two tailed).

Figure 7:
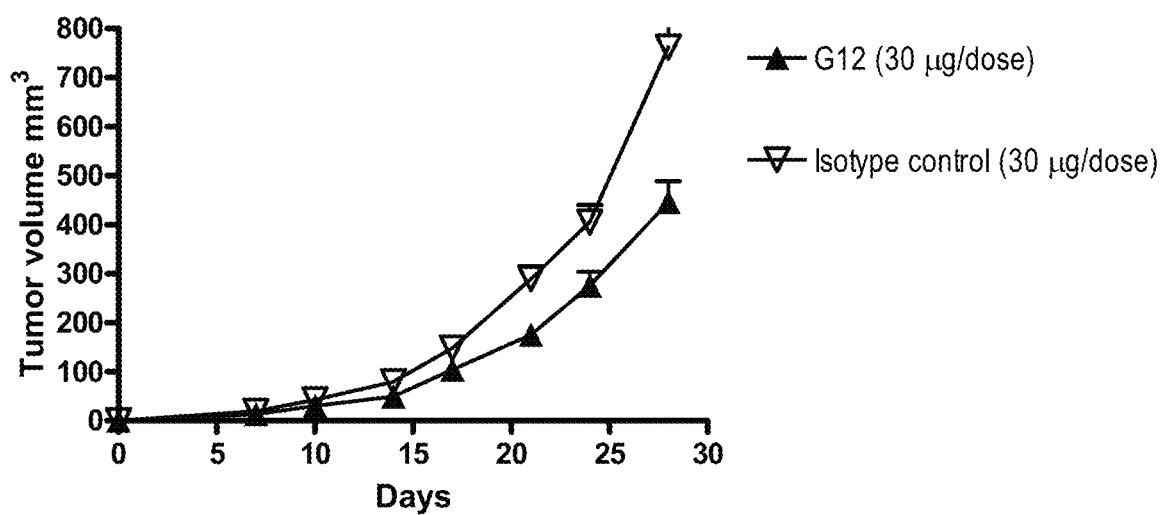

FIG. 7—The average (n=9) tumour volume of the different treatment groups is displayed (+/−SEM). The mice treated with 30 ug drug is compared to isotype control (30 ug). Treatment with G12 provides a significant anti-tumour effect compared to the isotype control.

Figure 8:
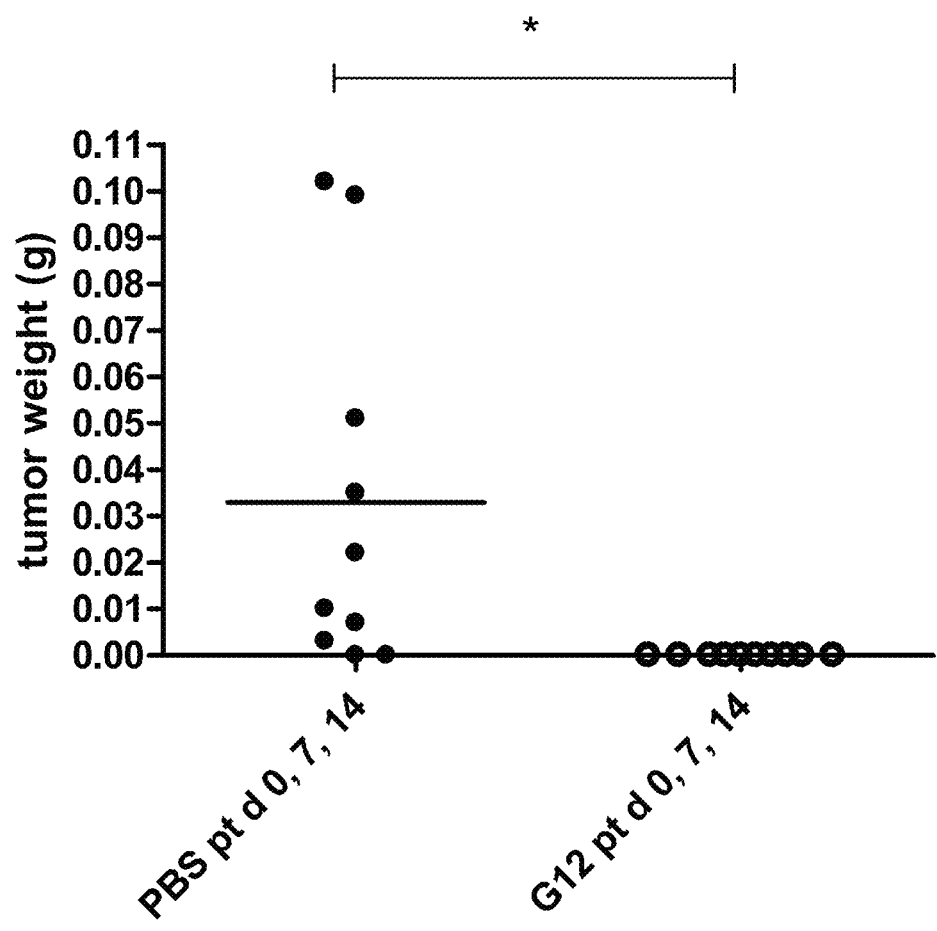

FIG. 8—The weight of the tumours measured at the end point day (day 28) is displayed. G12 is compared to PBS-treatment in the presence of human dendritic cells and T cells, whereach treatment group (n=10) grafted with autologous T cells and dendritic cells from two different donors (five mice for each donor, in total ten mice). Treatment with G12 is significant compared to the isotype control (p<0.05 for the treatment group compared to control using students t-test, two tailed).

Figure 9:
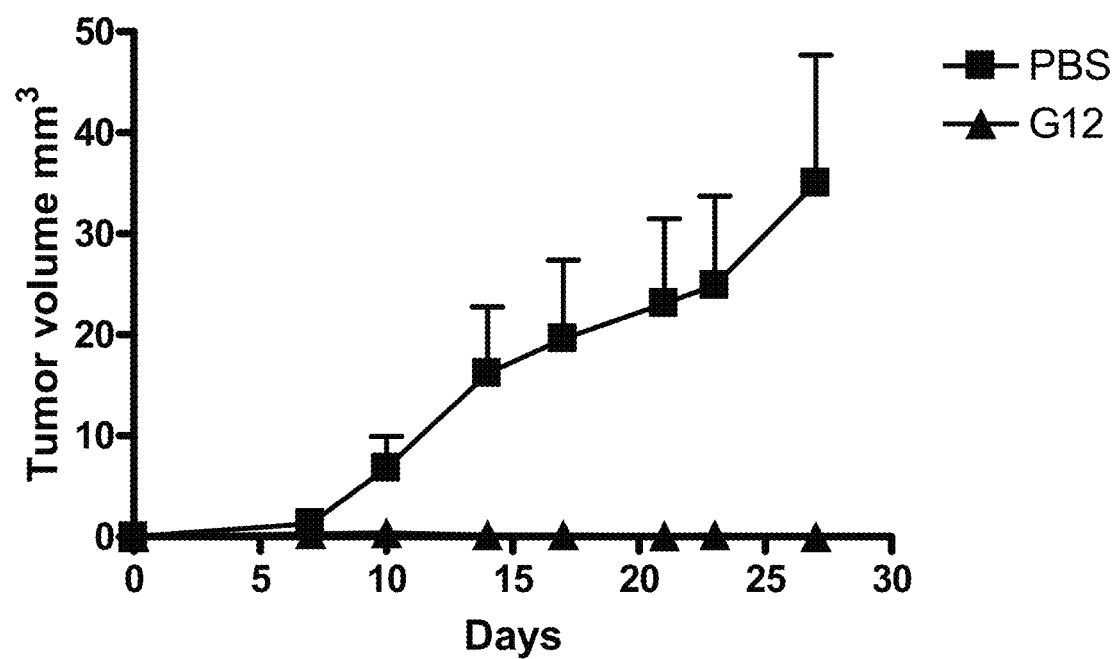

FIG. 9—The average (n=10) tumour volume of the treatment groups is displayed (+/−SEM). The mice was treated with 30 ug G12 and compared to PBS-treatment in the precence of human dendritic cells and T cells, whereach treatment group (n=10) grafted with autologous T cells and dendritic cells from two different donors (five mice for each donor, in total ten mice). Treatment with G12 is significant compared to the isotype control.

Figure 10:
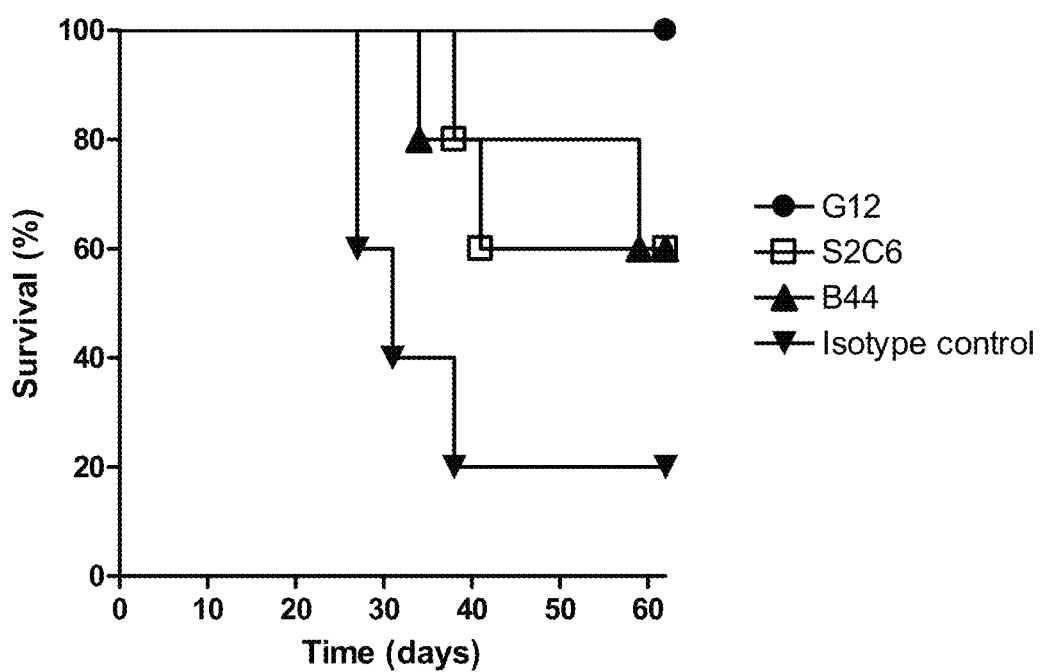

FIG. 10—Survival curves of tumour inoculated mice treated with drug are shown. Treatment with G12 significantly increases the survival of animals compared to isotype control (p<0.013). The survival curve of mice treated with G12 compared to S2C6 (p<0.13). The survival of mice treated with S2C6 compared to isotype control (p<0.088). Each treatment group consisted of 5 mice, N=5.

Figure 11:
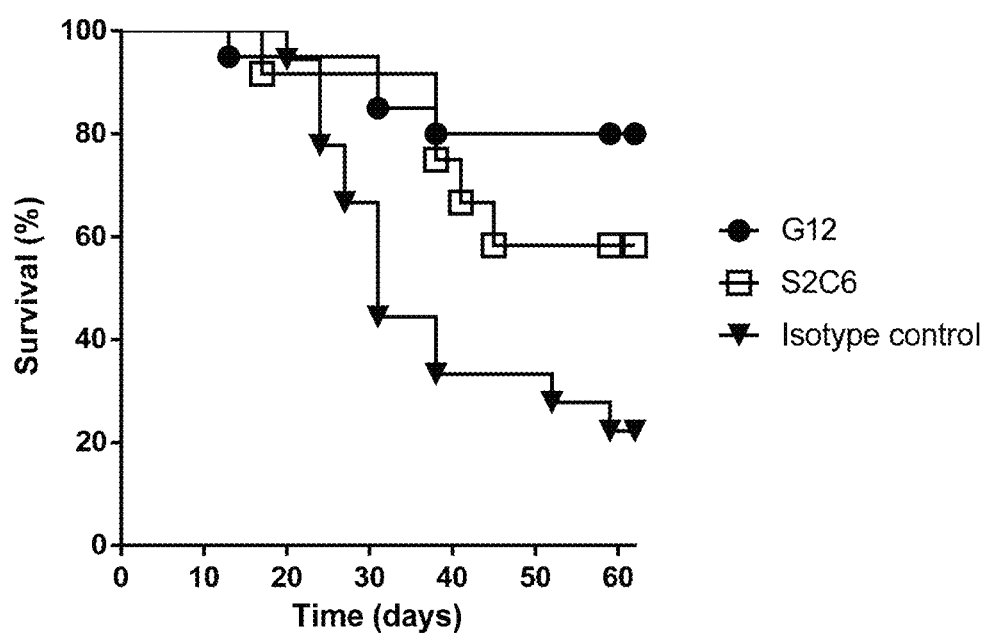

FIG. 11—Survival curves of tumour-bearing mice treated with drug are shown. The displayed survival curves are based on pooled data. The group of treated mice with G12 and isotype control consisted of 20 animals in each of the group. The mice treated with S2C6 consisted of 12 animals. The survival curve of the G12 treated group and the S2C6 treated group was compared to the isotype control treated group by log rank test using Bonferroni method to adjust for multiple comparisons. The survival curve of G12 is significantly different compared to the isotype control (unadjusted p 0.004).

Figure 12:
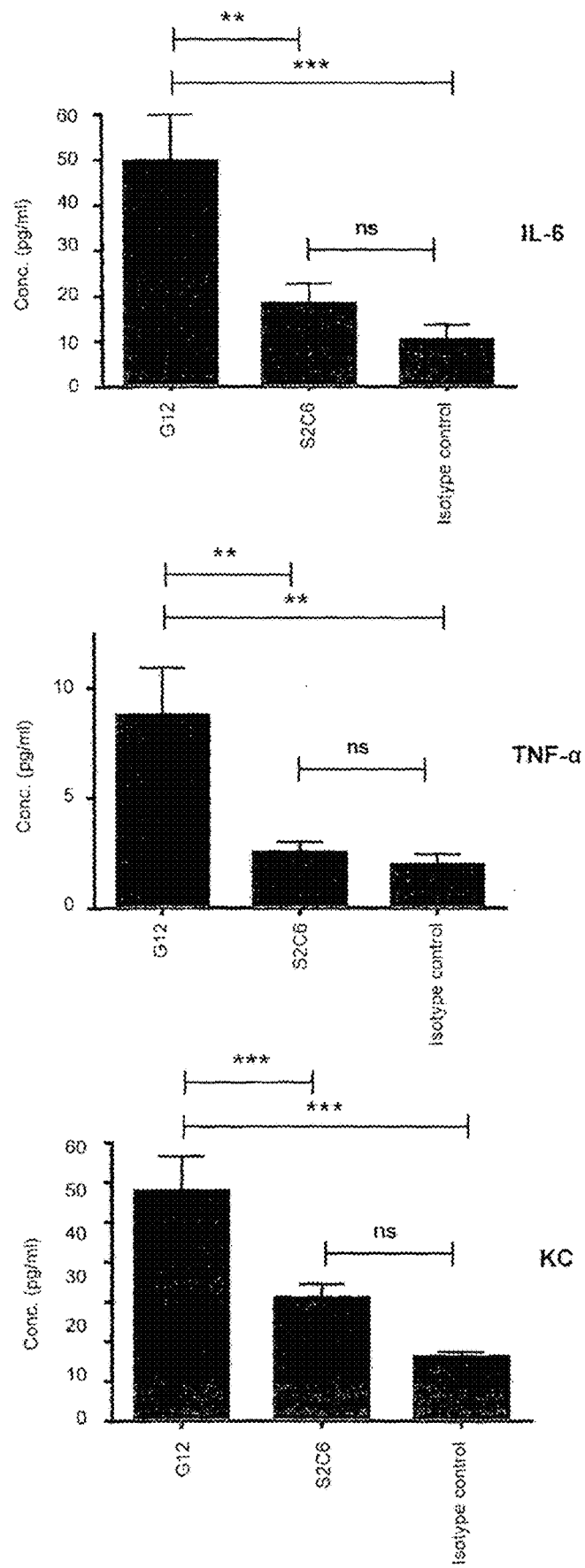

FIG. 12—The cytokine levels in treated mice are displayed. Serum samples were taken 4 h after second treatment on day 10 from treated mice and were analysed for cytokine levels. The cytokine levels from mice treated with G12, S2C6 and isotype control was compared using one-way Anova with Bonferroni's multiple comparisons test to calculate adjusted p values. Treatment with G12 is significant compared to the S2C6 treated mice. The cytokine levels marked with * displayed a p<0.001, data marked with  displayed a p value of 0.001<p<0.01, and cytokine levels marked * displayed a p value of 0.01<p<0.05. The G12 treatment group and S2C6 treatment group consisted of 23 mice, N=23. The treatment group of the isotype control consisted of 18 mice, N=18.

Figure 13:
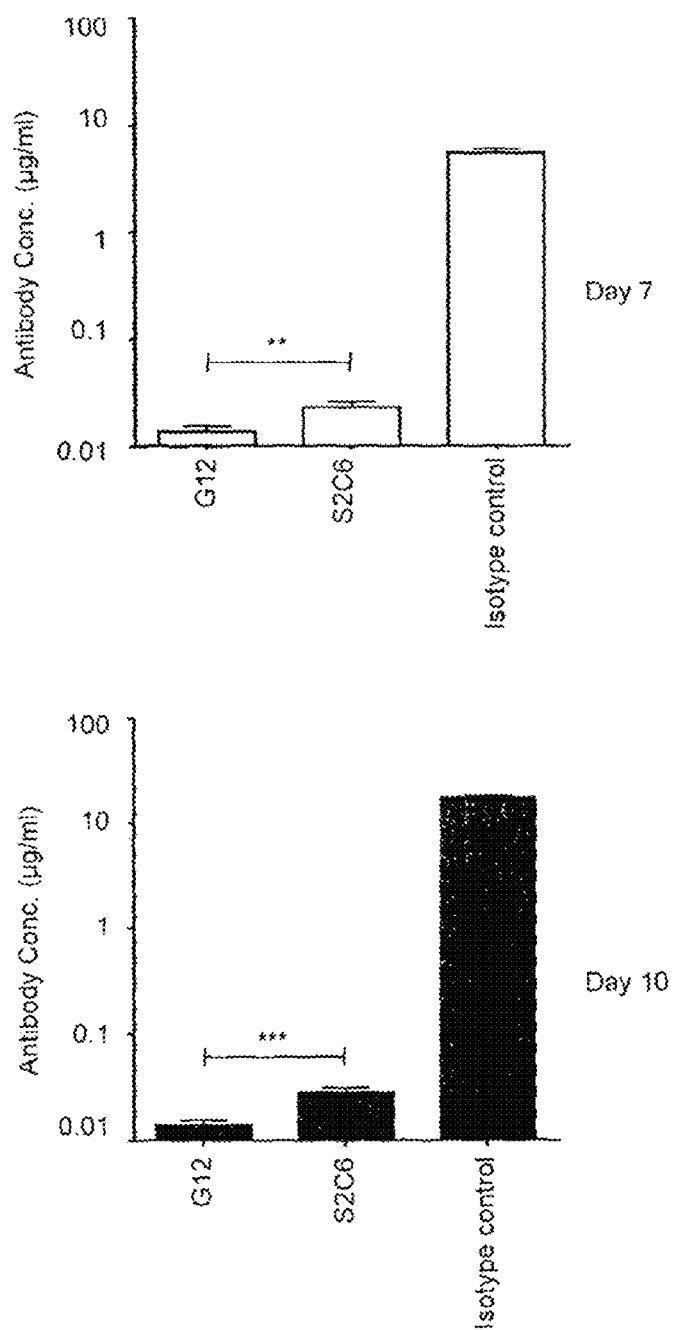

FIG. 13—Antibody levels in serum from treated mice. Serum samples taken 4 h after the first (day 7) and the second (day 10) treatment with G12 or controls were analyzed for antibody levels. At day 7 and 10, the antibody titer was significantly lower, approximately two-fold, for the anti-CD40 antibody clone G12 compared to clone S2C6. A one tailed unpaired t-test was used to calculate the p value for the comparison of the means of G12 and S2C6. The serum G12 titer was approximately 100 fold lower compared to isotype control due to target related effects, (the G12 titer is similar to the isotype titer in human CD40 negative mice).

After treatment with identical doses (30 g) G12 and S2C6 there is a significant difference in serum titers of G12 and S2C6 4 hour post treatment. This indicates that G12 is retained longer in the tumour and surrounding tissue compared to S2C6. This difference may be a result of G12's high on-rate and affinity to the target (CD40) compared to other CD40 antibodies, eg. S2C6.

The antibody levels marked with * displayed a p<0.001, data marked with  displayed a p value of 0.001<p<0.01. The G12 treatment group and S2C6 treatment group consisted of 23 mice, N=23. The treatment group of the isotype control consisted of 18 mice, N=18.

EXAMPLES

Example 1—Directed Evolution of an Agonistic CD40 Antibody with Improved Potency Introduction The B44 antibody originates from the n-CoDeR® library, which is a human antibody fragment display library (Söderlind et al., 2000). The amino acid sequences and a structure model of the anti-CD40 agonistic antibody B44 was used to design the libraries, except for one library, in which random mutations were inserted throughout the entire sequence.

Antibodies of the invention were prepared and selected as follows.

Library Design

Three designed libraries and one random library were constructed based on sequence analysis and structure modelling of the B44 antibody. The structure model of B44 was based on suitable template structures, 1NL0 for VH and 2J6E for VL, in the protein data bank (PDB).

In AL-10013-04, the germ-line hot spot residues (see LeFranc et al, IMGT/VQEST, www.imgtorg/IMGTeducation/Tutorials/IGandBcells/_UK/SomaticHypermutations) in B44 were identified by nucleotide sequence analysis (Ho and Pastan "Therapeutic antibodies: Methods and protocols", 2009, (525) Humana Press). Germline hot spot mutations are amino acid positions in rearranged variable immunoglobulin domains that are prone to undergo mutations during the somatic hypermutation process. The Germline hot spot residues in CDRL3 were randomized along with selected germ-line hot spot residues in the structurally adjacent CDRL1. The variability in each of the germline hot spot mutations was restricted to 8-9 selected residues to reduce the complexity and generating a highly functional library. These residues was selected to represent the physiochemical properties of all (20) of the naturally occurring amino acids (Tanping, Protein Engineering, 2003, 16, 323-330) (Koide et al, 2009, ACS Chemical biology), while keeping the complexity and theoretical variability on a convenient level. The theoretical variability of this library was $1.9 \times 10^7$ individual variants.

In AL-10013-05, all surface exposed CDR-residues were identified based on the structure model of B44. These residues were varied, restricting the variability to 1 or two homologous residues, except in H3 where additional variability was introduced (see FIG. 1). The purpose was to create a highly functional library, while keeping the complexity and theoretical variability on a convenient level. The theoretical variability of this library was $1.9 \times 10^7$ individual variants.

In the designed library AL-10013-06, residues in the central part of CDRL3 and residues in the structurally-adjacent CDRH2 were randomized (n=11). The residues were identified from the structure model of B44. The variability in each position was restricted to 4-5 residues selected to represent physiochemical properties suitable for generating a high affinity, "minimalist", protein binding epitope (Koide et al 2009, ACS Chemical biology, Fellouse et al., 2007, *J Mol Biol*)[1, 2], while retaining the complexity and theoretical variability on a convenient level. The AL-10013-06 library contain $1.6\ 10^7$ unique variants.

In the randomized library AL-10013-07, the entire B44 sequence was randomized using an error-prone PCR method designed to minimize mutational bias (Genemorph). The generated size of the library was $6.3 \times 10^8$ unique variants.

Selection Strategy

The starting libraries were enriched for binders to biotinylated CD40-Fcγ, thereby creating a pool of sequences from each library which encoded functional binders ("Round 1" in Table 1). The initial enrichment for binders was verified by sequencing.

The pools of sequences encoding functional variants were subsequently recombined using FIND®. The FIND® technology of Alligator Bioscience AB is described in WO 02/48351 and WO 03/097834.

The FIND®-recombined library comprised $2 \times 10^8$ unique variants.

The produced FIND®-recombined library was subjected to four rounds of additional selection ("Rounds 2 to 5" in Table 1).

From each selection round, approximately 2,000 clones were selected and screened in a high through-put assay. The selection protocol for affinity maturation included steps impacting the following properties: affinity; on-rate; off-rate; multimerization; and epitope maintenance.

In order to increase affinity, a ten-fold lowering of the antigen-concentration in three rounds, followed by a five-fold lowering of antigen concentration in two rounds, was included.

The on-rate was designed to be retained, and was addressed by shortening the incubation time.

The off-rate was designed to be improved by increasing washing stringency. Unbiotinylated CD40 was included in rounds 4 and 5 to prevent mulitmerization and to suppress selection for avidity.

Results from the selection to primary high through put screening are summarised in "heat maps" of libraries, which show the position and frequency of mutations generated in each library (FIG. 1A).

Figure 1B:
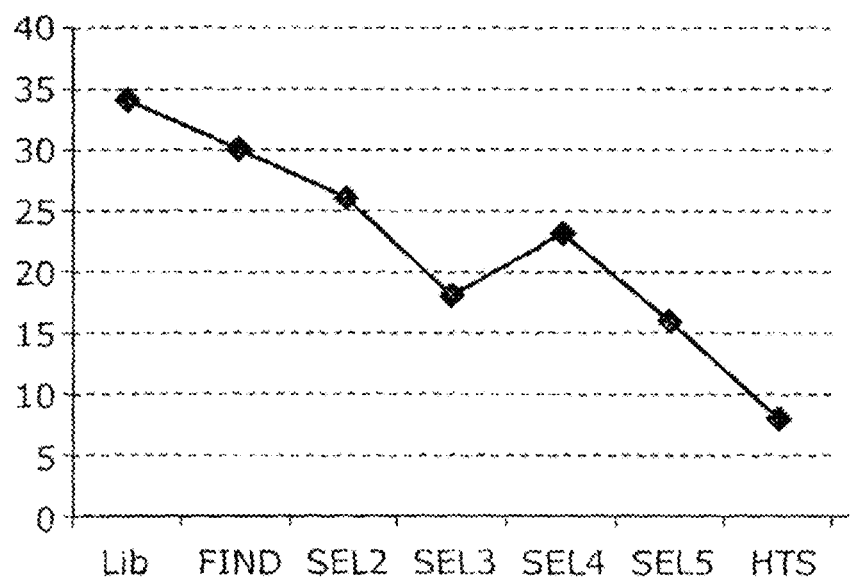

FIG. 1B demonstrates how the FIND® recombination technology decreases the number of mutated residues while still improving the affinity.

TABLE 1

| | | Selection strategy | |
|---|---|---|---|
| Round | Ag conc (nM) | Incubation (min)[a] | Wash (min)[b] |
| 1 | 10 | 60/30 | Standard |
| 2 | 1 | 20/30 | Standard |
| 3 | 0.1 | 10/20 | Standard + 10 |
| 4 | 0.02 | 5/10/20 | Standard + 30 |
| 5 | 0.004 | 5/10/15 | Standard + 120 |

[a]the incubation time is shown for: Incubation time with biotinylated CD40/additional incubation time with non-biotinylated CD40 in round 4 and 5/incubation time allowed to rescue the phage/antigen complexes on magnetic beads.
[b]The standard wash comprised seven wash of using selection buffer (PBS-T/BSA) followed by four washes with PBS. The protocol was extended in round 3-5 adding a prolonged incubation (time given in minutes).

High Throughput Screening (HTS)

From each selection round, approximately 2,000 clones were selected and screened in a high throughput assay.

The high throughput screening assay was designed as follows: a method for measuring the off-rate at two different washing conditions in a direct binding ELISA was performed. Improved off-rate correlated to increased ratio of the two measurements. The results from the high-through-put assay was plotted measured ratio versus binding signal in ELISA (FIG. 2).

The HTS assay was based on a sandwich ELISA measuring binding of ScFv-his fragment in crude *E. coli* supernatants to CD40 coated in microtitre plates.

White 394-plate flat bottom high binding (Greiner #781074) was coated with CD40mFc (Apollo #9025H) by incubate 2 h at room temperature or overnight at 4° C. The plates were washed (Wash buffer: PBS+0.05% Tween 20 (PBST), Medicago #09-9410-100, ELx405 micro-plate washer (BioTek) and then blocked in PBST+3% Milk powder (Semper). The plates were washed again and sample or controls were added to the wells. The samples were incubated for 1 h at room temperature and then washed using either a normal wash (3 wash cycles) or harsh wash (3 wash cycles followed by incubation with PBST 30 min followed by 3 wash cycles).

Detection Ab, Penta-His-HRP (Qiagen #1014992) was added and the plates were subsequently developed using SuperSignal Pico Chemiluminescent substrate (Thermo #37069) and detected with Envision reader (Perkin Elmer).

Example 2—Improved Affinity of Exemplary Anti-CD40 Antibodies

The FIND® recombined anti-CD40 antibodies were selected for having improved affinity (KD) to the CD40 receptor. The affinity of the anti-CD40 antibodies to target was determined by surface plasmon resonance and calculated kinetic constants are shown in Table 1 and Table 2. The affinities were improved approximately a hundred-fold for the anti-CD40 antibody clones compared to the original B44 antibody, Table 2 and FIG. 3, at physiological pH and 37° C.

The improved affinity by the anti-CD40 antibody clones were also observed at a low pH, Table 2. Surface plasmon resonance was used to determine the kinetic constants at pH 5.4 and 37° C., and compared to the B44 antibody.

The results show that the overall affinities were only moderately affected by lowering the pH to 5.4, and that the increase in affinity compared to B44 remains (although off-rates and on-rates were changed individually). This may be of clinical benefit for local immunotherapy using the invention.

Materials and Methods

Determination of Kinetic Parameters and Affinity Constants as Identified by Surface Plasma Resonance The affinity measures of purified antibodies by surface plasmon resonance using the Biacore 3000 instrument was performed according to manufacturer's protocols.

The CD40hfc (R&Dsystems, USA) was immobilized to the BIAcore sensorchip, CM5, using conventional amine coupling. The anti-CD40 antibodies of the invention, (serially diluted 1/3 from 1-0.012 nM) were analysed for binding in HBS-P (GE, BR-1003-68) at a flow rate of 30 µl/min at 37° C. and pH 7.3. The association was followed for 3 minutes and the dissociation for 10 minutes. Regeneration was performed twice using 50 mM NaOH for 30 seconds. The kinetic parameters and the affinity constants were calculated using BIAevaluation 4.1 software.

Alternatively, samples were incubated in Acetate buffer pH 5.4, 10 mM Acetate, 150 mM NaCl, 0.005% T20, at 37° C.

Results are shown in Tables 2 and 3.

Results

TABLE 2

Kinetic constants for the interaction between immobilized CD40 receptor and anti-CD40 antibody clones compared to B44 at physiological pH as determined by surface plasmon resonance.

| Antibody | ka (1/Ms) | kd (1/s) | KD (M) |
|---|---|---|---|
| B44 | $2.7 \times 10^6$ | $4.5 \times 10^{-3}$ | $1.7 \times 10^{-9}$ |
| A4 | $7.3 \times 10^6$ | $7.6 \times 10^{-5}$ | $1.0 \times 10^{-11}$ |
| A5 | $8.5 \times 10^6$ | $9.6 \times 10^{-5}$ | $1.1 \times 10^{-11}$ |
| F6 | $11 \times 10^6$ | $3.2 \times 10^{-5}$ | $3.0 \times 10^{-11}$ |
| F9 | $2.8 \times 10^6$ | $1.2 \times 10^{-5}$ | $4.3 \times 10^{-11}$ |
| G12 | $9.6 \times 10^6$ | $2.0 \times 10^{-4}$ | $2.0 \times 10^{-11}$ |
| H12 | $11 \times 10^6$ | $4.9 \times 10^{-5}$ | $4.5 \times 10^{-11}$ |
| B9 | $8.5 \times 10^6$ | $1.2 \times 10^{-4}$ | $1.4 \times 10^{-11}$ |
| C4 | $7.5 \times 10^6$ | $5.4 \times 10^{-5}$ | $7.2 \times 10^{-11}$ |
| H11 | $8.5 \times 10^6$ | $1.3 \times 10^{-4}$ | $1.6 \times 10^{-11}$ |

TABLE 3

Kinetic constants for the interaction between immobilized CD40 receptor and anti-CD40 antibody clones compared to B44 at pH = 5.4 as determined by surface plasmon resonance.

| Antibody | ka (1/Ms) | kd (1/s) | KD (M) |
|---|---|---|---|
| B44 | $6.0 \times 10^6$ | $5.5 \times 10^{-3}$ | $9.3 \times 10^{-10}$ |
| A4 | $1.1 \times 10^7$ | $2.2 \times 10^{-4}$ | $2.0 \times 10^{-11}$ |
| A5 | $1.1 \times 10^7$ | $2.5 \times 10^{-4}$ | $2.2 \times 10^{-11}$ |
| G12 | $9.6 \times 10^6$ | $2.0 \times 10^{-4}$ | $2.0 \times 10^{-11}$ |
| H12 | $11 \times 10^6$ | $4.9 \times 10^{-5}$ | $4.5 \times 10^{-11}$ |
| B9 | $9.7 \times 10^6$ | $3.2 \times 10^{-4}$ | $3.3 \times 10^{-11}$ | ka, association rate constant;
kd, dissociation rate constant,
KD, affinity constant Example 3—Epitope Mapping and Cross-Reactivity of the Exemplary Antibodies of the Invention The CD40 receptor consists of four extracellular domains, each composed of two types of modular units (Naismith and Sprang, 1998, *Trends Biochem*, (23) 74-79) and each module is stabilised by one or two disulfide bonds. In order to analyse the fine specificity of the selected scFv, the location of each scFv epitope was determined by domain mapping. The ability of the scFv fragments to bind to truncated CD40-constructs, expressed on the surface of transfected COS-7 or L-cells were measured using FACScan analysis (as described by Ellmark et al 2002, Immunology). The exemplary antibodies of the invention were able to bind constructs were the first module had been removed (D1/B2), but not to constructs were the whole first domain of CD40 had been removed (see FIG. 4 and Table 4).

TABLE 4

|  | G12 | A4 | A5 | C4 | B44 | H11 |
|---|---|---|---|---|---|---|
| D1 | + | + | + | + | + | + |
| D1/B2 | + | + | + | + | + | + |
| D2 | − | − | − | − | − | − |
| D2/B1 | − | − | − | − | − | − |
| D3 | − | − | − | − | − | − |

Cross-Specificity

The antibody clones of the invention cross-react with CD40 from cynomolgus monkey, rhesus macaque and other relevant macaque-species. They do not cross react with murine or canine CD40.

Example 4—Up-Regulation of Dendritic Cell Surface Molecules by Exemplary Anti-CD40 Antibodies The ligation of the CD40 receptor induces activation of Dendritic cells, which potentially leads to activation of a specific anti-tumour T-cell response. Monocyte-derived Dendritic cells treated with an anti-CD40 antibody display up-regulated expression of surface molecules CD80, CD83, CD86, and HLA-DR. The up-regulation of the surface molecules, CD80 and CD86, are required in the co-stimulation of T-cell activation.

Other agonistic CD40 antibodies, e.g. CP-870,893, have an approximately 20-fold higher potency for B cell activation than for activation of Dendritic cells (Gladue et al., 2011, *Cancer Immunol Immunother* 60[7]; 1009-1017).

The activation of Dendritic cells is more clinically relevant than B-cell activation, and the effect on B cells may result in dose limiting toxicity at a treatment dose that do not activate Dendritic cells. It is thus advantageous to improve the potency for activation of Dendritic cells, while keeping the potency for B cell activation in the same range. The clones described in the invention have a potency for B cell activation that is in the same range as activation of Dendritic cells, which may provide clinical advantages.

The improved potency of the anti-CD40 antibody clones to promote activation of Dendritic cells in comparison to the original anti-CD40 antibody, B44, was determined by in vitro assays. An improved potency was observed for anti-CD40 antibody clones in Dendritic cell activation as determined by up-regulation of the surface molecules CD86.

Tables 5 summarises the results from these expression studies of surface markers.

In FIGS. 5 A and B, the expression of CD86 and its concentration dependence is shown.

Materials and Methods

Dendritic Cell Activation Assay

Dendritic cells were derived from peripheral blood monocytes. Briefly, peripheral blood mononuclear cells (PBMC) were separated from whole blood buffy coats of whole blood by Ficoll gradient and CD14+ monocytes were isolated with CD14+ MACS microbeads (Miltenyi) according to manufacturer's instructions. The CD14+ cells, which reached ~95% purity were cultured in RPMI medium +10% FCS, 150 ng/ml GM-CSF and 50 ng/ml IL-4 at 37° C. for six days at a concentration of 1×10⁶ cells/ml. 80% of the medium were replaced with fresh medium and cytokines after three days culture.

After six days in culture the cells had down regulated CD14 and up-regulated CD1a. They were washed, re-suspended in medium with fresh cytokines and dilution series of stimulating antibodies. Cells were cultured at a concentration of 667000 cells/ml and antibodies from 3.3-0.013 µg/ml. Stimulating antibodies were B44 and eight clones A4, A5, B9, C4, F6, G12, H11 and H12. The Dendritic cells were cultured at 37° C. for an additional 48 hours. Then, the up-regulation of the activation markers CD86, CD80 and HLA-DR were analysed by FACS.

TABLE 5

The mean EC50 and maximum fold increase of CD86, CD80, and MHC II expression of clones of the invention and B44.

|  | G12 ANTI-CD40 ANTIBODY EC50 (µg/ml) (mean +/− st.d.) | G12 ANTI-CD40 ANTIBODY Maximum Fold Increase (mean +/− st.d.) |
|---|---|---|
| CD86 | 0.09 +/− 0.056 | 136 +/− 72.6 |
| CD80 | 0.09 +/− 0.056 | 292 +/− 205 |
| MHC II | 0.14 +/− 0.078 | 864 +/− 450 |

|  | A4 ANTI-CD40 ANTIBODY EC50 (µg/ml) (mean +/− st.d.) | A4 ANTI-CD40 ANTIBODY Maximum Fold Increase (mean +/− st.d.) |
|---|---|---|
| CD86 | 0.13 +/− 0.08 | 149 +/− 79.5 |
| CD80 | 0.17 +/− 0.047 | 599 +/− 87.8 |
| MHC II | 0.14 +/− 0.08 | 851 +/− 485 |

|  | C4 ANTI-CD40 ANTIBODY EC50 (µg/ml) (mean +/− st.d.) | C4 ANTI-CD40 ANTIBODY Maximum Fold Increase (mean +/− st.d.) |
|---|---|---|
| CD86 | 0.11 +/− 0.050 | 164 +/− 101 |
| CD80 | 0.031 +/− 0.0007 | 609 +/− 136 |
| MHC II | 0.04 +/− 0.014 | 395 +/− 252 |

|  | H11 ANTI-CD40 ANTIBODY EC50 (µg/ml) (mean +/− st.d.) | H11 ANTI-CD40 ANTIBODY Maximum Fold Increase (mean +/− st.d.) |
|---|---|---|
| CD86 | 0.14 +/− 0.056 | 195 +/− 88 |
| CD80 | 0.14 +/− 0.056 | 641 +/− 37 |
| MHC II | 0.22 +/− 0.15 | 481 +/− 122 |

|  | B44 ANTI-CD40 ANTIBODY EC50 (µg/ml) (mean +/− st.d.) | B44 ANTI-CD40 ANTIBODY Maximum Fold Increase (mean +/− st.d.) |
|---|---|---|
| CD86 | 0.37 +/− 0.21 | 132 +/− 81 |
| CD80 | 0.25 +/− 0.14 | 584 +/− 73 |
| MHC II | 0.51 +/− 0.20 | 811 +/− 684 |

Example 5—Enhanced IFN-γ Secretion by Activated T Cells Induced by Exemplary Anti-CD40 Antibodies The in vitro T cell activation by Dendritic cells stimulated by the anti-CD40 antibodies clones was studied and the IFNγ-production was analysed.

The results are summarized in Table 6.

The potency of the anti-CD40 antibody clones was improved compared to the B44 antibody in the allogenic T cell and Dendritic cell assay.

Materials and Methods

Assay for Allogenic T Cell Activation by Dendritic Cells

Dendritic cells were derived from peripheral blood monocytes as described in the Dendritic cell activation assay.

After six days, the Dendritic cells were washed, re-suspended in medium with fresh cytokines and cultured in presence of T cells from a different donator. T cells were isolated from PBMCs with CD3+ MACS microbeads (Miltenyi) according to manufacturer's instructions.

The concentrations of Dendritic cells and T cells in the T cell activation assay were 667,000 cells/ml of each cell-type. Furthermore, the co-culture contained 150 ng/ml GM-CSF and 50 ng/ml IL-4 and dilution series of stimulating antibodies from 3.3-0.013 µg/ml. Stimulating antibodies were B44 and eight clones A4, A5, B9, C4, F6, G12, H11 and H12. The co-culture was incubated at 37° C. for additionally 72 hours. Then, the supernatants were analysed for IFN-γ content by ELISA (Biolegends) according to manufacturer's instructions.

TABLE 6

Enhancement of IFN-γ secretion by anti-CD40 antibodies of the invention compared to the B44 antibody.

| | Allo DC/T IFN-γ | |
|---|---|---|
| Antibody | EC50 µg/ml | Max (pg/ml) |
| B44 | 0.2 | 8.7 |
| A4 | 0.04 | 8.9 |
| A5 | 0.08 | 9.5 |
| B9 | 0.03 | 8.5 |
| C4 | 0.12 | 9 |
| F6 | 0.15 | 9 |
| G12 | 0.05 | 9.1 |
| H11 | 0.03 | 9.5 |

Example 6—Comparison of B Cell Activation by Exemplary Anti-CD40 Antibodies

Binding of agonistic anti-CD40 antibodies to CD40 on B-cells results in B cell activation and proliferation, homeotypic aggregation and up-regulation of surface markers such as CD23, CD30, CD80, CD86, Fas, major histocompatibility complex (MHC) II and soluble cytokines, e.g. IL-6, TNF-α and TNF-β (Schönbeck and Libby, 2001, Cell Mol Life 58(1), 4-43).

Measuring CD40 induced B cell proliferation is commonly used to evaluate CD40 agonistic antibodies (Pound et al, 1999, Int Immunol, (11), 11-20).

Material and Methods

Peripheral blood mononuclear cells (PBMC) were separated from whole blood buffy coats of whole blood by Ficoll gradient and CD19+B cells were isolated with CD19+ MACS microbeads (Miltenyi) according to manufacturer's instructions. The CD19+ cells (5-7.5×10⁴/well), which reached ~95% purity were cultured in RPMI medium+10% FCS+10 ng/ml IL4 and dilution series of antibodies. After 48-72 h, the metabolic activity was measured with Cell titer-Glo (Promega). The EC50 values were calculated using Graph Pad prism.

Results

TABLE 7

| Activation of B cells | |
|---|---|
| Antibody | EC50 (ug/ml) +/− SEM |
| B44 | 0.204 +/− 0.025561 |
| A5 | 0.29 +/− 0.0155 |
| B9 | 0.48 +/− 0.0528 |
| C4 | 0.288 +/− 0.06225 |
| F6 | 0.40 +/− 0.04415 |
| F9 | 0.21 +/− 0.0815 |
| H11 | 0.46 +/− 0.0953 |
| H12 | 0.18 +/− 0.003 |
| G12 | 0.098 +/− 0.019657 |
| A4 | 0.16 +/− 0.02395 |

The anti-CD40 antibodies of the invention have similar potency in activating B cells (i.e. of the same order of magnitude) as B44 (see Table 7).

Example 7—Ability of Exemplary Anti-CD40 Antibodies of the Invention to Bind RAMOS Cells The ability of anti-CD40 antibodies of the invention to bind to RAMOS cells was determined in vitro. We performed FACS analysis of the anti-CD40 antibodies binding to the human Burkitt's lymphoma cell line RAMOS. EC50 values were calculated for the anti-CD40 antibodies of the invention and the original B44 anti-CD40 antibody.

Materials and Methods

The human Burkitt's lymphoma cell line RAMOS was used for binding analysis (ECACC, Sigma Aldrich, USA). The unconjugated anti-CD40 antibodies of the invention were assayed for binding to RAMOS cells.

RAMOS cells, approximately 125,000 cells, were incubated with anti-CD40 antibody, serially diluted 1/3 from 30-0.0015 μg/ml, for 30 minutes at 4° C. The cells were washed twice with FACS buffer and the secondary antibody, anti-human Ig Rabbit F(ab')2/FITC (DAKO, Glostrup, Denmark), was subsequently added to the cells for another 30 minutes at 4° C. The cells were washed and analysed on a FACScalibur instrument, according to the manufacturer's instructions (Becton Dickinson, USA) and then the mean fluorescent intensity ("MFI") was determined.

Results

The results are shown in Table 8.

The exemplary anti-CD40 antibody clones have approximately a 100-fold increased potency compared to the B44 antibody.

TABLE 8

| Binding of antibody clones to RAMOS cells. | |
|---|---|
| anti-CD40 antibody | EC50 (μg/ml) |
| A4 | $7.0 \times 10^{-3}$ |
| A5 | $6.2 \times 10^{-3}$ |
| B9 | $4.9 \times 10^{-3}$ |
| C4 | $6.1 \times 10^{-3}$ |
| F6 | $5.8 \times 10^{-3}$ |
| G12 | $6.7 \times 10^{-3}$ |
| H11 | $4.4 \times 10^{-3}$ |
| H12 | $8.9 \times 10^{-3}$ |
| B44 | 0.38 |

Example 8—Effect of Exemplary Antibodies In Vivo in Mouse Tumour Model

The anti-tumour activity of the exemplary anti-CD40 antibodies of the invention was studied in a NSG mouse model in the absence and in the presence of T cells and dendritic cells.

(A) Study Using CD40 Positive Tumours in the Absence of T Cells and Dendritic Cells Materials & Methods We obtained female NSG mice (NOD.Cg-Prkdc$^{scid}$ II2rg$^{tm/Wjl}$/SzJ (NSG)) from Jackson, and allowed them to acclimatize before treatment. Bladder cancer cells, (EJ-cells, $3 \times 10^6$ cells/mouse) were injected subcutaneously. G12, or isotype control was injected intratumourally day 0, 7 and 14 at a dose of 1.2 mg/kg (30 ug). The tumour volume was measured at day 0, 7, 10, 14, 17, 21, 23 and 27. The tumours was excised and weighed at day 28.

Results

The results are shown in FIGS. 6 and 7.

(B) Study Using CD40 Positive Tumours in the Presence of T Cells and Dendritic Cells Materials & Methods We obtained female NSG mice (NOD.Cg-Prkdc$^{scid}$ II2rg$^{tm/Wjl}$/SzJ (NSG)) from Jackson, and allowed them to acclimatize before treatment. Bladder cancer cells, (EJ-cells, $2.5 \times 10^6$ cells/mouse) were injected subcutaneously together with DC ($1 \times 10^5$) and T cells ($5 \times 10^5$) obtained from the same donor. The dendritic cells were prepared from monocytes (as described above). Each treatment group consisted of 10 mice (n 10), where T cells and DCs from two donors was used in five mice/donor (see Table 9).

TABLE 9

| Test substance | Human moDC/Tcells (donor) | Number of mice |
|---|---|---|
| PBS | Donor 1 | 5 |
| | Donor 2 | 5 |
| G12 | Donor 1 | 5 |
| | Donor 2 | 5 |

G12, or PBS control was injected intratumourally day 0, 7 and 14 at a dose of 1.2 mg/kg (30 ug). The tumour volume was measured at day 0, 7, 10, 14, 17, 21, 23 and 27. The tumours was excised and weighed at day 28.

Results

The results are shown in FIGS. 8 and 9.

Example 9—Ability to Rescue Cells from Apoptosis

The ability of the anti-CD40 antibodies to rescue cells expressing human CD40 from apoptosis and growth arrest was performed in vitro. Apoptosis and growth arrest was induced in transfected WEHI-231 cells by addition of anti-IgM antibodies. The cells were rescued by addition of anti-CD40 antibody. Subsequently to this, the ability of the cells to proliferate was determined.

An improved potency, up to 40 times, was observed for the anti-CD40 antibody clones relative to the B44 antibody—see Table 9.

Materials and Methods

Rescue from Apoptosis:

A stable cell line was transfected with human CD40, huCD40/WEHI-231, and used for investigating rescue from apoptosis and growth arrest (Ellmark et al., 2003, Immunology, 108, 452-7). The cells, huCD40/WEHI-231, were cultured in a 96-well plate (2×10⁴ cells/well) in the presence or absence of anti-mouse IgM, (Jackson Immunoresearch, USA), and an anti-CD40 antibody of the invention, serially diluted 1/3 from 25-0.0001 μg/ml, for 72 hours. Cell titer-Glo was added and the mixture was incubated for 30 minutes at room temperature (Promega, USA). The cells were assayed for proliferation by measuring ATP release. Luminescence signal was measured in FluoSTAR OPTIMA and the signal was normalized (BMG, Germany)

TABLE 10

Ability of antibody clones to rescue cells from apoptosis and growth arrest.

| anti-CD40 antibody clone | Fold change in potency versus B44 antibody |
|---|---|
| G12 | 19 |
| A4 | 46 |
| A5 | 19 |
| B9 | 38 |
| C4 | 52 |

Example 10: Summary of Sequence Information

For each antibody described below, $V_L$ amino acid positions 1-112 and $V_H$ amino acid positions 1-119 are shown, along with the corresponding nucleotide sequence. CDRs are underlined in the amino acid sequences—in the $V_L$ amino acid sequence, CDRs are found at amino acid positions 23-40 (CDR1), positions 52-58 (CDR2) and 90-101 (CDR3); in the $V_H$ amino acid sequence, CDRs are found at amino acid positions 26-35 (CDR1), positions 42-67 (CDR2) and 97-108 (CDR3).

```
Antibody B44
Variable light chain (V_L) amino acid sequence
                                          SEQ ID NO: 58
QSVLTQPPSASGTPGQRVTISCTGSSSNIGAGYDVYWYQQLPGTAPKLLI

YGNINRPSGVPDRFSGSKSGTSASLAISGLRSEDEADYYCAAWDDSLSGL

VFGGGTKLTVLG

Variable light chain (V_L) nucleotide sequence
                                          SEQ ID NO: 59
CAGTCTGTGCTGACTCAGCCACCCTCAGCGTCTGGGACCCCCGGGCAGAG

GGTCACCATCTCTTGCACTGGGAGCAGCTCCAACATCGGGGCAGGTTATA

ATGTATACTGGTATCAGCAGCTCCCAGGAACGGCCCCCAAACTCCTCATC

TATGGTAACATCAATCGGCCCTCAGGGGTCCCTGACCGATTCTCTGGCTC

CAAGTCTGGCACCTCAGCCTCCCTGGCCATCAGTGGGCTCCGGTCCGAGG

ATGAGGCTGATTATTACTGTGCAGCATGGGATGACAGCCTGAGTGGTCTG

GTTTTCGGCGGAGGAACCAAGCTGACGGTCCTAGGT

Variable heavy chain (V_H) amino acid sequence
                                          SEQ ID NO: 60
EVQLLESGGGLVQPGGSLRLSCAASGFTFSTYGMHWVRQAPGKGLEWLSY

ISGGSSYIFYADSVRGRFTISRDNSENALYLQMNSLRAEDTAVYYCARIL

RGGSGMDLWGQGTLVTVSS

Variable heavy chain (V_H) nucleotide sequence
                                          SEQ ID NO: 61
GAGGTGCAGCTGTTGGAGTCTGGGGGAGGCTTGGTACAGCCTGGGGGGTC

CCTGAGACTCTCCTGTGCAGCCTCTGGATTCACCTTCAGTACTTATGGCA

TGCACTGGGTCCGCCAGGCTCCAGGGAAGGGGCTGGAGTGGCTTTCATAT

ATTAGTGGTGGTAGTAGTTACATTTTCTACGCAGACTCAGTGAGGGCCG

ATTCACCATCTCCAGAGACAACTCCGAGAACGCGCTGTATCTGCAAATGA

ACAGCCTGAGAGCCGAGGACACGGCCGTGTATTACTGTGCGAGAATATTA

AGAGGCGGGAGCGGTATGGACCTCTGGGGCCAAGGTACACTGGTCACCGT

GAGCTCA

Antibody clone A4
Variable light chain (V_L) amino acid sequence
                                          SEQ ID NO: 19
QSVLTQPPSASGTPGQRVTISCTGSTSNIGAGYKVYWYQQLPGTAPKLLI

YGNINRPSGVPDRFSGSKSGTSASLAISGLRSEDEADYYCAAWDDSLSGL

VFGGGTKLTVLG

Variable light chain (V_L) nucleotide sequence
                                          SEQ ID NO: 40
CAGTCTGTGCTGACTCAGCCACCCTCAGCGTCTGGGACCCCCGGGCAGAG

GGTCACCATCTCTTGCACTGGGAGCAGCTCCAACATCGGGGCAGGTTATA

ATGTATACTGGTATCAGCAGCTCCCAGGAACGGCCCCCAAACTCCTCATC

TATGGTAACATCAATCGGCCCTCAGGGGTCCCTGACCGATTCTCTGGCTC

CAAGTCTGGCACCTCAGCCTCCCTGGCCATCAGTGGGCTCCGGTCCGAGG

ATGAGGCTGATTATTACTGTGCAGCATGGGATGACAGCCTGAGTGGTCTG

GTTTTCGGCGGAGGAACCAAGCTGACGGTCCTAGGT

Variable heavy chain (V_H) amino acid sequence
                                          SEQ ID NO: 31
EVQLLESGGGLVQPGGSLRLSCAASGFTFSTYGMHWVRQAPGKGLEWLSY

ISGGSSYIFYADSVRGRFTISRDNSENALYLQMNSLRAEDTAVYYCARIL

RGGSGMDLWGQGTLVTVSS

Variable heavy chain (V_H) nucleotide sequence
                                          SEQ ID NO: 49
GAGGTGCAGCTGTTGGAGTCTGGGGGAGGCTTGGTACAGCCTGGGGGGTC

CCTGAGACTCTCCTGTGCAGCCTCTGGATTCACCTTCAGTACTTATGGCA

TGCACTGGGTCCGCCAGGCTCCAGGGAAGGGGCTGGAGTGGCTTTCATAT

ATTAGTGGTGGTAGTAGTTACATTTTCTACGCAGACTCAGTGAGGGCCG

ATTCACCATCTCCAGAGACAACTCCGAGAACGCGCTGTATCTGCAAATGA

ACAGCCTGAGAGCCGAGGACACGGCCGTGTATTACTGTGCGAGAATATTA

AGAGGCGGGAGCGGTATGGACCTCTGGGGCCAAGGTACACTGGTCACCGT

GAGCTCA

CDR amino acid sequences
                                          [SEQ ID NO: 4]
V_L CDRs:   CDR1:  CTGSTSNIGAGYKVY

[SEQ ID NO: 10]
            CDR2:  GNINRPS

[SEQ ID NO: 12]
            CDR3:  CAAWDDSLSGLV

[SEQ ID NO: 28]
V_H CDRs:   CDR1:  GFTFSTYGMH
```

```
                        [SEQ ID NO: 29]
        CDR2:  GKGLEWLSYISGGSSYIFYADSVRGR
                        [SEQ ID NO: 30]
        CDR3:  CARILRGGSGMDL
Antibody clone A5
Variable light chain (V_L) amino acid sequence
                        SEQ ID NO: 20
QSVLTQPPSASGTPGQRVTISCTGSSSNIGAGYHVYWYQQLPGTAPKLLI
YGSINRPSGVPDRFSGSKSGTSGSLAISGLRSEDEADYYCAAWDSSSSGL
VFGGGTKLTVLG
Variable light chain (V_L) nucleotide sequence
                        SEQ ID NO: 41
CAGTCTGTGCTGACTCAGCCACCCTCAGCGTCTGGGACCCCGGGCAGAG
GGTCACCATCTCTTGCACTGGGAGCAGCTCCAACATCGGGGCAGGTTATA
ATGTATACTGGTATCAGCAGCTCCCAGGAACGGCCCCCAAACTCCTCATC
TATGGTAACATCAATCGGCCCTCAGGGGTCCCTGACCGATTCTCTGGCTC
CAAGTCTGGCACCTCAGCCTCCCTGGCCATCAGTGGGCTCCGGTCCGAGG
ATGAGGCTGATTATTACTGTGCAGCATGGGATGACAGCCTGAGTGGTCTG
GTTTTCGGCGGAGGAACCAAGCTGACGGTCCTAGGT
Variable heavy chain (V_H) amino acid sequence
                        SEQ ID NO: 32
EVQLLESGGGLVQPGGSLRLSCAASGFTFSTYGMHWVRQAPGKGLEWLSY
ISGGSSYIFYADSVRGRFTISRDNSENALYLQMNSLRAEDTAVYYCARIL
RGGSGMDLWGQGTLVTVSS
Variable heavy chain (V_H) nucleotide sequence
                        SEQ ID NO: 50
GAGGTGCAGCTGTTGGAGTCTGGGGGAGGCTTGGTACAGCCTGGGGGGTC
CCTGAGACTCTCCTGTGCAGCCTCTGGATTCACCTTCAGTACTTATGGCA
TGCACTGGGTCCGCCAGGCTCCAGGGAAGGGGCTGGAGTGGCTTTCATAT
ATTAGTGGTGGTAGTAGTTACATTTTCTACGCAGACTCAGTGAGGGGCCG
ATTCACCATCTCCAGAGACAACTCCGAGAACGCGCTGTATCTGCAAATGA
ACAGCCTGAGAGCCGAGGACACGGCCGTGTATTACTGTGCGAGAATATTA
AGAGGCGGGAGCGGTATGGACCTCTGGGGCCAAGGTACACTGGTCACCGT
GAGCTCA
CDR amino acid sequences
                        [SEQ ID NO: 5]
V_L CDRs:  CDR1:  CTGSSSNIGAGYHVY
                        [SEQ ID NO: 10]
           CDR2:  GNINRPS
                        [SEQ ID NO: 13]
           CDR3:  CAAWDSSSSGLV
                        [SEQ ID NO: 28]
V_H CDRs:  CDR1:  GFTFSTYGMH
                        [SEQ ID NO: 29]
           CDR2:  GKGLEWLSYISGGSSYIFYADSVRGR
                        [SEQ ID NO: 30]
           CDR3:  CARILRGGSGMDL
Antibody clone C4
Variable light chain (V_L) amino acid sequence
                        SEQ ID NO: 21
QSVLTQPPSASGTPGQRVTISCTGSTSNIGAGYKVYWYQQLPGTAPKLLI
YGNINRPSGVPDRFSGSKSGTSASLAISGLRSEDEADYYCAAWDDSLSGL
VFGGGTKLTVLG
Variable light chain (V_L) nucleotide sequence
                        SEQ ID NO: 48
CAGTCTGTGCTGACTCAGCCACCCTCAGCGTCTGGGACCCCGGGCAGAG
GGTCACCATCTCTTGCACTGGGAGCACCTCCAACATCGGGGCAGGTTACA
AAGTATATTGGTATCAGCAGCTCCCAGGAACGGCCCCCAAACTCCTCATC
TATGGTAACATCAATCGGCCCTCAGGGGTCCCTGACCGATTCTCTGGCTC
CAAGTCTGGCACCTCAGCCTCCCTGGCCATCAGTGGGCTCCGGTCCGAGG
ATGAGGCTGATTATTACTGTGCAGCATGGGATGACAGCCTGAGTGGTCTG
GTTTTCGGCGGAGGAACCAAGCTGACGGTCCTAGGT
Variable heavy chain (V_H) amino acid sequence
                        SEQ ID NO: 33
EVQLLESGGGLVQPGGSLRLSCAASGFTFSTYGMHWVRQAPGKGLEWLSY
ISGGSSYIFYADTVRGRFTISRDNSENALYLQMNSLRAEDTAVYYCARIL
RGGSGMDLWGQGTLVTVSS
Variable heavy chain (V_H) nucleotide sequence
                        SEQ ID NO: 51
GAGGTGCAGCTGTTGGAGTCTGGGGGAGGCTTGGTACAGCCTGGGGGGTC
CCTGAGACTCTCCTGTGCAGCCTCTGGATTCACCTTCAGTACTTATGGCA
TGCACTGGGTCCGCCAGGCTCCAGGGAAGGGGCTGGAGTGGCTTTCATAT
ATTAGTGGTGGTAGTAGTTACATTTTCTACGCAGACACAGTGAGGGGCCG
ATTCACTATCTCCAGAGACAACTCCGAGAACGCACTGTATCTGCAAATGA
ACAGCCTGAGAGCCGAGGACACGGCCGTGTATTACTGTGCGAGAATATTA
AGAGGGGGGAGCGGTATGGACCTCTGGGGCCAAGGTACACTGGTCACCGT
GAGCTCA
CDR amino acid sequences
                        [SEQ ID NO: 4]
V_L CDRs:  CDR1:  CTGSTSNIGAGYKVY
                        [SEQ ID NO: 10]
           CDR2:  GNINRPS
                        [SEQ ID NO: 12]
           CDR3:  CAAWDDSLSGLV
                        [SEQ ID NO: 28]
V_H CDRs:  CDR1:  GFTFSTYGMH
                        [SEQ ID NO: 29]
           CDR2:  GKGLEWLSYISGGSSYIFYADSVRGR
                        [SEQ ID NO: 30]
           CDR3:  CARILRGGSGMDL
Antibody clone G4
Variable light chain (V_L) amino acid sequence
                        SEQ ID NO: 22
QSVLTQPPSASGTPGQRVTISCTGSSSNIGAGYKVYWYQQLPGTAPKLLI
YGNINRPSGVPDRFSGSKSGTSASLAISGLRSEDEADYYCAAWDESITGL
VFGGGTKLTVLG
Variable light chain (V_L) nucleotide sequence
                        SEQ ID NO: 42
CAGTCTGTGCTGACTCAGCCACCCTCAGCGTCTGGGACCCCGGGCAGAG
GGTCACCATCTCTTGCACTGGGAGCAGCTCCAACATCGGGGCAGGTTATA
ATGTATACTGGTATCAGCAGCTCCCAGGAACGGCCCCCAAACTCCTCATC
```

```
TATGGTAACATCAATCGGCCCTCAGGGGTCCCTGACCGATTCTCTGGCTC

CAAGTCTGGCACCTCAGCCTCCCTGGCCATCAGTGGGCTCCGGTCCGAGG

ATGAGGCTGATTATTACTGTGCAGCATGGGATGACAGCCTGAGTGGTCTG

GTTTTCGGCGGAGGAACCAAGCTGACGGTCCTAGGT
```

Variable heavy chain (V_H) amino acid sequence
SEQ ID NO: 34
```
EVQLLESGGGLVQPGGSLRLSCAASGFTFSTYGMHWVRQAPGKGLEWLSY

ISGGSSYIFYADSVRGRFTISRDNSENALYLQMNSLRAEDTAVYYCARIL

RGGSGMDLWGQGTLVTVSS
```

Variable heavy chain (V_H) nucleotide sequence
SEQ ID NO: 52
```
GAGGTGCAGCTGTTGGAGTCTGGGGGAGGCTTGGTACAGCCTGGGGGGTC

CCTGAGACTCTCCTGTGCAGCCTCTGGATTCACCTTCAGTACTTATGGCA

TGCACTGGGTCCGCCAGGCTCCAGGGAAGGGGCTGGAGTGGCTTTCATAT

ATTAGTGGTGGTAGTAGTTACATTTTCTACGCAGACTCAGTGAGGGGCCG

ATTCACCATCTCCAGAGACAACTCCGAGAACGCGCTGTATCTGCAAATGA

ACAGCCTGAGAGCCGAGGACACGGCCGTGTATTACTGTGCGAGAATATTA

GAGGCGGGAGCGGTATGGACCTCTGGGGCCAAGGTACACTGGTCACCGT

GAGCTCA
```

CDR amino acid sequences
```
                                           [SEQ ID NO: 6]
V_L CDRs:    CDR1:   CTGSSSNIGAGYKVY
                                           [SEQ ID NO: 10]
             CDR2:   GNINRPS
                                           [SEQ ID NO: 14]
             CDR3:   CAAWDESITGLV
                                           [SEQ ID NO: 28]
V_H CDRs:    CDR1:   GFTFSTYGMH
                                           [SEQ ID NO: 29]
             CDR2:   GKGLEWLSYISGGSSYIFYADSVRGR
                                           [SEQ ID NO: 30]
             CDR3:   CARILRGGSGMDL
```

Antibody clone F6
Variable light chain (V_L) amino acid sequence
SEQ ID NO: 23
```
QSVLTQPPSASGTPGQRVTISCTGSSSNIGAGYDVYWYQQLPGTAPKLLI

YRNINRPSGVPDRFSGSKSGTSASLAISGLRSEDEADYYCAAWDGSLLGL

VFGGGTKLTVLG
```

Variable light chain (V_L) nucleotide sequence
SEQ ID NO: 43
```
CAGTCTGTGCTGACTCAGCCACCCTCAGCGTCTGGGACCCCCGGGCAGAG

GGTCACCATCTCTTGCACTGGGAGCAGCTCCAACATCGGGGCAGGTTATG

ATGTATACTGGTATCAGCAGCTCCCAGGAACGGCCCCCAAACTCCTCATC

TATCGTAACATCAATCGGCCCTCAGGGGTCCCTGACCGATTCTCTGGCTC

CAAGTCTGGCACCTCAGCCTCCCTGGCCATCAGTGGGCTCCGGTCCGAGG

ATGAGGCTGATTATTACTGTGCAGCATGGGATGGCAGCCTGCTGGGTCTG

GTTTTCGGCGGAGGAACCAAGCTGACGGTCCTAGGT
```

Variable heavy chain (V_H) amino acid sequence
SEQ ID NO: 35
```
EVQLLESGGGLVQPGGSLRLSCAASGFTFSTYGMHWVRQAPGKGLEWLSY

ISGGSSYIFYADSVRGRFTISRDNSENALYLQMNSLRAEDTAVYYCARIL

RGGSGMDLWGQGTLVTVSS
```

Variable heavy chain (V_H) nucleotide sequence
SEQ ID NO: 53
```
GAGGTGCAGCTGTTGGAGTCTGGGGGAGGCTTGGTACAGCCTGGGGGGTC

CCTGAGACTCTCCTGTGCAGCCTCTGGATTCACCTTCAGTACTTATGGCA

TGCACTGGGTTCGCCAGGCTCCAGGGAAGGGGCTGGAGTGGCTTTCATAT

ATTAGTGGTGGTAGTAGTTACATTTTCTACGCAGACTCAGTGAGGGGCCG

ATTCACCATCTCCAGAGACAACTCCGAGAACGCGCTGTATCTGCAAATGA

ACAGCCTGAGAGCCGAGGACACGGCCGTGTATTACTGTGCGAGAATATTA

AGAGGCGGGAGCGGTATGGACCTCTGGGGCCAAGGTACACTGGTCACCGT

GAGCTCA
```

CDR amino acid sequences
```
                                           [SEQ ID NO: 7]
V_L CDRs:    CDR1:   CTGSSSNIGAGYDVY
                                           [SEQ ID NO: 11]
             CDR2:   RNINRPS
                                           [SEQ ID NO: 15]
             CDR3:   CAAWDGSLLGLV
                                           [SEQ ID NO: 28]
V_H CDRs:    CDR1:   GFTFSTYGMH
                                           [SEQ ID NO: 29]
             CDR2:   GKGLEWLSYISGGSSYIFYADSVRGR
                                           [SEQ ID NO: 30]
             CDR3:   CARILRGGSGMDL
```

Antibody clone F9
Variable light chain (V_L) amino acid sequence
SEQ ID NO: 24
```
QSVLTQPPSASGTPGQRVTISCTGSSSNIGAGYGVYWYQQLPGTAPKLLI

YGNINRPSGVPDRFSGSKSGTSASLAISGLRSEDEADYYCAAWDGTLTGL

LFGGGTKLTVLG
```

Variable light chain (V_L) nucleotide sequence
SEQ ID NO: 44
```
CAGTCTGTGCTGACTCAGCCACCCTCAGCGTCTGGGACCCCCGGGCAGAG

GGTCACCATCTCTTGCACTGGGAGCAGCTCCAACATCGGGGCAGGTTATG

GTGTATACTGGTATCAGCAGCTCCCAGGAACGGCCCCCAAACTCCTCATC

TATGGTAACATCAATCGGCCCTCAGGGGTCCCTGACCGATTCTCTGGCTC

CAAGTCTGGCACCTCAGCTTCCCTGGCCATCAGTGGGCTCCGGTCCGAGG

ATGAGGCTGATTATTACTGTGCAGCATGGGATGGCACCCTGACCGGTCTG

CTGTTCGGCGGAGGAACCAAGCTGACGGTCCTAGGT
```

Variable heavy chain (V_H) amino acid sequence
SEQ ID NO: 36
```
EVQLLESGGGLVQPGGSLRLSCAASGFTFSTYGMHWVRQAPGKGLEWLSY

ISGGSSYIFYADSVRGRFTISRDNSENALYLQMNSLRAEDTAVYYCARIL

RGGSGMDLWGQGTLVTVSS
```

Variable heavy chain (V<sub>H</sub>) nucleotide sequence
SEQ ID NO: 54
GAGGTGCAGCTGTTGGAGTCTGGGGGAGGCTTGGTACAGCCTGGGGGGTC
CCTGAGACTCTCCTGTGCAGCCTCTGGATTCACCTTCAGTACTTATGGCA
TGCACTGGGTCCGCCAGGCTCCAGGGAAGGGGCTGGAGTGGCTTTCATAT
ATTAGTGGTGGTAGTAGTTACATTTTCTACGCAGACTCAGTGAGGGGCCG
ATTCACCATCTCCAGAGACAACTCCGAGAACGCGCTGTATCTGCAAATGA
ACAGCCTGAGAGCCGAGGACACGGCCGTGTATTACTGTGCGAGAATATTA
AGAGGCGGGAGCGGTATGGACCTCTGGGGCCAAGGTACACTGGTCACCGT
GAGCTCA CDR amino acid sequences
                                                [SEQ ID NO: 8]
V<sub>L</sub> CDRs:   CDR1:   CTGSSSNIGAGYGVY

[SEQ ID NO: 10]
            CDR2:   GNINRPS

[SEQ ID NO: 16]
            CDR3:   CAAWDGTLTGLL

[SEQ ID NO: 28]
V<sub>H</sub> CDRs:   CDR1:   GFTFSTYGMH

[SEQ ID NO: 29]
            CDR2:   GKGLEWLSYISGGSSYIFYADSVRGR

[SEQ ID NO: 30]
            CDR3:   CARILRGGSGMDL

Antibody clone G12
Variable light chain (V<sub>L</sub>) amino acid sequence
                                                SEQ ID NO: 25
QSVLTQPPSASGTPGQRVTIS<u>CTGSSSNIGAGYNVY</u>WYQQLPGTAPKLLI
Y<u>GNINRPS</u>GVPDRFSGSKSGTSASLAISGLRSEDEADYY<u>CAAWDKSISGL</u>
<u>V</u>FGGGTKLTVLG Variable light chain (V<sub>L</sub>) nucleotide sequence
                                                SEQ ID NO: 45
CAGTCTGTGCTGACTCAGCCACCCTCAGCGTCTGGGACCCCCGGGCAGAG
GGTCACCATCTCTTGCACTGGGAGCAGCTCCAACATCGGGGCGGGTTACA
ATGTATACTGGTATCAGCAGCTCCCAGGAACGGCCCCCAAACTCCTCATC
TATGGTAACATCAATCGGCCCTCAGGGGTCCCTGACCGATTCTCTGGCTC
CAAGTCTGGCACCTCAGCCTCCCTGGCCATCAGTGGGCTCCGGTCCGAGG
ATGAGGCTGATTATTACTGTGCAGCATGGGATAAGAGCATTTCTGGTCTG
GTTTTCGGCGGAGGAACCAAGCTGACGGTCCTAGGT Variable heavy chain (V<sub>H</sub>) amino acid sequence
                                                SEQ ID NO: 37
EVQLLESGGGLVQPGGSLRLSCAAS<u>GFTFSTYGMH</u>WVRQAP<u>GKGLEWLSY</u>
<u>ISGGSSYIFYADSVRGR</u>FTISRDNSENALYLQMNSLRAEDTAVYY<u>CARIL</u>
<u>RGGSGMDL</u>WGQGTLVTVSS Variable heavy chain (V<sub>H</sub>) nucleotide sequence
                                                SEQ ID NO: 55
GAGGTGCAGCTGTTGGAGTCTGGGGGAGGCTTGGTACAGCCTGGGGGGTC
CCTGAGACTCTCCTGTGCAGCCTCTGGATTCACCTTCAGTACTTATGGCA
TGCACTGGGTCCGCCAGGCTCCAGGGAAGGGGCTGGAGTGGCTTTCATAT
ATTAGTGGTGGTAGTAGTTACATTTTCTACGCAGACTCAGTGAGGGGCCG
ATTCACCATCTCCAGAGACAACTCCGAGAACGCGCTGTATCTGCAAATGA
ACAGCCTGAGAGCCGAGGACACGGCCGTGTATTACTGTGCGAGAATATTA
AGAGGCGGGAGCGGTATGGACCTCTGGGGCCAAGGTACACTGGTCACCGT
GAGCTCA CDR amino acid sequences
                                                [SEQ ID NO: 9]
V<sub>L</sub> CDRs:   CDR1:   CTGSSSNIGAGYNVY

[SEQ ID NO: 10]
            CDR2:   GNINRPS

[SEQ ID NO: 17]
            CDR3:   CAAWDKSISGLV

[SEQ ID NO: 28]
V<sub>H</sub> CDRs:   CDR1:   GFTFSTYGMH

[SEQ ID NO: 29]
            CDR2:   GKGLEWLSYISGGSSYIFYADSVRGR

[SEQ ID NO: 30]
            CDR3:   CARILRGGSGMDL

Antibody clone H12
Variable light chain (V<sub>L</sub>) amino acid sequence
                                                SEQ ID NO: 26
QSVLTQPPSASGTPGQRVTIS<u>CTGSSSNIGAGYNVY</u>WYQQLPGTAPKLLI
Y<u>GNINRPS</u>GVPDRFSGSKSGTSASLAISGLRSEDEADYY<u>CAAWDDSLSGL</u>
<u>V</u>FGGGTKLTVLG Variable light chain (V<sub>L</sub>) nucleotide sequence
                                                SEQ ID NO: 46
CAGTCTGTGCTGACTCAGCCACCCTCAGCGTCTGGGACCCCCGGGCAGAG
GGTCACCATCTCTTGCACTGGGAGCAGCTCCAACATCGGGGCAGGTTATA
ATGTATACTGGTATCAGCAGCTCCCAGGAACGGCCCCCAAACTCCTCATC
TATGGTAACATCAATCGGCCCTCAGGGGTCCCTGACCGATTCTCTGGCTC
CAAGTCTGGCACCTCAGCCTCCCTGGCCATCAGTGGGCTCCGGTCCGAGG
ATGAGGCTGATTATTACTGTGCAGCATGGGATGACAGCCTGAGTGGTCTG
GTTTTCGGCGGAGGAACCAAGCTGACGGTCCTAGGTGAGTAGAACGTACG
CTAGCAAGCTTGGATCCACGATCCTGAGCAAGGACCTCTGCCCTCCCTGT
TCAGACCCTTGCTTGCCTCAGCAGGTCATTACAACCACTTCACCTCTGAC
CGCAGGGGCAGGGACTAGATAGAATGACCTACTGAGCCTCGTCTGTCTG
TCTGTCTGTCTCTGTTTGTCTGTCTGTCTCTGTTTGTCTCTCTGTC
TGTCTGACAGGCGCAGGCTGGGTCTCTAAGCCTTGTTCTGTTCTGGCCTC
CTCAGTCTGGGTTCTTGTCGGAACAGCTTTGCCCTTGGGTTACCTGGGTT
CCATCTCCTGGGGAATTGGGAACAAGGGGTCTGAGGGAGGCACCTCCTGG
GAGACTTTAGAAGGACCCAGTGCCCTCGGGGCTGATGCTCGGGA Variable heavy chain (V<sub>H</sub>) amino acid sequence
                                                SEQ ID NO: 38
EVQLLESGGGLVQPGGSLRLSCAAS<u>GFTFSTYGMH</u>WVRQAP<u>GKGLEWLSY</u>
<u>ISGGSSYIFYADSVRGR</u>FTISRDNSENALYLQMNSLRAEDTAVYY<u>CARIL</u>
<u>RGGSGMDL</u>WGQGTLVTVSS Variable heavy chain (V<sub>H</sub>) nucleotide sequence
                                                SEQ ID NO: 56
GAGGTGCAGCTGTTGGAGTCTGGGGGAGGCTTGGTACAGCCTGGGGGGTC
CCTGAGACTCTCCTGTGCAGCCTCTGGATTCACCTTCAGTACTTATGGCA -continued

```
TGCACTGGGTCCGCCAGGCTCCAGGGAAGGGGCTGGAGTGGCTTTCATAT
ATTAGTGGTGGTAGTAGTTACATTTTCTACGCAGACTCAGTGAGGGGCCG
ATTCACCATCTCCAGAGACAACTCCGAGAACGCGCTGTATCTGCAAATGA
ACAGCCTGAGAGCCGAGGACACGGCCGTGTATTACTGTGCGAGAATATTA
AGAGGCGGGAGCGGTATGGACCTCTGGGGCCAAGGTACACTGGTCACCGT
GAGCTCAGGTGAGTCGTACGCTAGCAAGCTTTCTGGGGCAGGCCAGGCCT
GACCTTGGCTTTGGGGCAGGGAGGGGCTAAGGTGAGGCAGGTGGCGCCA
GCCAGGTGCACACCCAATGCCCATGAGCCCAGACACTGGACGCTGAACCT
CGCGGACAGTTAAGAACCCAGGGGCCTCTGCGCCCTGGGCCCAGCTCTGT
CCCACACCGCGGTCACATGGCACCACCTCTCTTGCAGCCTCCACCAAGGG
CCCATCGGTCTTCCCCCTGGCACCCTCCTCCAAGAGCACCTCTGGGGCA
CAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGC
TGTCCTACAGTCCTCACGACTCTA
```

CDR amino acid sequences

V<sub>L</sub> CDRs:  CDR1:  CTGSSSNIGAGYNVY                [SEQ ID NO: 9]

CDR2:  GNINRPS                         [SEQ ID NO: 10]

CDR3:  CAAWDDSLSGLV                    [SEQ ID NO: 12]

V<sub>H</sub> CDRs:  CDR1:  GFTFSTYGMH                      [SEQ ID NO: 28]

CDR2:  GKGLEWLSYISGGSSYIFYADSVRGR      [SEQ ID NO: 29]

CDR3:  CARILRGGSGMDL                   [SEQ ID NO: 30]

Antibody clones B9 and H11
Variable light chain (V<sub>L</sub>) amino acid sequence
                                                SEQ ID NO: 27
QSVLTQPPSASGTPGQRVTIS<u>CTGSSSNIGAGYNVY</u>WYQQLPGTAPKLLI Y<u>GNINRPS</u>GVPDRFSGSKSGTSASLAISGLRSEDEADYY<u>CAAWDGGLLGL</u>

<u>V</u>FGGGTKLTVLG

Variable light chain (V<sub>L</sub>) nucleotide sequence
                                                SEQ ID NO: 47
```
CAGTCTGTGCTGACTCAGCCACCCTCAGCGTCTGGGACCCCCGGGCAGAG
GGTCACCATCTCTTGCACTGGGAGCAGCTCCAACATCGGGGCAGGTTATA
ATGTATACTGGTATCAGCAGCTCCCAGGAACAGCCCCCAAACTCCTCATC
TATGGTAACATCAATCGGCCCTCAGGGGTCCCTGACCGATTCTCTGGCTC
CAAGTCTGGCACCTCAGCCTCCCTGGCCATCAGTGGGCTCCGGTCCGAGG
ATGAGGCTGATTATTACTGTGCAGCATGGGATGGCGGCCTGCTGGGTCTG
GTTTTCGGCGGAGGAACCAAGCTGACGGTCCTAGGT
```

Variable heavy chain (V<sub>H</sub>) amino acid sequence
                                                SEQ ID NO: 39
EVQLLESGGGLVQPGGSLRLSCAAS<u>GFTFSTYGMH</u>WVRQAP<u>GKGLEWLSY</u>

<u>ISGGSSYIFYADSVRGR</u>FTISRDNSENALYLQMNSLRAEDTAVYYC<u>CARIL</u>

<u>RGGSGMDL</u>WGQGTLVTVSS

Variable heavy chain (V<sub>H</sub>) nucleotide sequence
                                                SEQ ID NO: 57
```
GAGGTGCAGCTGTTGGAGTCTGGGGGAGGCTTGGTACAGCCTGGGGGGTC
CCTGAGACTCTCCTGTGCAGCCTCTGGATTCACCTTCAGTACTTATGGCA
TGCACTGGGTCCGCCAGGCTCCAGGGAAGGGGCTGGAGTGGCTTTCATAT
ATTAGTGGTGGTAGTAGTTACATTTTCTACGCAGACTCAGTGAGGGGCCG
ATTCACCATCTCCAGAGACAACTCCGAGAACGCGCTGTATCTGCAAATGA
ACAGCCTGAGAGCCGAGGACACGGCCGTGTATTACTGTGCGAGAATATTA
AGAGGCGGGAGCGGTATGGACCTCTGGGGCCAAGGTACACTGGTCACCGT
GAGCTCAGGTGAGTCGTACGCTAGCAAGCTTTCTGGGGCAGGCCAGGCCT
GACCTTGGCTTTGGGGCAGG
```

CDR amino acid sequences

V<sub>L</sub> CDRs:  CDR1:  CTGSSSNIGAGYNVY                [SEQ ID NO: 9]

CDR2:  GNINRPS                         [SEQ ID NO: 10]

CDR3:  CAAWDGGLLGLV                    [SEQ ID NO: 18]

V<sub>H</sub> CDRs:  CDR1:  GFTFSTYGMH                      [SEQ ID NO: 28]

CDR2:  GKGLEWLSYISGGSSYIFYADSVRGR      [SEQ ID NO: 29]

CDR3:  CARILRGGSGMDL                   [SEQ ID NO: 30]

Constant Regions of Exemplary Antibodies of the Invention

>sp|P01857|IGHG1_HUMAN Ig gamma-1 heavy chain
C region OS = Homo sapiens GN = IGHG1 PE = 1
SV = 1
                                                [SEQ ID NO: 62]
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

>gi|186127|gb|AAA59107.1|immunoglobulin lambda
light chain C2 region [Homo sapiens]
                                                [SEQ ID NO: 63]
QPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVA

PTECS

Exemplary Framework Mutations in Heavy Chain Variable Region (V<sub>H</sub>)

Mutations are indicated below in bold underlined.

Variable heavy chain (VH) amino acid sequence
                                                [SEQ ID NO: 64]
EVQLLESGGGLVQPGGSLRLSCAASGFTFSTYGMHWVRQAPGKGLEWLSY ISGGSSYIFYADSVRGRFTISRDNSEN<u>T</u>LYLQMNSLRAEDTAVYYCARIL

```
RGGSGMDLWGQGTLVTVSS
Variable heavy chain (VH) nucleotide sequence
                                        [SEQ ID NO: 65]
GAGGTGCAGCTGTTGGAGTCTGGGGGAGGCTTGGTACAGCCTGGGGGTC

CCTGAGACTCTCCTGTGCAGCCTCTGGATTCACCTTCAGTACTTATGGCA

TGCACTGGGTCCGCCAGGCTCCAGGGAAGGGGCTGGAGTGGCTTTCATAT

ATTAGTGGTGGTAGTAGTTACATTTTCTACGCAGACTCAGTGAGGGCCG

ATTCACCATCTCCAGAGACAACTCCGAGAACACGCTGTATCTGCAAATGA

ACAGCCTGAGAGCCGAGGACACGGCCGTGTATTACTGTGCGAGAATATTA

AGAGGCGGGAGCGGTATGGACCTCTGGGGCCAAGGTACACTGGTCACCGT

GAGCTCA

Variable heavy chain (VH) amino acid sequence
                                        [SEQ ID NO: 66]
EVQLLESGGGLVQPGGSLRLSCAASGFTFSTYGMHWVRQAPGKGLEWLSY

ISGGSSYIFYADSVRGRFTISRDNSKNTLYLQMNSLRAEDTAVYYCARIL

RGGSGMDLWGQGTLVTVSS

Variable heavy chain (VH) nucleotide sequence
                                        [SEQ ID NO: 67]
GAGGTGCAGCTGTTGGAGTCTGGGGGAGGCTTGGTACAGCCTGGGGGTC

CCTGAGACTCTCCTGTGCAGCCTCTGGATTCACCTTCAGTACTTATGGCA

TGCACTGGGTCCGCCAGGCTCCAGGGAAGGGGCTGGAGTGGCTTTCATAT

ATTAGTGGTGGTAGTAGTTACATTTTCTACGCAGACTCAGTGAGGGCCG

ATTCACCATCTCCAGAGACAACTCCAAGAACACGCTGTATCTGCAAATGA

ACAGCCTGAGAGCCGAGGACACGGCCGTGTATTACTGTGCGAGAATATTA

AGAGGCGGGAGCGGTATGGACCTCTGGGGCCAAGGTACACTGGTCACCGT

GAGCTCA
```

TABLE 11

Antibody clone amino acid changes and position in $V_L$ relative to antibody B44

| Antibody clone | Amino acid change | Amino acid change | Amino acid change | Amino acid change | Amino acid change |
|---|---|---|---|---|---|
| A4 | S26T | D34K | | | |
| A5 | D34H | N53S | A73G | D95S | L97S |
| G4 | D34K | D95E | L97I | | |
| F6 | G52R | D95G | S98L | | |
| F9 | D34G | D95G | S96T | S98T | V101L |
| G12 | D34N | D95K | L97I | | |
| H12 | D34N | | | | |
| B9 | D34N | D95G | S96G | S98L | |
| C4 | S26T | D34K | | | |
| H11 | D34N | D95G | S96G | S98L | |

TABLE 12

Antibody clone amino acid changes and position in $V_H$ relative to antibody B44

| Antibody clone | Amino acid change |
|---|---|
| A4 | |
| A5 | |
| G4 | |
| F6 | |
| F9 | |
| G12 | |
| H12 | |
| B9 | |
| C4 | S63T |
| H11 | |

Example 11: Exemplary Pharmaceutical Formulations

Whilst it is possible for an antibody of the invention to be administered alone, it is preferable to present it as a medicament or pharmaceutical formulation, together with one or more acceptable carriers. The carrier(s) must be "acceptable" in the sense of being compatible with the agent of the invention and not deleterious to the recipients thereof. Typically, the carriers will be water or saline which will be sterile and pyrogen-free.

The following examples illustrate medicaments and pharmaceutical compositions according to the invention in which the active ingredient is an antibody of the invention.

Example A: Tablet

| Active ingredient | 1 mg |
|---|---|
| Lactose | 200 mg |
| Starch | 50 mg |
| Polyvinylpyrrolidone | 5 mg |
| Magnesium stearate | 4 mg |

Tablets are prepared from the foregoing ingredients by wet granulation followed by compression.

Example B: Ophthalmic Solution

| Active ingredient | 1 mg |
|---|---|
| Sodium chloride, analytical grade | 0.9 g |
| Thiomersal | 0.001 g |
| Purified water to | 100 ml |
| pH adjusted to | 7.5 |

Example C: Tablet Formulations

The following formulations A and B are prepared by wet granulation of the ingredients with a solution of povidone, followed by addition of magnesium stearate and compression.

| Formulation A | | |
|---|---|---|
| | mg/tablet | mg/tablet |
| (a) Active ingredient | 1 | 1 |
| (b) Lactose B.P. | 210 | 26 |

Formulation A -continued

|  | mg/tablet | mg/tablet |
|---|---|---|
| (c) Povidone B.P. | 15 | 9 |
| (d) Sodium Starch Glycolate | 20 | 12 |
| (e) Magnesium Stearate | 5 | 3 |
|  | 251 | 51 |

Formulation B

|  | mg/tablet | mg/tablet |
|---|---|---|
| (a) Active ingredient | 1 | 1 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
|  | 251 | 51 |

Formulation C

|  | mg/tablet |
|---|---|
| Active ingredient | 1 |
| Lactose | 200 |
| Starch | 50 |
| Povidone | 5 |
| Magnesium stearate | 4 |
|  | 260 |

The following formulations, D and E, are prepared by direct compression of the admixed ingredients. The lactose used in formulation E is of the direction compression type.

Formulation D

|  | mg/capsule |
|---|---|
| Active Ingredient | 1 |
| Pregelatinised Starch NF15 | 150 |
|  | 151 |

Formulation E

|  | mg/capsule |
|---|---|
| Active Ingredient | 1 |
| Lactose | 150 |
| Avicel ® | 100 |
|  | 251 |

Formulation F (Controlled Release Formulation)

The formulation is prepared by wet granulation of the ingredients (below) with a solution of povidone followed by the addition of magnesium stearate and compression.

|  | mg/tablet |
|---|---|
| (a) Active Ingredient | 1 |
| (b) Hydroxypropylmethylcellulose (Methocel K4M Premium) ® | 112 |
| (c) Lactose B.P. | 53 |
| (d) Povidone B.P.C. | 28 |
| (e) Magnesium Stearate | 7 |
|  | 201 |

Drug release takes place over a period of about 6-8 hours and was complete after 12 hours.

Example D: Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

|  | mg/capsule |
|---|---|
| (a) Active ingredient | 1 |
| (b) Lactose B.P. | 143 |
| (c) Sodium Starch Glycolate | 25 |
| (d) Magnesium Stearate | 2 |
|  | 171 |

Formulation C

|  | mg/capsule |
|---|---|
| (a) Active ingredient | 1 |
| (b) Macrogol 4000 BP | 350 |
|  | 351 |

Capsules are prepared by melting the Macrogol 4000 BP, dispersing the active ingredient in the melt and filling the melt into a two-part hard gelatin capsule.

Formulation D

|  | mg/capsule |
|---|---|
| Active ingredient | 1 |
| Lecithin | 100 |
| *Arachis* Oil | 100 |
|  | 201 |

Capsules are prepared by dispersing the active ingredient in the lecithin and *arachis* oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
| --- | --- |
| (a) Active ingredient | 1 |
| (b) Microcrystalline Cellulose | 125 |
| (c) Lactose BP | 125 |
| (d) Ethyl Cellulose | 13 |
|  | 264 |

Example E: Injectable Formulation

| Active ingredient | 1 mg |
| --- | --- |
| Sterile, pyrogen free phosphate buffer (pH 7.0) to | 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F: Intramuscular Injection

| Active ingredient | 1 mg |
| --- | --- |
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G: Syrup Suspension

| Active ingredient | 1 mg |
| --- | --- |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H: Suppository

|  | mg/suppository |
| --- | --- |
| Active ingredient (63 μm)* | 1 |
| Hard Fat, BP (Witepsol H15 - Dynamit Nobel) | 1770 |
|  | 1771 |

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Wtepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I: Pessaries

|  | mg/pessary |
| --- | --- |
| Active ingredient | 1 |
| Anhydrate Dextrose | 380 |
| Potato Starch | 363 |
| Magnesium Stearate | 7 |
|  | 751 |

The above ingredients are mixed directly and pessaries prepared by direct compression of the resulting mixture.

Example 12: Effect of Exemplary Antibodies In Vivo in Mouse Tumour Model

The anti-tumour activity of an anti-CD40 antibody of the invention was studied in human CD40 transgenic mice inoculated with bladder cancer cells. MB49 bladder cancer cells were inoculated subcutaneously into human CD40 transgenic mice. The mice were treated peritumourally on day 7 and 10 with G12 or controls. Treatment with G12 results in a significant anti-tumour effect compared to the isotype control.

The reference antibody S2C6 is an chimeric anti-CD40 antibody composed of the murine variable domains, VH and VL, fused to the human gammal and kappa constant regions respectively (European patent no. EP1885399, Francisco et al., 2000 Cancer Research). The antibody is thus an analog to the humanized anti-CD40 antibody SGN-40 (Law et al., 2005 Cancer Research). SGN-40 has been studied in clinical trials (Advani et al., 2009 J Clinical Oncology; Hussein et al., 2010 Haematologica).

Material and Methods

The MB49 cell line is a carcinogen induced transitional cell carcinoma derived from C57BL/6 male mice (Summerhayes & Franks, 1979, Journal of the National Cancer Institute). MB49 express murine CD40 but do not express human CD40. G12 does not cross react with murine CD40 and cannot bind to the MB49 tumour cells.

$2.5 \times 10^5$ bladder cancer MB49 cells were inoculated subcutaneously in the flank of female human CD40 transgenic C57BL/6 mice on day 0. The human CD40 transgenic mice express human wild-type CD40 in a mouse CD40 deficient (mCD40−/−) background. Treatment started on day 7 with antibodies injected peritumourally by the subcutaneous tumour on day 7 and day 10 (two doses). The tumour volume was measured 2 time/week with caliper and calculated by the ellipsoid volume formula. Mice were sacrificed if the tumour exceeded 1 cm$^3$ or if ulcers developed. Serum samples were taken 4 h post each treatment. Cytokine levels in the serum samples were analyzed on Mouse ProInflammatory 7-Plex Ultra-Sensitive Kit using Mesoscale discovery platform (MSD, Gaithersburg, Md., USA). The antibody titer was measured in the serum using sandwich ELISA. The MB49 cell line is a carcinogen induced transitional cell carcinoma derived from C57BL/6 male mice (Summerhayes & Franks, 1979, Journal of the National Cancer Institute). MB49 express murine CD40 but do not express human CD40. G12 does not cross react with murine CD40 and can not bind to the MB49 tumour cells.

Results

The results are shown in FIG. 10.

Treatment with G12 significantly increases the survival of animals compared to isotype control (p<0.013). The survival curve of mice treated with G12 compared to S2C6 (p<0.13). The survival of mice treated with S2C6 compared to isotype control (p<0.088).

Example 13: Effect of Exemplary Antibodies In Vivo in Mouse Tumour Model

The anti-tumour activity of the anti-CD40 antibodies Interleukin-6 (IL-6), Tumour Necrosis factor-alpha (TNF-α) and Keratinocyte-derived Cytokine (KC) (also known as Chemokine (C—X—C motif) ligand 1/CXCL1) were studied using pooled data from a larger group of treated animals. The G12 treatment group contained a group of 20 animals, the S2C6 treatment group contain 12 animals, and the isotype control group contained 20 animals.

MB49 bladder cancer cells were inoculated subcutaneously into human CD40 transgenic mice. The mice were treated peritumourally on day 7 and 10 with G12, or controls. Treatment with G12 provides a significant increase of survival of tumour-bearing mice compared to the group treated with the isotype control (FIG. 11).

Serum samples were taken from treated mice and analysed for cytokine levels. The cytokine levels after treatment demonstrates a stronger induction of the immune response of G12 compared to the reference antibody, S2C6 (FIG. 12).

Material and Methods $2.5 \times 10^5$ bladder cancer MB49 cells were inoculated subcutaneously in the flank of female human CD40 transgenic C57BL/6 mice on day 0. The human CD40 transgenic mice express human wild-type CD40 in a mouse CD40 deficient (mCD40−/−) background. Treatment started on day 7 with antibodies injected peritumourally by the subcutaneous tumour on day 7 and day 10 (two doses). The tumour volume was measured 2 time/week with caliper and calculated by the ellipsoid volume formula. Mice were sacrificed if the tumour exceeded 1 cm$^3$ or if ulcers developed. Serum samples were taken 4 h post each treatment. Cytokine levels in the serum samples were analyzed on Mouse ProInflammatory 7-Plex Ultra-Sensitive Kit using Mesoscale discovery platform (MSD, Gaithersburg, Md., USA). The statistical analysis was performed using Graph Pad Prism 6.0 (GraphPad Software, Inc. La Jolla, Calif.)

Results

The results are shown in FIGS. 11 and 12.

Example 14: In Vivo Analysis of Antibody Levels

The treated mice were analysed for antibody levels in serum. Serum samples were taken after the first (day 7) and second treatment (day 10). The antibody titer was significantly lower for the anti-CD40 antibody clone compared to reference antibodies. Data shown in FIG. 13.

Materials & Methods

Serum samples taken 4 h after the first (day 7) and the second (day 10) treatment from the experiment described in Example I was analyzed for antibody levels. The antibody titer was measured in the serum using sandwich ELISA.

The G12 treatment group consisted of 23 mice (N=23), the S2C6 reference antibody treatment group consisted of 23 mice (N=23) and the treatment group of the isotype control consisted of 18 mice (N=18).

Results

The results are shown FIG. 13.

REFERENCES

Advani et al., Phase I Study of the humanized anti-CD40 monoclonal antibody Dacetuzumab in refractory of recurrent non-hodgkin's lymphoma. *J Clinical Oncology* 27: 4371-4377 (2009)

Armitage et al., Molecular and biological characterization of a murine ligand for CD40. *Nature* 357: 80-82 (1992).

Bajorath, J. Detailed comparison of two molecular models of the human CD40 ligand with an x-ray structure and critical assessment of model-based mutagenesis and residue mapping studies. *J Biol Chem* 273, 24603-9 (1998).

Bajorath, J. et al. Analysis of gp39/CD40 interactions using molecular models and site-directed mutagenesis. *Biochemistry* 34, 9884-92 (1995).

Bajorath, J. et al. Identification of residues on CD40 and its ligand which are critical for the receptor-ligand interaction. *Biochemistry* 34, 1833-44 (1995).

Carter et al., *Nature Reviews Immunology* 6, 343-357 (2006).

Diehl, L. et al. CD40 activation in vivo overcomes peptide-induced peripheral cytotoxic T-lymphocyte tolerance and augments anti-tumor vaccine efficacy. *Nat. Med.* 5, 774-779 (1999).

Ellmark et al., Identification of a Strongly Activating Human Anti-Cd40 Antibody that Suppresses HIV Type 1 Infection. *AIDS Research and Human Rettroviruses*, 24, 3, 367-373, (2008).

Ellmark et al., Modulation of the CD40-CD40L ligand interaction using human anti-CD40 single-chain antibody fragments obtained from the n-CoDeR® phage display library. *Immunology*, 106, 456-463.

European patent no. EP1885399

Fellouse, F. A. et al. High-throughput generation of synthetic antibodies from highly functional minimalist phage-displayed libraries. *J Mol Biol* 373, 924-940 (2007).

Francisco et al., Agonistic properties and in vivo antitumor activity of the anti-CD40 antibody SGN-14. *Cancer Research* 60, 3225-3231 (2000)

French, R. R., et al., CD40 antibody evokes a cytotoxic T-cell response that eradicates lymphoma and bypasses T-cell help. *Nat Med* 5, 548-53 (1999).

Gatenby et al., Why do cancers have high aerobi glycolysis? *Nature review Cancer* 4, 891-899 (2004).

Glaude et al., The CD40 agonist antibody CP-870,893 enhances dendritic cell and B-cell activity and promotes anti-tumor efficacy in SCID-hu mice. *Cancer Immunol Immunotherapy* 60(7):1009-17 (2011).

Hussein et al., A phase I multi-dose study of dacetumuzumab (SGN-40, a humananized anti-CD40 monoclonal antibody) in patients with multiple myeloma. *Haematologica*, 95: 845-848 (2010)

Janeway's Immunobiology, 7:th edition, Garland *Science* (2008).

Kai et al., *Nature Biotechnology*, 26, 209-211 (2008).

Kalbasi, A. et al. CD40 expression by human melanocytic lesions and melanoma cell lines and direct CD40 targeting with the therapeutic anti-CD40 antibody CP-870,893. *J Immunother* 33, 810-816 (2010).

Katakura et al., Journal of Molecular Catalysis B: Enzymatic (2008).

Koide, A., et al. Exploring the capacity of minimalist protein interfaces: interface energetics and affinity maturation to picomolar KD of a single-domain antibody with a flat paratope. *J Mol Biol* 373, 941-953 (2007).

Law et al., Preclinical antilymphoma activity of a humanized anti-CD40 monoclonal antibody, SGN-14 *Cancer Research* 65, 18, 8331-8338 (2005)

Loskog, A. S. & Eliopoulos, A. G. The Janus faces of CD40 in cancer. *Semin. Immunol* 21, 301-307 (2009).

Quezada, S. A., Jarvinen, L. Z., Lind, E. F., & Noelle, R. J. CD40/CD154 interactions at the interface of tolerance and immunity. *Annu. Rev. Immunol.* 22:307-28, 307-328 (2004).

Schonbeck, U. & Libby, P. The CD40/CD154 receptor/ligand dyad. *Cell Mol Life Sci* 58, 4-43 (2001).

Siepmann et al., Rewiring CD40 is necessary for delivery of rescue signals to B cells in germinal centres and subsequent entry into the memory pool. *Immunology,* 102(3), 263-72 (2001).

Sklar et al., *Annual Review Biophysical Biomol Structure,* 31, 97-119, (2002).

Söderlind, E. et al. Recombining germline-derived CDR sequences for creating diverse single-framework antibody libraries. *Nat Biotechnol* 18, 852-6 (2000)

Sotomayor, E. M. et al. Conversion of tumor-specific CD4+ T-cell tolerance to T-cell priming through in vivo ligation of CD40. *Nature Medicine* 5, 780-787 (1999).

Staveley-O'Carroll, K. et al. In vivo ligation of CD40 enhances priming against the endogenous tumor antigen and promotes CD8+ T cell effector function in SV40 T antigen transgenic mice. *J Immunol* 171, 697-707 (2003).

Summerhayes & Franks, *Journal of the National Cancer Institute* 62: 1017-1023 (1979)

Tasci, I. et al., Soluble CD40 ligand levels in otherwise healthy subjects with impaired fasting glucose. *Cell. Life. Sci.* 58, 4-43 (2001).

Tong et al., CD40-directed gene therapy shows prospects for treating human cancers. *Cancer Gene Therapy* 10(1), 1-13 (2003)

Tutt et al., T cell immunity to lymphoma following treatment with anti-CD40 monoclonal antibody. *J Immunol* 168 (6) 2720-8, (2002).

van Kooten, C. & Banchereau, J. CD40-CD40 ligand. *J Leukoc Biol* 67, 2-17 (2000).

van Mierlo, G. J. et al. CD40 stimulation leads to effective therapy of CD40(-) tumors through induction of strong systemic cytotoxic T lymphocyte immunity. *Proc. Natl. Acad. Sci. U.S.A.* 99, 5561-5566 (2002).

White et al., Interaction with Fc IIB is critical for the agonistic activity of anti-CD40 monoclonal antibody *Journal of Immunology* (187), 1754-1763, (2011).

Wilson et al., *Cancer Cell* (19), 101-113, (2011).

---

The invention claimed is:

1. An antibody or an antigen-binding fragment thereof with multivalent binding specificity for CD40, or a fusion of said antibody or antigen-binding fragment which retains the multivalent binding specificity for the CD40, wherein the antibody, fragment, or fusion comprises a variable light chain ($V_L$) comprising three CDRs in which the CDRs comprise the amino acid sequence of SEQ ID NO: 1, 2, or 3, wherein:

(a)

CTGSX$_1$SNIGAGYX$_2$VY     [SEQ ID NO: 1]

wherein:
$X_1$ is S or T; and
$X_2$ is K or H or D or G or N;

(b)

X$_3$NINRPS     [SEQ ID NO: 2]

wherein:
$X_3$ is G or R; or (c)

CAAWDX$_4$X$_5$X$_6$X$_7$GLX$_8$     [SEQ ID NO: 3]

wherein:
$X_4$ is D or S or E or G or K; and
$X_5$ is S or T or G; and
$X_6$ is L or S or T or L or I; and
$X_7$ is S or T or L; and
$X_8$ is V or L;

wherein the antibody, fragment, or fusion comprises a variable heavy chain (V$_H$) comprising three CDRs in which the CDRs comprise the amino acid sequence of:

```
GFTFSTYGMH,              [SEQ ID NO: 28]

GKGLEWLSYISGGSSYIFYADSVRGR,    [SEQ ID NO: 29]
or

CARILRGGSGMDL.           [SEQ ID NO: 30]
```

2. An antibody or antigen-binding fragment, or a fusion thereof, according to claim 1 wherein the antibody, antigen-binding fragment, or fusion thereof is capable of a direct apoptotic effect on tumour cells and an indirect immune cell-mediated cytotoxic effect on the tumour cells.

3. An antibody or antigen-binding fragment, or a fusion thereof, according to claim 1 wherein the antibody, antigen-binding fragment, or fusion-thereof has an affinity (KD) for CD40 in the range $1.0 \times 10^{-10}$ M to $1 \times 10^{-11}$ M and an on-rate (ka) for CD40 in the range $2.7 \times 10^6$ to $1 \times 10^7$ 1/Ms as determined by surface plasmon resonance.

4. An antibody or antigen-binding fragment, or a fusion thereof, according to claim 1 wherein the antibody or antigen-binding fragment, or fusion thereof, comprises an intact antibody.

5. An antibody or antigen-binding fragment, or a fusion thereof, according to claim 1 wherein the antibody or antigen-binding fragment, or a fusion thereof, comprises an antigen-binding fragment selected from the group consisting of: an Fv fragment, and a Fab-like fragment.

6. An antibody or antigen-binding fragment, or a fusion thereof, according to claim 1 wherein the antibody, antigen-binding fragment, or fusion thereof, is human or humanised.

7. An antibody or antigen-binding fragment, or a fusion thereof, according to claim 1 wherein the antibody, fragment, or fusion comprises:

(a) a variable light chain (V$_L$) in which CDR1 comprises an amino acid sequence selected from the group consisting of:

```
CTGSTSNIGAGYKVY;         [SEQ ID NO: 4]

CTGSSSNIGAGYHVY;         [SEQ ID NO: 5]

CTGSSSNIGAGYKVY;         [SEQ ID NO: 6]

CTGSSSNIGAGYDVY;         [SEQ ID NO: 7]

CTGSSSNIGAGYGVY;         [SEQ ID NO: 8]
and

CTGSSSNIGAGYNVY,         [SEQ ID NO: 9]
```

(b) a variable light chain (V$_L$) in which CDR2 comprises or consists of an amino acid sequence selected from the group consisting of:

```
GNINRPS;                 [SEQ ID NO: 10]
and

RNINRPS,                 [SEQ ID NO: 11]
``` and/or (c) a variable light chain (V$_L$) in which CDR3 comprises or consists of an amino acid sequence selected from the group consisting of:

```
CAAWDDSLSGLV;            [SEQ ID NO: 12]

CAAWDSSSSGLV;            [SEQ ID NO: 13]

CAAWDESITGLV;            [SEQ ID NO: 14]

CAAWDGSLLGLV;            [SEQ ID NO: 15]

CAAWDGTLTGLL;            [SEQ ID NO: 16]

CAAWDKSISGLV;            [SEQ ID NO: 17]
and

CAAWDGGLLGLV.            [SEQ ID NO: 18]
```

8. An antibody or antigen-binding fragment, or a fusion thereof, according to claim 1 wherein the antibody, fragment, or fusion comprises a variable light chain (V$_L$) comprising an amino acid sequence selected from the group consisting of:

SEQ ID NO:19; SEQ ID NO:20; SEQ ID NO:21; SEQ ID NO:22; SEQ ID NO:23; SEQ ID NO:24; SEQ ID NO:25; SEQ ID NO:26; and SEQ ID NO:27.

9. An antibody or antigen-binding fragment, or a fusion thereof, according to claim 1 wherein the antibody, fragment, or fusion comprises a variable heavy chain (V$_H$) comprising an amino acid sequence selected from the group consisting of:

SEQ ID NO:31; SEQ ID NO:32; SEQ ID NO:33; SEQ ID NO:34; SEQ ID NO:35; SEQ ID NO:36; SEQ ID NO:37; SEQ ID NO:38; and SEQ ID NO:39.

10. An antibody or antigen-binding fragment, or a fusion thereof, according to claim 1 wherein the antibody, fragment, or fusion comprises a variable light chain (V$_L$) and a variable heavy chain (V$_H$) comprising the following amino acid sequences:

(i) SEQ ID NO:19 and SEQ ID NO:31; or
(ii) SEQ ID NO:20 and SEQ ID NO:32; or
(iii) SEQ ID NO:21 and SEQ ID NO:33; or
(iv) SEQ ID NO:22 and SEQ ID NO:34; or
(v) SEQ ID NO:23 and SEQ ID NO:35; or
(vi) SEQ ID NO:24 and SEQ ID NO:36; or
(vii) SEQ ID NO:25 and SEQ ID NO:37; or
(viii) SEQ ID NO:26 and SEQ ID NO:38; or
(ix) SEQ ID NO:27 and SEQ ID NO:39.

11. An antibody or antigen-binding fragment, or a fusion thereof, according to claim 1 wherein the antibody, fragment, or fusion binds to an epitope within the first domain (D1) of CD40.

12. An antibody or antigen-binding fragment, or a fusion thereof, according to claim 1 wherein the antibody, fragment, or fusion compete for binding to CD40 with one or more antibodies having a variable light chain (V$_L$) and a variable heavy chain (V$_H$) with the following amino acid sequences:

(i) SEQ ID NO:19 and SEQ ID NO:31; or
(ii) SEQ ID NO:20 and SEQ ID NO:32; or
(iii) SEQ ID NO:21 and SEQ ID NO:33; or
(iv) SEQ ID NO:22 and SEQ ID NO:34; or
(v) SEQ ID NO:23 and SEQ ID NO:35; or
(vi) SEQ ID NO:24 and SEQ ID NO:36; or
(vii) SEQ ID NO:25 and SEQ ID NO:37; or
(viii) SEQ ID NO:26 and SEQ ID NO:38; or
(ix) SEQ ID NO:27 and SEQ ID NO:39.

13. An antibody or antigen-binding fragment, or a fusion thereof, according to claim 1 which comprises an antibody Fc-region.

14. An antibody or antigen-binding fragment, or a fusion thereof, according to claim 13 wherein the Fc-region is from an IgG1 antibody.

15. An antibody or antigen-binding fragment, or a fusion thereof, according to claim 13 wherein the Fc-region comprises the amino acid sequence of SEQ ID NO: 62.

16. An antibody or antigen-binding fragment, or a fusion thereof, according to claim 1 further comprising a cytotoxic moiety.

17. An antibody or antigen-binding fragment, or a fusion thereof, according to claim 1 further comprising a readily-detectable moiety.

18. A pharmaceutical composition comprising an effective amount of an antibody or antigen-binding fragment, or fusion thereof, as defined in claim 1, and a pharmaceutically-acceptable buffer, excipient, diluent or carrier.

19. A method for treating an individual with cancer having $CD40^+$ tumor cells, the method comprising the step of administering to an individual in need thereof an effective amount of: an antibody or antigen-binding fragment, or a fusion thereof, according to claim 1.

20. An antibody or antigen-binding fragment, or a fusion thereof, according to claim 5, wherein the Fv fragment is a single chain Fv fragment or a disulphide-bonded Fv fragment; and wherein the Fab-like fragment is selected from the group consisting of a Fab fragment, a Fab' fragment or a $F(ab)_2$ fragment.

* * * * *